(12) United States Patent
Grillari et al.

(10) Patent No.: US 10,125,398 B2
(45) Date of Patent: Nov. 13, 2018

(54) COMPOSITIONS AND METHODS FOR THE DIAGNOSIS AND TREATMENT OF BONE FRACTURES AND DISORDERS

(71) Applicant: Universität für Bodenkultur Wien, Vienna (AT)

(72) Inventors: Johannes Grillari, Bisamberg (AT); Regina Grillari, Bisamberg (AT); Matthias Hackl, Vienna (AT); Elisabeth Schraml, Vienna (AT); Sylvia Weilner, Perzendorf (AT)

(73) Assignee: UNIVERSITAT FUR BODENKULTUR WIEN, Vienna (AT)

( * ) Notice: Subject to any disclaimer, the term of this patent is extended or adjusted under 35 U.S.C. 154(b) by 0 days.

(21) Appl. No.: 15/318,646

(22) PCT Filed: Jun. 11, 2015

(86) PCT No.: PCT/EP2015/063091
§ 371 (c)(1),
(2) Date: Dec. 13, 2016

(87) PCT Pub. No.: WO2015/189345
PCT Pub. Date: Dec. 17, 2015

(65) Prior Publication Data
US 2017/0130268 A1    May 11, 2017

(30) Foreign Application Priority Data

Jun. 13, 2014 (EP) .................................. 14172354
Dec. 17, 2014 (EP) .................................. 14198560

(51) Int. Cl.
*A61K 48/00* (2006.01)
*C12Q 1/6883* (2018.01)
(52) U.S. Cl.
CPC ...... *C12Q 1/6883* (2013.01); *C12Q 2600/118* (2013.01); *C12Q 2600/158* (2013.01); *C12Q 2600/178* (2013.01)
(58) Field of Classification Search
CPC ...................................................... C12Q 1/68
See application file for complete search history.

(56) References Cited

U.S. PATENT DOCUMENTS

2005/0261218 A1* 11/2005 Esau .................. C12N 15/111
514/44 A

FOREIGN PATENT DOCUMENTS

| WO | 2007/023306 A1 | 3/2007 |
| WO | 2011/144761 A1 | 11/2011 |
| WO | 2013/155085 A1 | 10/2013 |

OTHER PUBLICATIONS

Anastas et al, "WNT signalling pathways as therapeutictargets in cancer" (2013) Nature Reviews Cancer, 13(1), 11-26. doi:10.1038/nrc3419.
Bartel, David "MicroRNAs: target recognition and regulatory functions" (2009) Cell,136(2), 215-233. doi:10.1016/j.cell.2009.01.002.
Canalis, Ernesto "Wnt signalling in osteoporosis: mechanisms and noveltherapeutic approaches", (2013) Nature Reviews. Endocrinology, 9(10), 575-83.doi:10.1038/nrendo.2013.154.
Cefalu, Charles "Is bone mineral density predictive of fracture risk reduction?" (2004) Current Medical Research and Opinion, 20(3), 341-349.doi:10.1185/030079903125003062.
Deng et al, "Repair of critical-sized bone defects with anti-miR-31-expressing bone marrow stromal stem 15 cells and poly(glycerol sebacate) scaffolds", (2014) European Cells & Materials, 27, 13-24; discussion 24-5. Retrieved from http://www.ncbi.nlm.nih.gov/pubmed/24425157.
Dong et al, "MicroRNAs regulate osteogenesis and chondrogenesis", (2012) Biochemical and Biophysical Research communications, 418(4), 587-591. doi:10.1016/j.bbrc.2012.01.075.
Kanis et al, "European guidance for the diagnosis and management of osteoporosis in post-menopausal women", International Osteoporosis Foundation (IOF) (2013), 24(1), 23-57. doi:10.1007/s00198-012-2074-y.
Kapinas et al, miR-29 suppression of osteonectin in osteoblasts: regulation during differentiation and by canonical Wnt signaling:, (2009) Journal of Cellular Biochemistry, 108(1), 216-224. doi:10.1002/jcb.22243.
Keller et al, "Toward the blood-borne miRNome of human diseases", Nature Methods, (2011) 8(10), 841-3. doi:10.1038/nmeth.1682.
Li et al, "A microRNA signature for a BMP2-induced 5 osteoblast lineage commitment program", Proceedings of the National Academy of Sciences of the United States of America, (2008) 105(37), 13906-13911. doi:10.1073/pnas.0804438105.
Rubin et al, "Comparison of different screening tools (FRAX®, OST, ORAI, OSIRIS, SCORE and age alone) to identify women with increased risk of fracture. A population-based prospective study" (2013) Bone, 56(1), 16-22. doi:10.1016/j.bone.2013.05.002.
Seeliger et al, "Five Freely Circulating miRNAs and Bone Tissue miRNAs are Associated with Osteoporotic Fractures" (2014) Journal of Bone and Mineral Research : The Official Journal of the American Society for Bone and Mineral Research. doi:10.1002/jbmr2175: J Bone Miner Res. Aug. 2014;29(8):1718-28.
Seeliger et al, "Identification of freely circulating mirnas in the serium, in bone tissue and in cells related to bone homeostasis that re associated with osteoporotic fractures", Journal of Tissue Engineering and Regenerative Medicine, vol. 8, no suppl 1, 2014, p. 270.

(Continued)

*Primary Examiner* — Kimberly Chong
(74) *Attorney, Agent, or Firm* — Loza & Loza, LLP; Michael F. Fedrick

(57) ABSTRACT

The present invention relates to the therapy, prophylaxis and diagnosis of disorders that are associated with aberrant bone mineral density, in particular osteoporosis; wherein the level of selected micro RNAs in samples of patients are detected and wherein an increase or decrease of said level compared to the level of healthy individuals is indicative of the disorder.

Figure 1:
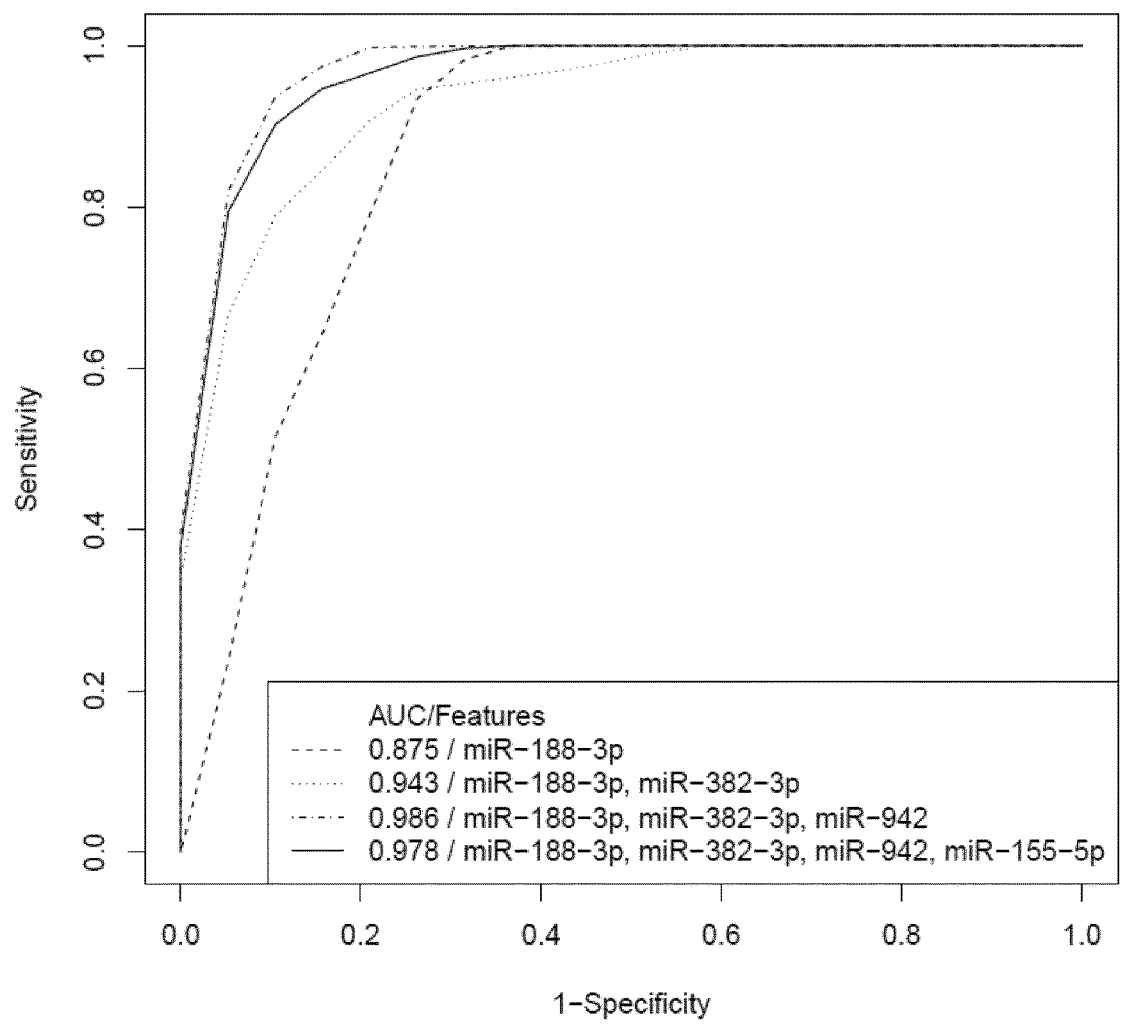
Figure 1:
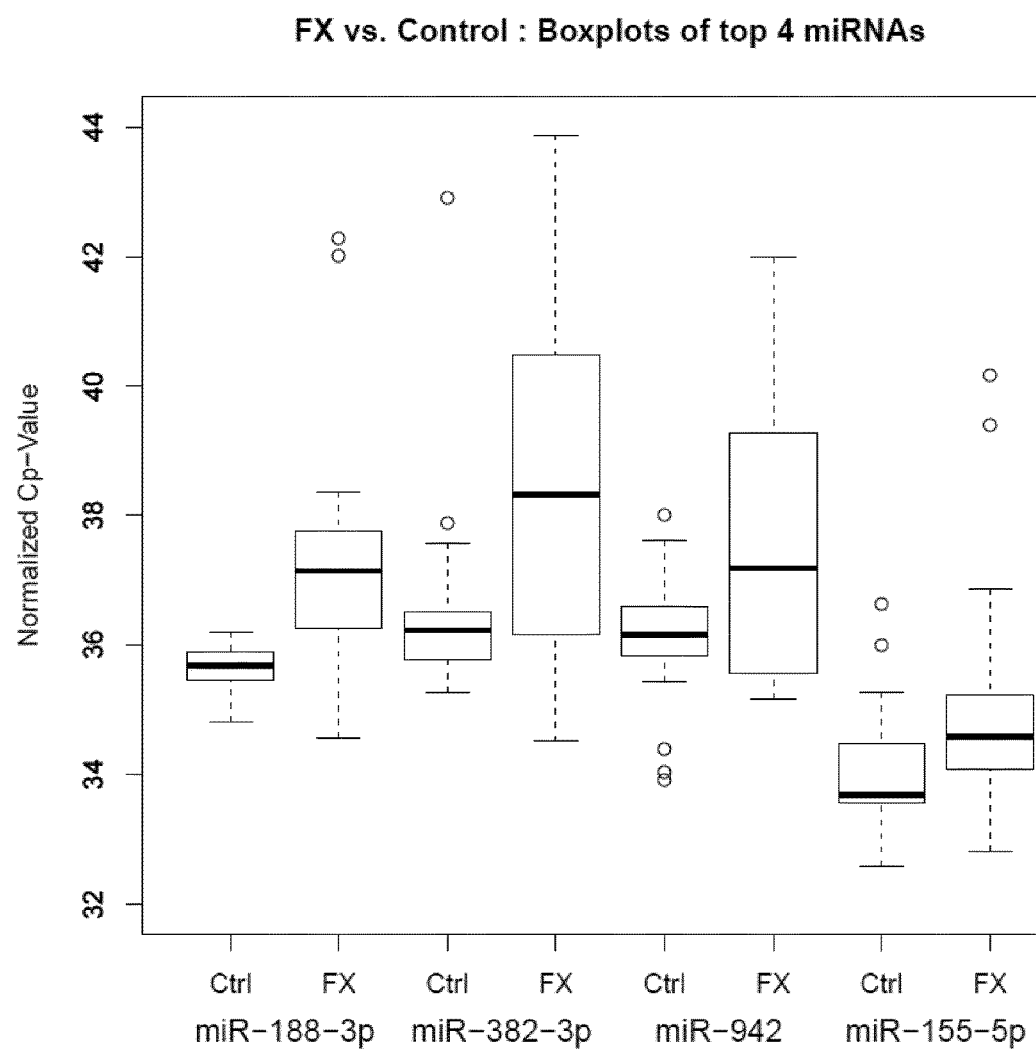
Figure 1:
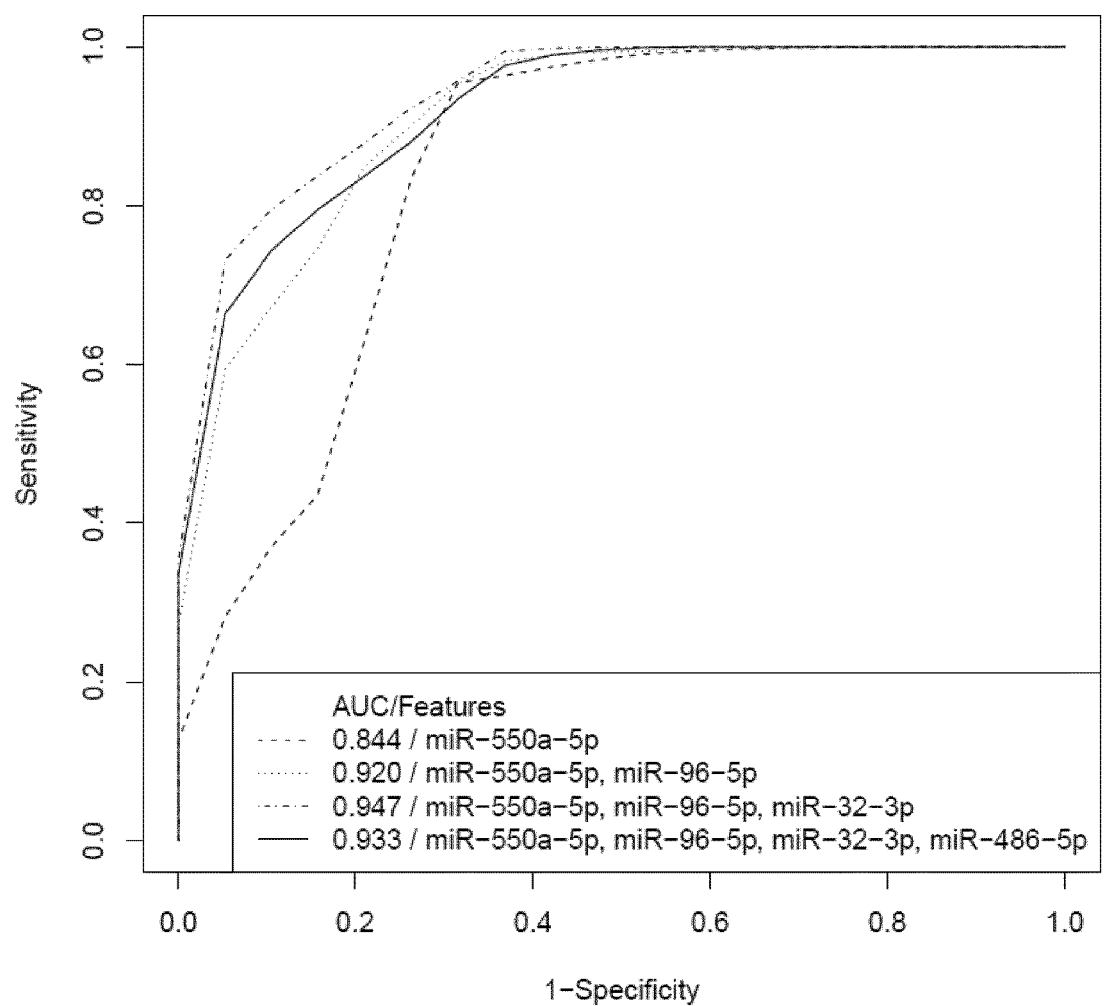
Figure 1:
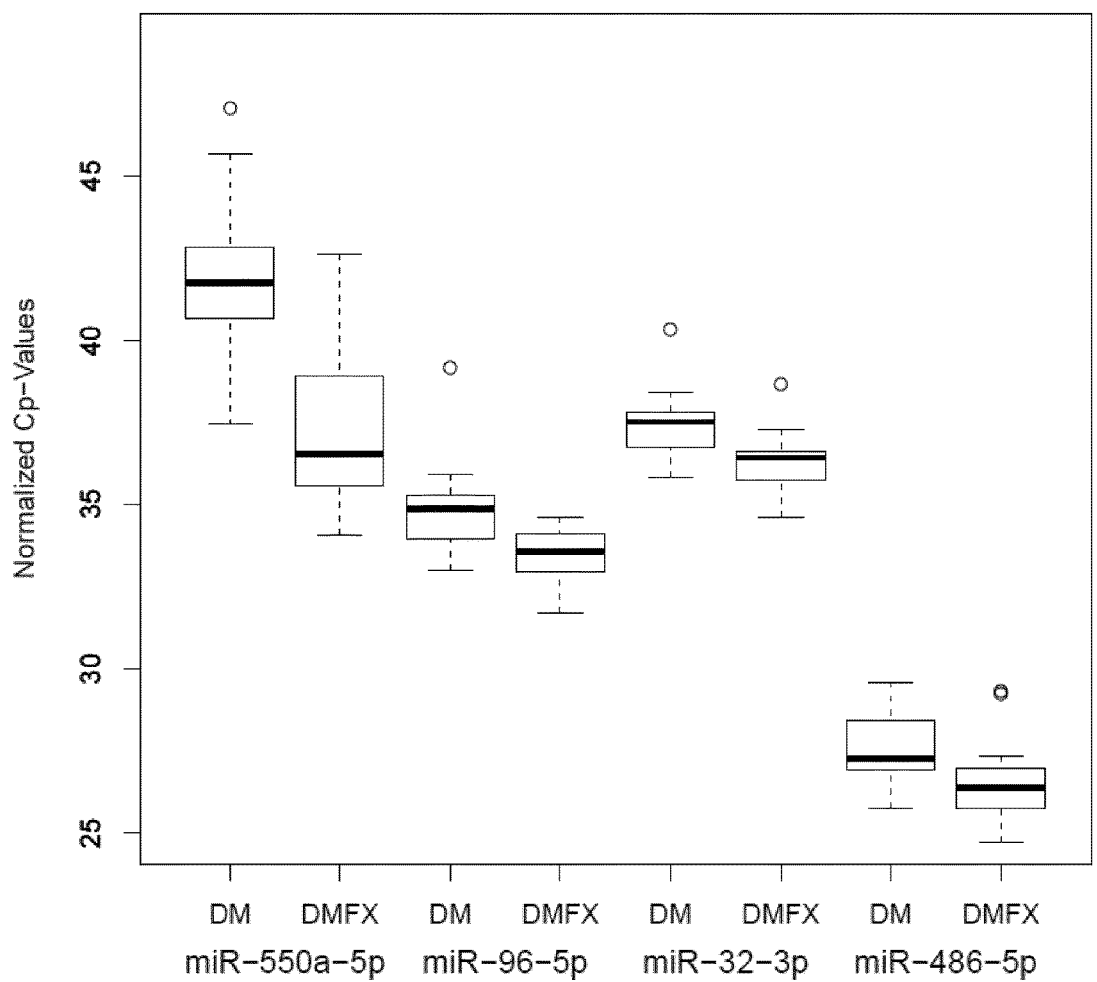

13 Claims, 6 Drawing Sheets
Specification includes a Sequence Listing.

(56) References Cited

OTHER PUBLICATIONS

Trompeter et al, "MicroRNAs miR-26a, miR-26b, and miR-29b accelerate osteogenic differentiation of unrestricted somatic stem cells from human cord blood" (2013) BMC Genomics, 14(1), 111. doi:10.1186/1471-2164-14-111.

van Wijnen et al, "MicroRNA functions in osteogenesis and dysfunctions in osteoporosis", (2013) Current Osteoporosis Reports, 11(2), 72-82. doi:10.1007/s11914-013-0143-6.

Vasikaran et al, "Markers of bone turnover for the prediction of fracture risk and monitoring of osteoporosis treatment: a need for international reference standards", IOF-IFCC Bone Marker Standards Working Group. (2011). International Osteoporosis Foundation, 22(2), 391-420. doi:10.1007/s00198-010-1501-1.

Wang et al, "MiR-133a in Human Circulating Monocytes: A Potential Biomarker Associated with Postmenopausal Osteoporosis", PLoS One, vol. 7, No. 4, 2012, p. e34641.

Weilner et al, "Secretion of microvesicular miRNAs in cellular and organismal aging", (2013) Experimental Gerontology, 48(7), 626-633. doi:10.1016/5 j.exger.2012.11.017.

Zhao et al, "MicroRNAs regulate bone metabolism" (2013) J Bone Miner Metab. May 2014;32(3):221-31. doi: 10.1007/s00774-013-0537-7. Epub Dec. 6, 2013.

Extended European Search Report for 14172354.4 dated Jan. 26, 2015; 11 pages.

Search Report for PCT/EP15/63091 dated Dec. 14, 2015; 9 pages.

Written Opinion for PCT/EP15/63091 dated Dec. 14, 2015; 10 pages.

\* cited by examiner a b c d

SEQUENCE LISTING

```
<160> NUMBER OF SEQ ID NOS: 274

<210> SEQ ID NO 1
<211> LENGTH: 23
<212> TYPE: RNA
<213> ORGANISM: Homo sapiens
<220> FEATURE:
<223> OTHER INFORMATION: hsa-miR-10a-5p

<400> SEQUENCE: 1
uacccuguag auccgaauuu gug                                              23

<210> SEQ ID NO 2
<211> LENGTH: 23
<212> TYPE: RNA
<213> ORGANISM: Homo sapiens
<220> FEATURE:
<223> OTHER INFORMATION: hsa-miR-10b-5p

<400> SEQUENCE: 2
uacccuguag aaccgaauuu gug                                              23

<210> SEQ ID NO 3
<211> LENGTH: 23
<212> TYPE: RNA
<213> ORGANISM: Homo sapiens
<220> FEATURE:
<223> OTHER INFORMATION: hsa-miR-106a-5p

<400> SEQUENCE: 3
aaaagugcuu acagugcagg uag                                              23

<210> SEQ ID NO 4
<211> LENGTH: 22
<212> TYPE: RNA
<213> ORGANISM: Homo sapiens
<220> FEATURE:
<223> OTHER INFORMATION: hsa-miR-125b-5p

<400> SEQUENCE: 4
ucccugagac ccuaacuugu ga                                               22

<210> SEQ ID NO 5
<211> LENGTH: 22
<212> TYPE: RNA
<213> ORGANISM: Homo sapiens
<220> FEATURE:
```

<223> OTHER INFORMATION: hsa-miR-127-3p

<400> SEQUENCE: 5
ucggauccgu cugagcuugg cu                                            22

<210> SEQ ID NO 6
<211> LENGTH: 22
<212> TYPE: RNA
<213> ORGANISM: Homo sapiens
<220> FEATURE:
<223> OTHER INFORMATION: hsa-miR-133a-3p

<400> SEQUENCE: 6 uuugguccccc uucaaccagc ug                                           22

<210> SEQ ID NO 7
<211> LENGTH: 22
<212> TYPE: RNA
<213> ORGANISM: Homo sapiens
<220> FEATURE:
<223> OTHER INFORMATION: hsa-miR-133b

<400> SEQUENCE: 7 uuugguccccc uucaaccagc ua                                           22

<210> SEQ ID NO 8
<211> LENGTH: 21
<212> TYPE: RNA
<213> ORGANISM: Homo sapiens
<220> FEATURE:
<223> OTHER INFORMATION: hsa-miR-143-3p

<400> SEQUENCE: 8
ugagaugaag cacuguagcu c                                             21

<210> SEQ ID NO 9
<211> LENGTH: 23
<212> TYPE: RNA
<213> ORGANISM: Homo sapiens
<220> FEATURE:
<223> OTHER INFORMATION: hsa-miR-18a-3p

<400> SEQUENCE: 9
acugcccuaa gugcuccuuc ugg                                           23

<210> SEQ ID NO 10
<211> LENGTH: 22
<212> TYPE: RNA
<213> ORGANISM: Homo sapiens
<220> FEATURE:
<223> OTHER INFORMATION: hsa-miR-194-5p

<400> SEQUENCE: 10
uguaacagca acuccaugug ga                                            22

<210> SEQ ID NO 11
<211> LENGTH: 22
<212> TYPE: RNA
<213> ORGANISM: Homo sapiens
<220> FEATURE:
<223> OTHER INFORMATION: hsa-miR-30a-5p

<400> SEQUENCE: 11
uguaaacauc cucgacugga ag                                            22

```
<210> SEQ ID NO 12
<211> LENGTH: 22
<212> TYPE: RNA
<213> ORGANISM: Homo sapiens
<220> FEATURE:
<223> OTHER INFORMATION: hsa-miR-328-3p

<400> SEQUENCE: 12
cuggcccucu cugcccuucc gu                                                    22

<210> SEQ ID NO 13
<211> LENGTH: 21
<212> TYPE: RNA
<213> ORGANISM: Homo sapiens
<220> FEATURE:
<223> OTHER INFORMATION: hsa-miR-376a-3p

<400> SEQUENCE: 13
aucauagagg aaaauccacg u                                                     21

<210> SEQ ID NO 14
<211> LENGTH: 22
<212> TYPE: RNA
<213> ORGANISM: Homo sapiens
<220> FEATURE:
<223> OTHER INFORMATION: hsa-miR-409-3p

<400> SEQUENCE: 14
gaauguugcu cggugaaccc cu                                                    22

<210> SEQ ID NO 15
<211> LENGTH: 22
<212> TYPE: RNA
<213> ORGANISM: Homo sapiens
<220> FEATURE:
<223> OTHER INFORMATION: hsa-miR-574-3p

<400> SEQUENCE: 15
cacgcucaug cacacaccca ca                                                    22

<210> SEQ ID NO 16
<211> LENGTH: 110
<212> TYPE: RNA
<213> ORGANISM: Homo sapiens
<220> FEATURE:
<223> OTHER INFORMATION: hsa-mir-10a

<400> SEQUENCE: 16
gaucugucug ucuucuguau aucccuguag auccgaauu uguguaagga auuuguggu             60 cacaaauucg uaucuagggg aauauguagu ugacauaaac acuccgcucu                     110

<210> SEQ ID NO 17
<211> LENGTH: 110
<212> TYPE: RNA
<213> ORGANISM: Homo sapiens
<220> FEATURE:
<223> OTHER INFORMATION: hsa-mir-10b

<400> SEQUENCE: 17
ccagagguug uaacguuguc uauauauacc cuguagaacc gaauugugu gguauccgua            60 uagucacaga uucgauucua ggggaauaua uggucgaugc aaaaacuuca                     110

<210> SEQ ID NO 18
<211> LENGTH: 81
<212> TYPE: RNA
```

<213> ORGANISM: Homo sapiens
<220> FEATURE:
<223> OTHER INFORMATION: hsa-mir-106a

<400> SEQUENCE: 18
ccuuggccau guaaaagugc uuacagugca gguagcuuuu ugagaucuac ugcaauguaa    60
gcacuucuua cauuaccaug g                                              81

<210> SEQ ID NO 19
<211> LENGTH: 88
<212> TYPE: RNA
<213> ORGANISM: Homo sapiens
<220> FEATURE:
<223> OTHER INFORMATION: hsa-mir-125b-1

<400> SEQUENCE: 19
ugcgcuccuc ucagcccug agcccuaac uugugauguu uaccguuuaa auccacgggu    60
uaggcucuug ggagcugcga gucgugcu                                      88

<210> SEQ ID NO 20
<211> LENGTH: 97
<212> TYPE: RNA
<213> ORGANISM: Homo sapiens
<220> FEATURE:
<223> OTHER INFORMATION: hsa-mir-127

<400> SEQUENCE: 20
ugugaucacu gucuccagcc ugcugaagcu cagagggcuc ugauucagaa agaucaucgg    60
auccgucuga gcuuggcugg ucggaagucu caucauc                             97

<210> SEQ ID NO 21
<211> LENGTH: 88
<212> TYPE: RNA
<213> ORGANISM: Homo sapiens
<220> FEATURE:
<223> OTHER INFORMATION: hsa-mir-133a-1

<400> SEQUENCE: 21
acaaugcuuu gcuagagcug guaaaaugga accaaaucgc cucuucaaug gauuuggucc    60
ccuucaacca gcuguagcua ugcauuga                                      88

<210> SEQ ID NO 22
<211> LENGTH: 119
<212> TYPE: RNA
<213> ORGANISM: Homo sapiens
<220> FEATURE:
<223> OTHER INFORMATION: hsa-mir-133b

<400> SEQUENCE: 22
ccucagaaga aagaugcccc cugcucuggc uggucaaacg gaaccaaguc cgucuuccug    60
agagguuugg uccccuucaa ccagcuacag cagggcuggc aaugcccagu ccuuggaga   119

<210> SEQ ID NO 23
<211> LENGTH: 106
<212> TYPE: RNA
<213> ORGANISM: Homo sapiens
<220> FEATURE:
<223> OTHER INFORMATION: hsa-mir-143

<400> SEQUENCE: 23
gcgcagcgcc cugucuccca gccugaggug cagcugcca ucucugguca guugggaguc    60
ugagaugaag cacuguagcu caggaagaga gaaguuguuc ugcagc                 106

```
<210> SEQ ID NO 24
<211> LENGTH: 71
<212> TYPE: RNA
<213> ORGANISM: Homo sapiens
<220> FEATURE:
<223> OTHER INFORMATION: hsa-mir-18a

<400> SEQUENCE: 24
uguucuaagg ugcaucuagu gcagauagug aaguagauua gcaucuacug cccuaagugc    60
uccuucuggc a                                                         71

<210> SEQ ID NO 25
<211> LENGTH: 85
<212> TYPE: RNA
<213> ORGANISM: Homo sapiens
<220> FEATURE:
<223> OTHER INFORMATION: hsa-mir-194-1

<400> SEQUENCE: 25
augguguuau caaguguaac agcaacucca ugguggacugu guaccaauuu ccaguggaga    60
ugcuguuacu uuugaugguu accaa                                          85

<210> SEQ ID NO 26
<211> LENGTH: 71
<212> TYPE: RNA
<213> ORGANISM: Homo sapiens
<220> FEATURE:
<223> OTHER INFORMATION: hsa-mir-30a

<400> SEQUENCE: 26
gcgacuguaa acauccucga cuggaagcug ugaagccaca gaugggcuuu cagucggaug    60
uuugcagcug c                                                         71

<210> SEQ ID NO 27
<211> LENGTH: 75
<212> TYPE: RNA
<213> ORGANISM: Homo sapiens
<220> FEATURE:
<223> OTHER INFORMATION: hsa-mir-328

<400> SEQUENCE: 27 uggaguggggg gggcaggagg ggcucaggga gaaagugcau acagccccug gcccucucug    60
cccuuccguc cccug                                                     75

<210> SEQ ID NO 28
<211> LENGTH: 68
<212> TYPE: RNA
<213> ORGANISM: Homo sapiens
<220> FEATURE:
<223> OTHER INFORMATION: hsa-mir-376a-1

<400> SEQUENCE: 28
uaaaagguag auucuccuuc uaugaguaca uuauuuauga uuaaucauag aggaaaaucc    60
acguuuuc                                                             68

<210> SEQ ID NO 29
<211> LENGTH: 79
<212> TYPE: RNA
<213> ORGANISM: Homo sapiens
<220> FEATURE:
<223> OTHER INFORMATION: hsa-mir-409
```

```
<400> SEQUENCE: 29
ugguacucgg ggagagguua cccgagcaac uuugcaucug gacgacgaau guugcucggu    60
gaaccccuuu ucgguauca                                                79

<210> SEQ ID NO 30
<211> LENGTH: 96
<212> TYPE: RNA
<213> ORGANISM: Homo sapiens
<220> FEATURE:
<223> OTHER INFORMATION: hsa-mir-574

<400> SEQUENCE: 30
gggaccugcg uggguygcggg cgugugagug uguguguguc agugugugc gcucggguc     60 cacgcucaug cacacaccca cacgcccaca cucagg                             96

<210> SEQ ID NO 31
<211> LENGTH: 22
<212> TYPE: RNA
<213> ORGANISM: Homo sapiens
<220> FEATURE:
<223> OTHER INFORMATION: hsa-let-7i-3p

<400> SEQUENCE: 31
cugcgcaagc uacugccuug cu                                            22

<210> SEQ ID NO 32
<211> LENGTH: 20
<212> TYPE: RNA
<213> ORGANISM: Homo sapiens
<220> FEATURE:
<223> OTHER INFORMATION: hsa-miR-1227-3p

<400> SEQUENCE: 32
cgugccaccc uuuuccccag                                               20

<210> SEQ ID NO 33
<211> LENGTH: 22
<212> TYPE: RNA
<213> ORGANISM: Homo sapiens
<220> FEATURE:
<223> OTHER INFORMATION: hsa-miR-127-3p

<400> SEQUENCE: 33
ucggauccgu cugagcuugg cu                                            22

<210> SEQ ID NO 34
<211> LENGTH: 22
<212> TYPE: RNA
<213> ORGANISM: Homo sapiens
<220> FEATURE:
<223> OTHER INFORMATION: hsa-miR-133b

<400> SEQUENCE: 34 uuugguccccc uucaaccagc ua                                           22

<210> SEQ ID NO 35
<211> LENGTH: 23
<212> TYPE: RNA
<213> ORGANISM: Homo sapiens
<220> FEATURE:
<223> OTHER INFORMATION: hsa-miR-135a-5p

<400> SEQUENCE: 35
uauggcuuuu uauuccuaug uga                                           23
```

```
<210> SEQ ID NO 36
<211> LENGTH: 22
<212> TYPE: RNA
<213> ORGANISM: Homo sapiens
<220> FEATURE:
<223> OTHER INFORMATION: hsa-miR-136-3p

<400> SEQUENCE: 36
caucaucguc ucaaaugagu cu                                              22

<210> SEQ ID NO 37
<211> LENGTH: 21
<212> TYPE: RNA
<213> ORGANISM: Homo sapiens
<220> FEATURE:
<223> OTHER INFORMATION: hsa-miR-143-3p

<400> SEQUENCE: 37
ugagaugaag cacuguagcu c                                               21

<210> SEQ ID NO 38
<211> LENGTH: 23
<212> TYPE: RNA
<213> ORGANISM: Homo sapiens
<220> FEATURE:
<223> OTHER INFORMATION: hsa-miR-155-5p

<400> SEQUENCE: 38
uuaaugcuaa ucgugauagg ggu                                             23

<210> SEQ ID NO 39
<211> LENGTH: 22
<212> TYPE: RNA
<213> ORGANISM: Homo sapiens
<220> FEATURE:
<223> OTHER INFORMATION: hsa-miR-181a-3p

<400> SEQUENCE: 39
accaucgacc guugauugua cc                                              22

<210> SEQ ID NO 40
<211> LENGTH: 21
<212> TYPE: RNA
<213> ORGANISM: Homo sapiens
<220> FEATURE:
<223> OTHER INFORMATION: hsa-miR-188-3p

<400> SEQUENCE: 40
cucccacaug caggguuugc a                                               21

<210> SEQ ID NO 41
<211> LENGTH: 21
<212> TYPE: RNA
<213> ORGANISM: Homo sapiens
<220> FEATURE:
<223> OTHER INFORMATION: hsa-miR-1908-5p

<400> SEQUENCE: 41
cggcggggac ggcgauuggu c                                               21

<210> SEQ ID NO 42
<211> LENGTH: 22
<212> TYPE: RNA
<213> ORGANISM: Homo sapiens
<220> FEATURE:
```

```
<223> OTHER INFORMATION: hsa-miR-190a-5p

<400> SEQUENCE: 42
ugauauguuu gauauauuag gu                                            22

<210> SEQ ID NO 43
<211> LENGTH: 21
<212> TYPE: RNA
<213> ORGANISM: Homo sapiens
<220> FEATURE:
<223> OTHER INFORMATION: hsa-miR-192-5p

<400> SEQUENCE: 43
cugaccuaug aauugacagc c                                             21

<210> SEQ ID NO 44
<211> LENGTH: 22
<212> TYPE: RNA
<213> ORGANISM: Homo sapiens
<220> FEATURE:
<223> OTHER INFORMATION: hsa-miR-193b-3p

<400> SEQUENCE: 44
aacuggcccu caaagucccg cu                                            22

<210> SEQ ID NO 45
<211> LENGTH: 22
<212> TYPE: RNA
<213> ORGANISM: Homo sapiens
<220> FEATURE:
<223> OTHER INFORMATION: hsa-miR-196b-5p

<400> SEQUENCE: 45
uagguaguuu ccuguuguug gg                                            22

<210> SEQ ID NO 46
<211> LENGTH: 23
<212> TYPE: RNA
<213> ORGANISM: Homo sapiens
<220> FEATURE:
<223> OTHER INFORMATION: hsa-miR-199b-5p

<400> SEQUENCE: 46
cccaguguuu agacuaucug uuc                                           23

<210> SEQ ID NO 47
<211> LENGTH: 22
<212> TYPE: RNA
<213> ORGANISM: Homo sapiens
<220> FEATURE:
<223> OTHER INFORMATION: hsa-miR-200b-3p

<400> SEQUENCE: 47
uaauacugcc ugguaaugau ga                                            22

<210> SEQ ID NO 48
<211> LENGTH: 22
<212> TYPE: RNA
<213> ORGANISM: Homo sapiens
<220> FEATURE:
<223> OTHER INFORMATION: hsa-miR-203a

<400> SEQUENCE: 48
gugaaauguu uaggaccacu ag                                            22
```

```
<210> SEQ ID NO 49
<211> LENGTH: 22
<212> TYPE: RNA
<213> ORGANISM: Homo sapiens
<220> FEATURE:
<223> OTHER INFORMATION: hsa-miR-205-5p

<400> SEQUENCE: 49
uccuucauuc caccggaguc ug                                                  22

<210> SEQ ID NO 50
<211> LENGTH: 23
<212> TYPE: RNA
<213> ORGANISM: Homo sapiens
<220> FEATURE:
<223> OTHER INFORMATION: hsa-miR-20b-5p

<400> SEQUENCE: 50
caaagugcuc auagugcagg uag                                                 23

<210> SEQ ID NO 51
<211> LENGTH: 22
<212> TYPE: RNA
<213> ORGANISM: Homo sapiens
<220> FEATURE:
<223> OTHER INFORMATION: hsa-miR-214-3p

<400> SEQUENCE: 51
acagcaggca cagacaggca gu                                                  22

<210> SEQ ID NO 52
<211> LENGTH: 21
<212> TYPE: RNA
<213> ORGANISM: Homo sapiens
<220> FEATURE:
<223> OTHER INFORMATION: hsa-miR-215-5p

<400> SEQUENCE: 52
augaccuaug aauugacaga c                                                   21

<210> SEQ ID NO 53
<211> LENGTH: 22
<212> TYPE: RNA
<213> ORGANISM: Homo sapiens
<220> FEATURE:
<223> OTHER INFORMATION: hsa-miR-223-5p

<400> SEQUENCE: 53
cguguauuug acaagcugag uu                                                  22

<210> SEQ ID NO 54
<211> LENGTH: 21
<212> TYPE: RNA
<213> ORGANISM: Homo sapiens
<220> FEATURE:
<223> OTHER INFORMATION: hsa-miR-27a-3p

<400> SEQUENCE: 54
uucacagugg cuaaguuccg c                                                   21

<210> SEQ ID NO 55
<211> LENGTH: 22
<212> TYPE: RNA
<213> ORGANISM: Homo sapiens
<220> FEATURE:
<223> OTHER INFORMATION: hsa-miR-30e-3p
```

```
<400> SEQUENCE: 55
cuuucagucg gauguuuaca gc                                           22

<210> SEQ ID NO 56
<211> LENGTH: 21
<212> TYPE: RNA
<213> ORGANISM: Homo sapiens
<220> FEATURE:
<223> OTHER INFORMATION: hsa-miR-323a-3p

<400> SEQUENCE: 56
cacauuacac ggucgaccuc u                                            21

<210> SEQ ID NO 57
<211> LENGTH: 23
<212> TYPE: RNA
<213> ORGANISM: Homo sapiens
<220> FEATURE:
<223> OTHER INFORMATION: hsa-miR-330-3p

<400> SEQUENCE: 57
gcaaagcaca cggccugcag aga                                          23

<210> SEQ ID NO 58
<211> LENGTH: 21
<212> TYPE: RNA
<213> ORGANISM: Homo sapiens
<220> FEATURE:
<223> OTHER INFORMATION: hsa-miR-342-5p

<400> SEQUENCE: 58
aggggugcua ucugugauug a                                            21

<210> SEQ ID NO 59
<211> LENGTH: 21
<212> TYPE: RNA
<213> ORGANISM: Homo sapiens
<220> FEATURE:
<223> OTHER INFORMATION: hsa-miR-369-3p

<400> SEQUENCE: 59
aauaauacau gguugaucuu u                                            21

<210> SEQ ID NO 60
<211> LENGTH: 21
<212> TYPE: RNA
<213> ORGANISM: Homo sapiens
<220> FEATURE:
<223> OTHER INFORMATION: hsa-miR-376c-3p

<400> SEQUENCE: 60
aacauagagg aaauuccacg u                                            21

<210> SEQ ID NO 61
<211> LENGTH: 22
<212> TYPE: RNA
<213> ORGANISM: Homo sapiens
<220> FEATURE:
<223> OTHER INFORMATION: hsa-miR-377-3p

<400> SEQUENCE: 61
aucacacaaa ggcaacuuuu gu                                           22

<210> SEQ ID NO 62
<211> LENGTH: 22
```

```
<212> TYPE: RNA
<213> ORGANISM: Homo sapiens
<220> FEATURE:
<223> OTHER INFORMATION: hsa-miR-378a-5p

<400> SEQUENCE: 62
cuccugacuc cagguccugu gu                                            22

<210> SEQ ID NO 63
<211> LENGTH: 21
<212> TYPE: RNA
<213> ORGANISM: Homo sapiens
<220> FEATURE:
<223> OTHER INFORMATION: hsa-miR-410-3p

<400> SEQUENCE: 63
aauauaacac agauggccug u                                             21

<210> SEQ ID NO 64
<211> LENGTH: 23
<212> TYPE: RNA
<213> ORGANISM: Homo sapiens
<220> FEATURE:
<223> OTHER INFORMATION: hsa-miR-454-3p

<400> SEQUENCE: 64
uagugcaaua uugcuuauag ggu                                           23

<210> SEQ ID NO 65
<211> LENGTH: 22
<212> TYPE: RNA
<213> ORGANISM: Homo sapiens
<220> FEATURE:
<223> OTHER INFORMATION: hsa-miR-487b-3p

<400> SEQUENCE: 65
aaucguacag ggucauccac uu                                            22

<210> SEQ ID NO 66
<211> LENGTH: 22
<212> TYPE: RNA
<213> ORGANISM: Homo sapiens
<220> FEATURE:
<223> OTHER INFORMATION: hsa-miR-495-3p

<400> SEQUENCE: 66
aaacaaacau ggugcacuuc uu                                            22

<210> SEQ ID NO 67
<211> LENGTH: 23
<212> TYPE: RNA
<213> ORGANISM: Homo sapiens
<220> FEATURE:
<223> OTHER INFORMATION: hsa-miR-500a-5p

<400> SEQUENCE: 67
uaauccuugc uaccugggug aga                                           23

<210> SEQ ID NO 68
<211> LENGTH: 21
<212> TYPE: RNA
<213> ORGANISM: Homo sapiens
<220> FEATURE:
<223> OTHER INFORMATION: hsa-miR-502-5p

<400> SEQUENCE: 68
```
auccuugcua ucugggugcu a                                             21

<210> SEQ ID NO 69
<211> LENGTH: 23
<212> TYPE: RNA
<213> ORGANISM: Homo sapiens
<220> FEATURE:
<223> OTHER INFORMATION: hsa-miR-542-5p

<400> SEQUENCE: 69
ucggggauca ucaugucacg aga                                           23

<210> SEQ ID NO 70
<211> LENGTH: 22
<212> TYPE: RNA
<213> ORGANISM: Homo sapiens
<220> FEATURE:
<223> OTHER INFORMATION: hsa-miR-548a-3p

<400> SEQUENCE: 70
caaaacuggc aauuacuuuu gc                                            22

<210> SEQ ID NO 71
<211> LENGTH: 23
<212> TYPE: RNA
<213> ORGANISM: Homo sapiens
<220> FEATURE:
<223> OTHER INFORMATION: hsa-miR-550a-5p

<400> SEQUENCE: 71
agugccugag ggaguaagag ccc                                           23

<210> SEQ ID NO 72
<211> LENGTH: 22
<212> TYPE: RNA
<213> ORGANISM: Homo sapiens
<220> FEATURE:
<223> OTHER INFORMATION: hsa-miR-576-3p

<400> SEQUENCE: 72
aagaugugga aaaauuggaa uc                                            22

<210> SEQ ID NO 73
<211> LENGTH: 22
<212> TYPE: RNA
<213> ORGANISM: Homo sapiens
<220> FEATURE:
<223> OTHER INFORMATION: hsa-miR-582-3p

<400> SEQUENCE: 73
uaacugguug aacaacugaa cc                                            22

<210> SEQ ID NO 74
<211> LENGTH: 22
<212> TYPE: RNA
<213> ORGANISM: Homo sapiens
<220> FEATURE:
<223> OTHER INFORMATION: hsa-miR-624-5p

<400> SEQUENCE: 74
uaguaccagu accuuguguu ca                                            22

<210> SEQ ID NO 75
<211> LENGTH: 22
<212> TYPE: RNA
<213> ORGANISM: Homo sapiens

```
<220> FEATURE:
<223> OTHER INFORMATION: hsa-miR-642a-5p

<400> SEQUENCE: 75
gucccucucc aaaugugucu ug                                            22

<210> SEQ ID NO 76
<211> LENGTH: 23
<212> TYPE: RNA
<213> ORGANISM: Homo sapiens
<220> FEATURE:
<223> OTHER INFORMATION: hsa-miR-941

<400> SEQUENCE: 76
cacccggcug ugugcacaug ugc                                           23

<210> SEQ ID NO 77
<211> LENGTH: 22
<212> TYPE: RNA
<213> ORGANISM: Homo sapiens
<220> FEATURE:
<223> OTHER INFORMATION: hsa-miR-942-5p

<400> SEQUENCE: 77
ucuucucugu uuuggccaug ug                                            22

<210> SEQ ID NO 78
<211> LENGTH: 84
<212> TYPE: RNA
<213> ORGANISM: Homo sapiens
<220> FEATURE:
<223> OTHER INFORMATION: hsa-let-7i

<400> SEQUENCE: 78
cuggcugagg uaguaguuug ugcuguuggu cggguuguga cauugcccgc uggagaua     60 acugcgcaag cuacugccuu gcua                                          84

<210> SEQ ID NO 79
<211> LENGTH: 88
<212> TYPE: RNA
<213> ORGANISM: Homo sapiens
<220> FEATURE:
<223> OTHER INFORMATION: hsa-mir-1227

<400> SEQUENCE: 79
guggggccag gcgguggugg gcacugcugg gguggcaca gcagccaugc agagcgggca   60
uuugaccccg ugccacccuu uuccccag                                     88

<210> SEQ ID NO 80
<211> LENGTH: 97
<212> TYPE: RNA
<213> ORGANISM: Homo sapiens
<220> FEATURE:
<223> OTHER INFORMATION: hsa-mir-127

<400> SEQUENCE: 80
ugugaucacu gucuccagcc ugcugaagcu cagagggcuc ugauucagaa agaucaucgg   60
auccgucuga gcuuggcugg ucggaagucu caucauc                            97

<210> SEQ ID NO 81
<211> LENGTH: 119
<212> TYPE: RNA
<213> ORGANISM: Homo sapiens
<220> FEATURE:
```

<223> OTHER INFORMATION: hsa-mir-133b

<400> SEQUENCE: 81
ccucagaaga aagaugcccc cugcucuggc uggucaaacg gaaccaaguc cgucuuccug    60
agagguuugg uccccuucaa ccagcuacag cagggcuggc aaugcccagu ccuuggaga    119

<210> SEQ ID NO 82
<211> LENGTH: 90
<212> TYPE: RNA
<213> ORGANISM: Homo sapiens
<220> FEATURE:
<223> OTHER INFORMATION: hsa-mir-135a-1

<400> SEQUENCE: 82
aggccucgcu guucucuaug gcuuuuuauu ccuaugugau ucuacugcuc acucauauag    60
ggauuggagc cguggcgcac ggcgggaca                                      90

<210> SEQ ID NO 83
<211> LENGTH: 82
<212> TYPE: RNA
<213> ORGANISM: Homo sapiens
<220> FEATURE:
<223> OTHER INFORMATION: hsa-mir-136

<400> SEQUENCE: 83
ugagcccucg gaggacucca uuuguuuuga ugauggauuc uuaugcucca ucaucgucuc    60
aaaugagucu ucagagggu cu                                              82

<210> SEQ ID NO 84
<211> LENGTH: 106
<212> TYPE: RNA
<213> ORGANISM: Homo sapiens
<220> FEATURE:
<223> OTHER INFORMATION: hsa-mir-143

<400> SEQUENCE: 84
gcgcagcgcc cugucuccca gccugaggug cagugcugca ucucggucca guugggaguc    60
ugagaugaag cacuguagcu caggaagaga gaaguuguuc ugcagc                   106

<210> SEQ ID NO 85
<211> LENGTH: 65
<212> TYPE: RNA
<213> ORGANISM: Homo sapiens
<220> FEATURE:
<223> OTHER INFORMATION: hsa-mir-155

<400> SEQUENCE: 85
cuguuaaugc uaaucgugau aggggu uuuu gccuccaacu gacuccuaca uauuagcauu    60
aacag                                                                65

<210> SEQ ID NO 86
<211> LENGTH: 110
<212> TYPE: RNA
<213> ORGANISM: Homo sapiens
<220> FEATURE:
<223> OTHER INFORMATION: hsa-mir-181a-1

<400> SEQUENCE: 86
ugaguuuuga gguugcuuca gugaacauuc aacgcugucg gugaguuugg aauuaaaauc    60
aaaaccaucg accguugauu guacccuaug gcuaaccauc aucuacucca              110

```
<210> SEQ ID NO 87
<211> LENGTH: 86
<212> TYPE: RNA
<213> ORGANISM: Homo sapiens
<220> FEATURE:
<223> OTHER INFORMATION: hsa-mir-188

<400> SEQUENCE: 87
ugcucccucu cucacauccc uugcauggug gagggugagc uuucugaaaa ccccucccac    60 augcagdgguu ugcaggaugg cgagcc                                       86

<210> SEQ ID NO 88
<211> LENGTH: 80
<212> TYPE: RNA
<213> ORGANISM: Homo sapiens
<220> FEATURE:
<223> OTHER INFORMATION: hsa-mir-1908

<400> SEQUENCE: 88
cgggaaugcc gcggcgggga cggcgauugg uccguaugug uggugccacc ggccgccggc    60
uccgccccgg ccccgcccc                                                80

<210> SEQ ID NO 89
<211> LENGTH: 85
<212> TYPE: RNA
<213> ORGANISM: Homo sapiens
<220> FEATURE:
<223> OTHER INFORMATION: hsa-mir-190a

<400> SEQUENCE: 89
ugcaggccuc ugugugauau guuugauaua uuagguuguu auuuaaucca acuauauauc    60
aaacauauuc cuacaguguc uugcc                                         85

<210> SEQ ID NO 90
<211> LENGTH: 110
<212> TYPE: RNA
<213> ORGANISM: Homo sapiens
<220> FEATURE:
<223> OTHER INFORMATION: hsa-mir-192

<400> SEQUENCE: 90
gccgagaccg agugcacagg gcucugaccu augaauugac agccagugcu cucgucuccc    60
cucuggcugc caauuccaua ggucacaggu auguucgccu caaugccagc              110

<210> SEQ ID NO 91
<211> LENGTH: 83
<212> TYPE: RNA
<213> ORGANISM: Homo sapiens
<220> FEATURE:
<223> OTHER INFORMATION: hsa-mir-193b

<400> SEQUENCE: 91
guggucucag aaucgggguu uuaggggcga gaugaguuua uguuuaucc aacuggcccu     60 caaagucccg cuuuuggggu cau                                           83

<210> SEQ ID NO 92
<211> LENGTH: 84
<212> TYPE: RNA
<213> ORGANISM: Homo sapiens
<220> FEATURE:
<223> OTHER INFORMATION: hsa-mir-196b

<400> SEQUENCE: 92
```

```
acuggucggu gauuuaggua guuuccuguu guugggaucc accuuucucu cgacagcacg    60
acacugccuu cauuacuuca guug                                          84
```

```
<210> SEQ ID NO 93
<211> LENGTH: 110
<212> TYPE: RNA
<213> ORGANISM: Homo sapiens
<220> FEATURE:
<223> OTHER INFORMATION: hsa-mir-199b

<400> SEQUENCE: 93
ccagaggaca ccuccacucc gucuacccag uguuuagacu aucguucag gacucccaaa    60 uuguacagua gucugcacau ugguuaggcu gggcugggu agacccucgg              110
```

```
<210> SEQ ID NO 94
<211> LENGTH: 95
<212> TYPE: RNA
<213> ORGANISM: Homo sapiens
<220> FEATURE:
<223> OTHER INFORMATION: hsa-mir-200b

<400> SEQUENCE: 94
ccagcucggg cagccguggc caucuuacug ggcagcauug gauggaguca ggucucuaau    60
acugccuggu aaugaugacg gcggagcccu gcacg                              95
```

```
<210> SEQ ID NO 95
<211> LENGTH: 110
<212> TYPE: RNA
<213> ORGANISM: Homo sapiens
<220> FEATURE:
<223> OTHER INFORMATION: hsa-mir-203a

<400> SEQUENCE: 95
guguugggga cucgcgcgcu gguccagug guucuuaaca guucaacagu ucuguagcgc    60
aauugugaaa uguuuaggac cacuagaccc ggcgggcgcg gcgacagcga             110
```

```
<210> SEQ ID NO 96
<211> LENGTH: 110
<212> TYPE: RNA
<213> ORGANISM: Homo sapiens
<220> FEATURE:
<223> OTHER INFORMATION: hsa-mir-205

<400> SEQUENCE: 96
aaagauccuc agacaaucca ugugcuucuc uugccuuca uuccaccgga gucugucuca    60
uacccaacca gauuucagug gagugaaguu caggaggcau ggagcugaca             110
```

```
<210> SEQ ID NO 97
<211> LENGTH: 69
<212> TYPE: RNA
<213> ORGANISM: Homo sapiens
<220> FEATURE:
<223> OTHER INFORMATION: hsa-mir-20b

<400> SEQUENCE: 97
aguaccaaag ugcucauagu gcagguaguu uuggcaugac ucuacuguag uaugggcacu    60
uccaguacu                                                           69
```

```
<210> SEQ ID NO 98
<211> LENGTH: 110
<212> TYPE: RNA
<213> ORGANISM: Homo sapiens
```

```
<220> FEATURE:
<223> OTHER INFORMATION: hsa-mir-214

<400> SEQUENCE: 98
ggccuggcug  gacagaguug  ucaugugucu  gccugucuac  acuugcugug  cagaacaucc    60
gcucaccugu  acagcaggca  cagacaggca  gucacaugac  aacccagccu              110

<210> SEQ ID NO 99
<211> LENGTH: 110
<212> TYPE: RNA
<213> ORGANISM: Homo sapiens
<220> FEATURE:
<223> OTHER INFORMATION: hsa-mir-215

<400> SEQUENCE: 99
aucauucaga  aaugguauac  aggaaaauga  ccuaugaauu  gacagacaau  auagcugagu    60
uugucuguca  uuucuuuagg  ccaauauucu  guaugacugu  gcuacuucaa              110

<210> SEQ ID NO 100
<211> LENGTH: 110
<212> TYPE: RNA
<213> ORGANISM: Homo sapiens
<220> FEATURE:
<223> OTHER INFORMATION: hsa-mir-223

<400> SEQUENCE: 100
ccuggccucc  ugcagugcca  cgcuccgugu  auuugacaag  cugaguugga  cacuccaugu    60
gguagagugu  caguuuguca  aauaccccaa  gugcggcaca  ugcuuaccag              110

<210> SEQ ID NO 101
<211> LENGTH: 78
<212> TYPE: RNA
<213> ORGANISM: Homo sapiens
<220> FEATURE:
<223> OTHER INFORMATION: hsa-mir-27a

<400> SEQUENCE: 101
cugaggagca  gggcuuagcu  gcuugugagc  agggucaca  ccaagucgug  uucacagugg     60
cuaaguuccg  cccccag                                                      78

<210> SEQ ID NO 102
<211> LENGTH: 92
<212> TYPE: RNA
<213> ORGANISM: Homo sapiens
<220> FEATURE:
<223> OTHER INFORMATION: hsa-mir-30e

<400> SEQUENCE: 102
gggcagucuu  ugcuacugua  aacauccuug  acuggaagcu  guaagguguu  cagaggagcu    60
uucagucgga  uguuuacagc  ggcaggcugc  ca                                   92

<210> SEQ ID NO 103
<211> LENGTH: 86
<212> TYPE: RNA
<213> ORGANISM: Homo sapiens
<220> FEATURE:
<223> OTHER INFORMATION: hsa-mir-323a

<400> SEQUENCE: 103
uugguacuug  gagagaggug  guccguggcg  cguucgcuuu  auuuauggcg  cacauuacac    60
ggucgaccuc  uuugcaguau  cuaauc                                           86
```

```
<210> SEQ ID NO 104
<211> LENGTH: 94
<212> TYPE: RNA
<213> ORGANISM: Homo sapiens
<220> FEATURE:
<223> OTHER INFORMATION: hsa-mir-330

<400> SEQUENCE: 104
cuuuggcgau cacugccucu cugggccugu gucuuaggcu cugcaagauc aaccgagcaa      60
agcacacggc cugcagagag gcagcgcucu gccc                                  94

<210> SEQ ID NO 105
<211> LENGTH: 99
<212> TYPE: RNA
<213> ORGANISM: Homo sapiens
<220> FEATURE:
<223> OTHER INFORMATION: hsa-mir-342

<400> SEQUENCE: 105
gaaacugggc ucaaggugag ggugcuauc ugugauugag ggacaugguu aauggaauug       60
ucucacacag aaaucgcacc cgucaccuug gccuacuua                             99

<210> SEQ ID NO 106
<211> LENGTH: 70
<212> TYPE: RNA
<213> ORGANISM: Homo sapiens
<220> FEATURE:
<223> OTHER INFORMATION: hsa-mir-369

<400> SEQUENCE: 106
uugaagggag aucgaccgug uuauauucgc uuuaugacu ucgaauaaua caugguugau       60
cuuuucucag                                                             70

<210> SEQ ID NO 107
<211> LENGTH: 66
<212> TYPE: RNA
<213> ORGANISM: Homo sapiens
<220> FEATURE:
<223> OTHER INFORMATION: hsa-mir-376c

<400> SEQUENCE: 107
aaaaggugga uauuccuucu auguuuaugu uauuuauggu uaaacauaga ggaaauucca      60
cguuuu                                                                 66

<210> SEQ ID NO 108
<211> LENGTH: 69
<212> TYPE: RNA
<213> ORGANISM: Homo sapiens
<220> FEATURE:
<223> OTHER INFORMATION: hsa-mir-377

<400> SEQUENCE: 108
uugagcagag guugcccuug gugaauucgc uuuauuuaug uugaaucaca caaaggcaac      60
uuuuguuug                                                              69

<210> SEQ ID NO 109
<211> LENGTH: 66
<212> TYPE: RNA
<213> ORGANISM: Homo sapiens
<220> FEATURE:
<223> OTHER INFORMATION: hsa-mir-378a

<400> SEQUENCE: 109
```

```
agggcuccug acuccagguc cugugguguua ccuagaaaua gcacuggacu uggagucaga    60
aggccu                                                               66

<210> SEQ ID NO 110
<211> LENGTH: 80
<212> TYPE: RNA
<213> ORGANISM: Homo sapiens
<220> FEATURE:
<223> OTHER INFORMATION: hsa-mir-410

<400> SEQUENCE: 110
gguaccugag aagagguugu cugugaugag uucgcuuuua uuaaugacga auauaacaca    60
gauggccugu uuucaguacc                                                80

<210> SEQ ID NO 111
<211> LENGTH: 115
<212> TYPE: RNA
<213> ORGANISM: Homo sapiens
<220> FEATURE:
<223> OTHER INFORMATION: hsa-mir-454

<400> SEQUENCE: 111
ucuguuuauc accagauccu agaaccccuau caauauugc ucugcugugu aaauaguucu    60
gaguagugca auauugcuua uaggguuuug uguuuggaa agaacaaugg gcagg         115

<210> SEQ ID NO 112
<211> LENGTH: 84
<212> TYPE: RNA
<213> ORGANISM: Homo sapiens
<220> FEATURE:
<223> OTHER INFORMATION: hsa-mir-487b

<400> SEQUENCE: 112
uugguacuug gagaguggu aucccugucc uguucguuuu gcucaugucg aaucguacag    60
ggucauccac uuuuucagua ucaa                                           84

<210> SEQ ID NO 113
<211> LENGTH: 82
<212> TYPE: RNA
<213> ORGANISM: Homo sapiens
<220> FEATURE:
<223> OTHER INFORMATION: hsa-mir-495

<400> SEQUENCE: 113
ugguaccuga aaagaaguug cccauguuau uuucgcuuua uaugugacga aacaaacaug    60
gugcacuucu uuuucgguau ca                                             82

<210> SEQ ID NO 114
<211> LENGTH: 84
<212> TYPE: RNA
<213> ORGANISM: Homo sapiens
<220> FEATURE:
<223> OTHER INFORMATION: hsa-mir-500a

<400> SEQUENCE: 114 gcuccccuc ucuaauccuu gcuaccuggg ugagagugcu gucugaaugc aaugcaccug    60
ggcaaggauu cugagagcga gagc                                           84

<210> SEQ ID NO 115
<211> LENGTH: 86
<212> TYPE: RNA
```

```
<213> ORGANISM: Homo sapiens
<220> FEATURE:
<223> OTHER INFORMATION: hsa-mir-502

<400> SEQUENCE: 115 ugcuccccu cucuaauccu ugcuaucugg gugcuagugc uggcucaaug caaugcaccu    60
gggcaaggau ucagagaggg ggagcu                                        86

<210> SEQ ID NO 116
<211> LENGTH: 97
<212> TYPE: RNA
<213> ORGANISM: Homo sapiens
<220> FEATURE:
<223> OTHER INFORMATION: hsa-mir-542

<400> SEQUENCE: 116
cagaucucag acaucucggg gaucaucaug ucacgagaua ccagugugca cuugugacag    60
auugauaacu gaaaggucug ggagccacuc aucuuca                             97

<210> SEQ ID NO 117
<211> LENGTH: 97
<212> TYPE: RNA
<213> ORGANISM: Homo sapiens
<220> FEATURE:
<223> OTHER INFORMATION: hsa-mir-548a-1

<400> SEQUENCE: 117
ugcagggagg uauuaaguug gugcaaaagu aauugugauu uugccauua aaaguaacga    60 caaaacuggc aauuacuuuu gcaccaaacc ugguauu                             97

<210> SEQ ID NO 118
<211> LENGTH: 97
<212> TYPE: RNA
<213> ORGANISM: Homo sapiens
<220> FEATURE:
<223> OTHER INFORMATION: hsa-mir-550a-1

<400> SEQUENCE: 118
ugaugcuuug cuggcuggug cagugccuga gggaguaaga gcccuguugu uguaagauag    60
ugucuuacuc ccucaggcac aucccaaca agucucu                              97

<210> SEQ ID NO 119
<211> LENGTH: 98
<212> TYPE: RNA
<213> ORGANISM: Homo sapiens
<220> FEATURE:
<223> OTHER INFORMATION: hsa-mir-576

<400> SEQUENCE: 119
uacaauccaa cgaggauucu aauuucucca cgucuuuggu aauaagguuu ggcaaagaug    60
uggaaaaauu ggaauccuca uucgauuggu uauaacca                            98

<210> SEQ ID NO 120
<211> LENGTH: 98
<212> TYPE: RNA
<213> ORGANISM: Homo sapiens
<220> FEATURE:
<223> OTHER INFORMATION: hsa-mir-582

<400> SEQUENCE: 120
aucugugcuc uuugauuaca guuguucaac caguuacuaa ucuaacuaau uguaacuggu    60
ugaacaacug aacccaaagg gugcaaagua gaaacauu                            98
```

<210> SEQ ID NO 121
<211> LENGTH: 97
<212> TYPE: RNA
<213> ORGANISM: Homo sapiens
<220> FEATURE:
<223> OTHER INFORMATION: hsa-mir-624

<400> SEQUENCE: 121
aaugcuguuu caagguagua ccaguaccuu guguucagug gaaccaaggu aaacacaagg    60
uauugguauu accuugagau agcauuacac cuaagug                            97

<210> SEQ ID NO 122
<211> LENGTH: 97
<212> TYPE: RNA
<213> ORGANISM: Homo sapiens
<220> FEATURE:
<223> OTHER INFORMATION: hsa-mir-642a

<400> SEQUENCE: 122
aucugaguug ggagggucc ucuccaaaug ugucuugggg uggggauca agacacauuu     60 ggagagggaa ccucccaacu cggccucugc caucauu                            97

<210> SEQ ID NO 123
<211> LENGTH: 72
<212> TYPE: RNA
<213> ORGANISM: Homo sapiens
<220> FEATURE:
<223> OTHER INFORMATION: hsa-mir-941-1

<400> SEQUENCE: 123
uguggacaug ugcccagggc ccgggacagc gccacggaag aggacgcacc cggcugugug    60
cacaugugcc ca                                                      72

<210> SEQ ID NO 124
<211> LENGTH: 86
<212> TYPE: RNA
<213> ORGANISM: Homo sapiens
<220> FEATURE:
<223> OTHER INFORMATION: hsa-mir-942

<400> SEQUENCE: 124
auuaggagag uaucuucucu guuuuggcca uguguguacu cacagcccu cacacauggc    60 cgaaacagag aaguuacuuu ccuaau                                        86

<210> SEQ ID NO 125
<211> LENGTH: 22
<212> TYPE: RNA
<213> ORGANISM: Homo sapiens
<220> FEATURE:
<223> OTHER INFORMATION: hsa-let-7b-5p

<400> SEQUENCE: 125
ugagguagua gguugugugg uu                                           22

<210> SEQ ID NO 126
<211> LENGTH: 22
<212> TYPE: RNA
<213> ORGANISM: Homo sapiens
<220> FEATURE:
<223> OTHER INFORMATION: hsa-let-7g-5p

<400> SEQUENCE: 126
ugagguagua guuuguacag uu					22

<210> SEQ ID NO 127
<211> LENGTH: 22
<212> TYPE: RNA
<213> ORGANISM: Homo sapiens
<220> FEATURE:
<223> OTHER INFORMATION: hsa-let-7i-5p

<400> SEQUENCE: 127
ugagguagua guuugugcug uu					22

<210> SEQ ID NO 128
<211> LENGTH: 23
<212> TYPE: RNA
<213> ORGANISM: Homo sapiens
<220> FEATURE:
<223> OTHER INFORMATION: hsa-miR-106a-5p

<400> SEQUENCE: 128
aaaagugcuu acagugcagg uag					23

<210> SEQ ID NO 129
<211> LENGTH: 21
<212> TYPE: RNA
<213> ORGANISM: Homo sapiens
<220> FEATURE:
<223> OTHER INFORMATION: hsa-miR-106b-5p

<400> SEQUENCE: 129
uaaagugcug acagugcaga u						21

<210> SEQ ID NO 130
<211> LENGTH: 22
<212> TYPE: RNA
<213> ORGANISM: Homo sapiens
<220> FEATURE:
<223> OTHER INFORMATION: hsa-miR-127-3p

<400> SEQUENCE: 130
ucggauccgu cugagcuugg cu					22

<210> SEQ ID NO 131
<211> LENGTH: 22
<212> TYPE: RNA
<213> ORGANISM: Homo sapiens
<220> FEATURE:
<223> OTHER INFORMATION: hsa-miR-132-3p

<400> SEQUENCE: 131
uaacagucua cagccauggu cg					22

<210> SEQ ID NO 132
<211> LENGTH: 21
<212> TYPE: RNA
<213> ORGANISM: Homo sapiens
<220> FEATURE:
<223> OTHER INFORMATION: hsa-miR-140-3p

<400> SEQUENCE: 132
uaccacaggg uagaaccacg g						21

<210> SEQ ID NO 133
<211> LENGTH: 22
<212> TYPE: RNA
<213> ORGANISM: Homo sapiens

```
<220> FEATURE:
<223> OTHER INFORMATION: hsa-miR-141-3p

<400> SEQUENCE: 133
uaacacuguc ugguaaagau gg                                          22

<210> SEQ ID NO 134
<211> LENGTH: 21
<212> TYPE: RNA
<213> ORGANISM: Homo sapiens
<220> FEATURE:
<223> OTHER INFORMATION: hsa-miR-143-3p

<400> SEQUENCE: 134
ugagaugaag cacguagcu c                                            21

<210> SEQ ID NO 135
<211> LENGTH: 22
<212> TYPE: RNA
<213> ORGANISM: Homo sapiens
<220> FEATURE:
<223> OTHER INFORMATION: hsa-miR-143-5p

<400> SEQUENCE: 135
ggugcagugc ugcaucucug gu                                          22

<210> SEQ ID NO 136
<211> LENGTH: 20
<212> TYPE: RNA
<213> ORGANISM: Homo sapiens
<220> FEATURE:
<223> OTHER INFORMATION: hsa-miR-144-3p

<400> SEQUENCE: 136
uacaguauag augauguacu                                             20

<210> SEQ ID NO 137
<211> LENGTH: 22
<212> TYPE: RNA
<213> ORGANISM: Homo sapiens
<220> FEATURE:
<223> OTHER INFORMATION: hsa-miR-146b-5p

<400> SEQUENCE: 137
ugagaacuga auuccauagg cu                                          22

<210> SEQ ID NO 138
<211> LENGTH: 22
<212> TYPE: RNA
<213> ORGANISM: Homo sapiens
<220> FEATURE:
<223> OTHER INFORMATION: hsa-miR-154-5p

<400> SEQUENCE: 138
uagguuaucc guguugccuu cg                                          22

<210> SEQ ID NO 139
<211> LENGTH: 22
<212> TYPE: RNA
<213> ORGANISM: Homo sapiens
<220> FEATURE:
<223> OTHER INFORMATION: hsa-miR-16-2-3p

<400> SEQUENCE: 139
ccaauauuac ugugcugcuu ua                                          22
```

```
<210> SEQ ID NO 140
<211> LENGTH: 22
<212> TYPE: RNA
<213> ORGANISM: Homo sapiens
<220> FEATURE:
<223> OTHER INFORMATION: hsa-miR-16-5p

<400> SEQUENCE: 140
uagcagcacg uaaauauugg cg                                              22

<210> SEQ ID NO 141
<211> LENGTH: 23
<212> TYPE: RNA
<213> ORGANISM: Homo sapiens
<220> FEATURE:
<223> OTHER INFORMATION: hsa-miR-17-5p

<400> SEQUENCE: 141
caaagugcuu acagugcagg uag                                             23

<210> SEQ ID NO 142
<211> LENGTH: 23
<212> TYPE: RNA
<213> ORGANISM: Homo sapiens
<220> FEATURE:
<223> OTHER INFORMATION: hsa-miR-181b-5p

<400> SEQUENCE: 142
aacauucauu gcugucggug ggu                                             23

<210> SEQ ID NO 143
<211> LENGTH: 22
<212> TYPE: RNA
<213> ORGANISM: Homo sapiens
<220> FEATURE:
<223> OTHER INFORMATION: hsa-miR-181c-3p

<400> SEQUENCE: 143
aaccaucgac cguugagugg ac                                              22

<210> SEQ ID NO 144
<211> LENGTH: 22
<212> TYPE: RNA
<213> ORGANISM: Homo sapiens
<220> FEATURE:
<223> OTHER INFORMATION: hsa-miR-181c-5p

<400> SEQUENCE: 144
aacauucaac cgucggguga gu                                              22

<210> SEQ ID NO 145
<211> LENGTH: 22
<212> TYPE: RNA
<213> ORGANISM: Homo sapiens
<220> FEATURE:
<223> OTHER INFORMATION: hsa-miR-185-5p

<400> SEQUENCE: 145
uggagagaaa ggcaguuccu ga                                              22

<210> SEQ ID NO 146
<211> LENGTH: 23
<212> TYPE: RNA
<213> ORGANISM: Homo sapiens
<220> FEATURE:
<223> OTHER INFORMATION: hsa-miR-18a-3p
```

```
<400> SEQUENCE: 146
acugcccuaa gugcuccuuc ugg                                          23

<210> SEQ ID NO 147
<211> LENGTH: 23
<212> TYPE: RNA
<213> ORGANISM: Homo sapiens
<220> FEATURE:
<223> OTHER INFORMATION: hsa-miR-18a-5p

<400> SEQUENCE: 147
uaaggugcau cuagugcaga uag                                          23

<210> SEQ ID NO 148
<211> LENGTH: 23
<212> TYPE: RNA
<213> ORGANISM: Homo sapiens
<220> FEATURE:
<223> OTHER INFORMATION: hsa-miR-18b-5p

<400> SEQUENCE: 148
uaaggugcau cuagugcagu uag                                          23

<210> SEQ ID NO 149
<211> LENGTH: 21
<212> TYPE: RNA
<213> ORGANISM: Homo sapiens
<220> FEATURE:
<223> OTHER INFORMATION: hsa-miR-1908-5p

<400> SEQUENCE: 149
cggcggggac ggcgauuggu c                                            21

<210> SEQ ID NO 150
<211> LENGTH: 23
<212> TYPE: RNA
<213> ORGANISM: Homo sapiens
<220> FEATURE:
<223> OTHER INFORMATION: hsa-miR-191-5p

<400> SEQUENCE: 150
caacggaauc ccaaaagcag cug                                          23

<210> SEQ ID NO 151
<211> LENGTH: 22
<212> TYPE: RNA
<213> ORGANISM: Homo sapiens
<220> FEATURE:
<223> OTHER INFORMATION: hsa-miR-196b-5p

<400> SEQUENCE: 151
uagguaguuu ccuguuguug gg                                           22

<210> SEQ ID NO 152
<211> LENGTH: 23
<212> TYPE: RNA
<213> ORGANISM: Homo sapiens
<220> FEATURE:
<223> OTHER INFORMATION: hsa-miR-199b-5p

<400> SEQUENCE: 152
cccaguguuu agacuaucug uuc                                          23

<210> SEQ ID NO 153
```

```
<211> LENGTH: 23
<212> TYPE: RNA
<213> ORGANISM: Homo sapiens
<220> FEATURE:
<223> OTHER INFORMATION: hsa-miR-19b-1-5p

<400> SEQUENCE: 153
aguuuugcag guuugcaucc agc                                              23

<210> SEQ ID NO 154
<211> LENGTH: 23
<212> TYPE: RNA
<213> ORGANISM: Homo sapiens
<220> FEATURE:
<223> OTHER INFORMATION: hsa-miR-19b-3p

<400> SEQUENCE: 154
ugugcaaauc caugcaaaac uga                                              23

<210> SEQ ID NO 155
<211> LENGTH: 22
<212> TYPE: RNA
<213> ORGANISM: Homo sapiens
<220> FEATURE:
<223> OTHER INFORMATION: hsa-miR-200b-3p

<400> SEQUENCE: 155
uaauacugcc ugguaaugau ga                                               22

<210> SEQ ID NO 156
<211> LENGTH: 22
<212> TYPE: RNA
<213> ORGANISM: Homo sapiens
<220> FEATURE:
<223> OTHER INFORMATION: hsa-miR-203a

<400> SEQUENCE: 156
gugaaauguu uaggaccacu ag                                               22

<210> SEQ ID NO 157
<211> LENGTH: 23
<212> TYPE: RNA
<213> ORGANISM: Homo sapiens
<220> FEATURE:
<223> OTHER INFORMATION: hsa-miR-20a-5p

<400> SEQUENCE: 157
uaaagugcuu auagugcagg uag                                              23

<210> SEQ ID NO 158
<211> LENGTH: 23
<212> TYPE: RNA
<213> ORGANISM: Homo sapiens
<220> FEATURE:
<223> OTHER INFORMATION: hsa-miR-20b-5p

<400> SEQUENCE: 158
caaagugcuc auagugcagg uag                                              23

<210> SEQ ID NO 159
<211> LENGTH: 22
<212> TYPE: RNA
<213> ORGANISM: Homo sapiens
<220> FEATURE:
<223> OTHER INFORMATION: hsa-miR-210-3p

<400> SEQUENCE: 159
```
cugugcgugu gacagcggcu ga                                              22

<210> SEQ ID NO 160
<211> LENGTH: 21
<212> TYPE: RNA
<213> ORGANISM: Homo sapiens
<220> FEATURE:
<223> OTHER INFORMATION: hsa-miR-21-3p

<400> SEQUENCE: 160
caacaccagu cgaugggcug u                                               21

<210> SEQ ID NO 161
<211> LENGTH: 22
<212> TYPE: RNA
<213> ORGANISM: Homo sapiens
<220> FEATURE:
<223> OTHER INFORMATION: hsa-miR-25-3p

<400> SEQUENCE: 161
cauugcacuu gucucggucu ga                                              22

<210> SEQ ID NO 162
<211> LENGTH: 21
<212> TYPE: RNA
<213> ORGANISM: Homo sapiens
<220> FEATURE:
<223> OTHER INFORMATION: hsa-miR-26b-5p

<400> SEQUENCE: 162
uucaaguaau ucaggauagg u                                               21

<210> SEQ ID NO 163
<211> LENGTH: 23
<212> TYPE: RNA
<213> ORGANISM: Homo sapiens
<220> FEATURE:
<223> OTHER INFORMATION: hsa-miR-301a-3p

<400> SEQUENCE: 163
cagugcaaua guauugucaa agc                                             23

<210> SEQ ID NO 164
<211> LENGTH: 23
<212> TYPE: RNA
<213> ORGANISM: Homo sapiens
<220> FEATURE:
<223> OTHER INFORMATION: hsa-miR-301b

<400> SEQUENCE: 164
cagugcaaug auauugucaa agc                                             23

<210> SEQ ID NO 165
<211> LENGTH: 21
<212> TYPE: RNA
<213> ORGANISM: Homo sapiens
<220> FEATURE:
<223> OTHER INFORMATION: hsa-miR-323a-3p

<400> SEQUENCE: 165
cacauuacac ggucgaccuc u                                               21

<210> SEQ ID NO 166
<211> LENGTH: 23
<212> TYPE: RNA

```
<213> ORGANISM: Homo sapiens
<220> FEATURE:
<223> OTHER INFORMATION: hsa-miR-324-5p

<400> SEQUENCE: 166
cgcauccccu agggcauugg ugu                                              23

<210> SEQ ID NO 167
<211> LENGTH: 23
<212> TYPE: RNA
<213> ORGANISM: Homo sapiens
<220> FEATURE:
<223> OTHER INFORMATION: hsa-miR-330-3p

<400> SEQUENCE: 167
gcaaagcaca cggccugcag aga                                              23

<210> SEQ ID NO 168
<211> LENGTH: 22
<212> TYPE: RNA
<213> ORGANISM: Homo sapiens
<220> FEATURE:
<223> OTHER INFORMATION: hsa-miR-363-3p

<400> SEQUENCE: 168
aauugcacgg uauccaucug ua                                               22

<210> SEQ ID NO 169
<211> LENGTH: 21
<212> TYPE: RNA
<213> ORGANISM: Homo sapiens
<220> FEATURE:
<223> OTHER INFORMATION: hsa-miR-369-3p

<400> SEQUENCE: 169
aauaauacau gguugaucuu u                                                21

<210> SEQ ID NO 170
<211> LENGTH: 22
<212> TYPE: RNA
<213> ORGANISM: Homo sapiens
<220> FEATURE:
<223> OTHER INFORMATION: hsa-miR-374a-5p

<400> SEQUENCE: 170
uuauaauaca accugauaag ug                                               22

<210> SEQ ID NO 171
<211> LENGTH: 22
<212> TYPE: RNA
<213> ORGANISM: Homo sapiens
<220> FEATURE:
<223> OTHER INFORMATION: hsa-miR-375

<400> SEQUENCE: 171
uuuguucguu cggcucgcgu ga                                               22

<210> SEQ ID NO 172
<211> LENGTH: 21
<212> TYPE: RNA
<213> ORGANISM: Homo sapiens
<220> FEATURE:
<223> OTHER INFORMATION: hsa-miR-376c-3p

<400> SEQUENCE: 172
aacauagagg aaauuccacg u                                                21
```

<210> SEQ ID NO 173
<211> LENGTH: 22
<212> TYPE: RNA
<213> ORGANISM: Homo sapiens
<220> FEATURE:
<223> OTHER INFORMATION: hsa-miR-378a-5p

<400> SEQUENCE: 173
cuccugacuc cagguccugu gu                                          22

<210> SEQ ID NO 174
<211> LENGTH: 22
<212> TYPE: RNA
<213> ORGANISM: Homo sapiens
<220> FEATURE:
<223> OTHER INFORMATION: hsa-miR-451a

<400> SEQUENCE: 174
aaaccguuac cauuacugag uu                                          22

<210> SEQ ID NO 175
<211> LENGTH: 23
<212> TYPE: RNA
<213> ORGANISM: Homo sapiens
<220> FEATURE:
<223> OTHER INFORMATION: hsa-miR-454-3p

<400> SEQUENCE: 175
uagugcaaua uugcuuauag ggu                                         23

<210> SEQ ID NO 176
<211> LENGTH: 21
<212> TYPE: RNA
<213> ORGANISM: Homo sapiens
<220> FEATURE:
<223> OTHER INFORMATION: hsa-miR-486-3p

<400> SEQUENCE: 176
cggggcagcu caguacagga u                                           21

<210> SEQ ID NO 177
<211> LENGTH: 22
<212> TYPE: RNA
<213> ORGANISM: Homo sapiens
<220> FEATURE:
<223> OTHER INFORMATION: hsa-miR-486-5p

<400> SEQUENCE: 177
uccuguacug agcugccccg ag                                          22

<210> SEQ ID NO 178
<211> LENGTH: 22
<212> TYPE: RNA
<213> ORGANISM: Homo sapiens
<220> FEATURE:
<223> OTHER INFORMATION: hsa-miR-493-5p

<400> SEQUENCE: 178
uuguacaugg uaggcuuuca uu                                          22

<210> SEQ ID NO 179
<211> LENGTH: 23
<212> TYPE: RNA
<213> ORGANISM: Homo sapiens
<220> FEATURE:

-continued

<223> OTHER INFORMATION: hsa-miR-500a-5p

<400> SEQUENCE: 179
uaauccuugc uaccugggug aga        23

<210> SEQ ID NO 180
<211> LENGTH: 22
<212> TYPE: RNA
<213> ORGANISM: Homo sapiens
<220> FEATURE:
<223> OTHER INFORMATION: hsa-miR-532-3p

<400> SEQUENCE: 180
ccucccacac ccaaggcuug ca        22

<210> SEQ ID NO 181
<211> LENGTH: 22
<212> TYPE: RNA
<213> ORGANISM: Homo sapiens
<220> FEATURE:
<223> OTHER INFORMATION: hsa-miR-545-3p

<400> SEQUENCE: 181
ucagcaaaca uuuauugugu gc        22

<210> SEQ ID NO 182
<211> LENGTH: 22
<212> TYPE: RNA
<213> ORGANISM: Homo sapiens
<220> FEATURE:
<223> OTHER INFORMATION: hsa-miR-550a-3p

<400> SEQUENCE: 182
ugucuuacuc ccucaggcac au        22

<210> SEQ ID NO 183
<211> LENGTH: 23
<212> TYPE: RNA
<213> ORGANISM: Homo sapiens
<220> FEATURE:
<223> OTHER INFORMATION: hsa-miR-550a-5p

<400> SEQUENCE: 183
agugccugag ggaguaagag ccc        23

<210> SEQ ID NO 184
<211> LENGTH: 22
<212> TYPE: RNA
<213> ORGANISM: Homo sapiens
<220> FEATURE:
<223> OTHER INFORMATION: hsa-miR-589-5p

<400> SEQUENCE: 184
ugagaaccac gucugcucug ag        22

<210> SEQ ID NO 185
<211> LENGTH: 21
<212> TYPE: RNA
<213> ORGANISM: Homo sapiens
<220> FEATURE:
<223> OTHER INFORMATION: hsa-miR-590-3p

<400> SEQUENCE: 185
uaauuuuaug uauaagcuag u        21

```
<210> SEQ ID NO 186
<211> LENGTH: 22
<212> TYPE: RNA
<213> ORGANISM: Homo sapiens
<220> FEATURE:
<223> OTHER INFORMATION: hsa-miR-598-3p

<400> SEQUENCE: 186
uacgucaucg uugucaucgu ca                                              22

<210> SEQ ID NO 187
<211> LENGTH: 22
<212> TYPE: RNA
<213> ORGANISM: Homo sapiens
<220> FEATURE:
<223> OTHER INFORMATION: hsa-miR-627-5p

<400> SEQUENCE: 187
gugagucucu aagaaaagag ga                                              22

<210> SEQ ID NO 188
<211> LENGTH: 21
<212> TYPE: RNA
<213> ORGANISM: Homo sapiens
<220> FEATURE:
<223> OTHER INFORMATION: hsa-miR-629-5p

<400> SEQUENCE: 188
uggguuuacg uugggagaac u                                               21

<210> SEQ ID NO 189
<211> LENGTH: 23
<212> TYPE: RNA
<213> ORGANISM: Homo sapiens
<220> FEATURE:
<223> OTHER INFORMATION: hsa-miR-7-5p

<400> SEQUENCE: 189
uggaagacua gugauuuugu ugu                                             23

<210> SEQ ID NO 190
<211> LENGTH: 22
<212> TYPE: RNA
<213> ORGANISM: Homo sapiens
<220> FEATURE:
<223> OTHER INFORMATION: hsa-miR-92a-3p

<400> SEQUENCE: 190
uauugcacuu gucccggccu gu                                              22

<210> SEQ ID NO 191
<211> LENGTH: 22
<212> TYPE: RNA
<213> ORGANISM: Homo sapiens
<220> FEATURE:
<223> OTHER INFORMATION: hsa-miR-93-3p

<400> SEQUENCE: 191
acugcugagc uagcacuucc cg                                              22

<210> SEQ ID NO 192
<211> LENGTH: 23
<212> TYPE: RNA
<213> ORGANISM: Homo sapiens
<220> FEATURE:
<223> OTHER INFORMATION: hsa-miR-93-5p
```

```
<400> SEQUENCE: 192
caaagugcug uucgugcagg uag                                              23

<210> SEQ ID NO 193
<211> LENGTH: 23
<212> TYPE: RNA
<213> ORGANISM: Homo sapiens
<220> FEATURE:
<223> OTHER INFORMATION: hsa-miR-941

<400> SEQUENCE: 193
cacccggcug ugugcacaug ugc                                              23

<210> SEQ ID NO 194
<211> LENGTH: 22
<212> TYPE: RNA
<213> ORGANISM: Homo sapiens
<220> FEATURE:
<223> OTHER INFORMATION: hsa-miR-942-5p

<400> SEQUENCE: 194
ucuucucugu uuuggccaug ug                                               22

<210> SEQ ID NO 195
<211> LENGTH: 23
<212> TYPE: RNA
<213> ORGANISM: Homo sapiens
<220> FEATURE:
<223> OTHER INFORMATION: hsa-miR-96-5p

<400> SEQUENCE: 195
uuuggcacua gcacauuuuu gcu                                              23

<210> SEQ ID NO 196
<211> LENGTH: 22
<212> TYPE: RNA
<213> ORGANISM: Homo sapiens
<220> FEATURE:
<223> OTHER INFORMATION: hsa-miR-98-5p

<400> SEQUENCE: 196
ugagguagua aguuguauug uu                                               22

<210> SEQ ID NO 197
<211> LENGTH: 83
<212> TYPE: RNA
<213> ORGANISM: Homo sapiens
<220> FEATURE:
<223> OTHER INFORMATION: hsa-let-7b

<400> SEQUENCE: 197
cggggugagg uaguagguug ugugguuuca gggcagugau guugcccuc ggaagauaac       60 uauacaaccu acugccuucc cug                                              83

<210> SEQ ID NO 198
<211> LENGTH: 84
<212> TYPE: RNA
<213> ORGANISM: Homo sapiens
<220> FEATURE:
<223> OTHER INFORMATION: hsa-let-7g

<400> SEQUENCE: 198
aggcugaggu aguaguuugu acaguuugag ggcuaugau accacccggu acaggagaua       60
acuguacagg ccacugccuu gcca                                             84
```

```
<210> SEQ ID NO 199
<211> LENGTH: 84
<212> TYPE: RNA
<213> ORGANISM: Homo sapiens
<220> FEATURE:
<223> OTHER INFORMATION: hsa-let-7i

<400> SEQUENCE: 199
cuggcugagg uaguaguuug ugcuguuggu cggguuguga cauugcccgc uguggagaua      60
acugcgcaag cuacugccuu gcua                                            84

<210> SEQ ID NO 200
<211> LENGTH: 81
<212> TYPE: RNA
<213> ORGANISM: Homo sapiens
<220> FEATURE:
<223> OTHER INFORMATION: hsa-mir-106a

<400> SEQUENCE: 200
ccuuggccau guaaaagugc uuacagugca gguagcuuuu ugagaucuac ugcaauguaa      60
gcacuucuua cauuaccaug g                                               81

<210> SEQ ID NO 201
<211> LENGTH: 82
<212> TYPE: RNA
<213> ORGANISM: Homo sapiens
<220> FEATURE:
<223> OTHER INFORMATION: hsa-mir-106b

<400> SEQUENCE: 201
ccugccgggg cuaaagugcu gacagugcag auaguggucc ucccgugcu accgcacugu       60 ggguacuugc ugcuccagca gg                                              82

<210> SEQ ID NO 202
<211> LENGTH: 97
<212> TYPE: RNA
<213> ORGANISM: Homo sapiens
<220> FEATURE:
<223> OTHER INFORMATION: hsa-mir-127

<400> SEQUENCE: 202
ugugaucacu gucuccagcc ugcugaagcu cagagggcuc ugauucagaa agaucaucgg      60
auccgucuga gcuuggcugg ucggaagucu caucauc                              97

<210> SEQ ID NO 203
<211> LENGTH: 101
<212> TYPE: RNA
<213> ORGANISM: Homo sapiens
<220> FEATURE:
<223> OTHER INFORMATION: hsa-mir-132

<400> SEQUENCE: 203 ccgccccgc gucuccaggg caaccguggc uuucgauugu acuguggga acuggaggua        60 acagucuaca gccauggucg ccccgcagca cgcccacgcg c                         101

<210> SEQ ID NO 204
<211> LENGTH: 100
<212> TYPE: RNA
<213> ORGANISM: Homo sapiens
<220> FEATURE:
<223> OTHER INFORMATION: hsa-mir-140
```

```
<400> SEQUENCE: 204
ugugucucuc ucugugUCCU gccaguggUU uuacccuaug guagguuacg ucaugcuguu    60
cuaccacagg guagaaccac ggacaggaua ccggggcacc                         100

<210> SEQ ID NO 205
<211> LENGTH: 95
<212> TYPE: RNA
<213> ORGANISM: Homo sapiens
<220> FEATURE:
<223> OTHER INFORMATION: hsa-mir-141

<400> SEQUENCE: 205
cggccggccc uggguccauc uuccaguaca guguuggaug gucuaauugu gaagcccua    60 acacugucug guaaagaugg cucccggguga gguuc                             95

<210> SEQ ID NO 206
<211> LENGTH: 106
<212> TYPE: RNA
<213> ORGANISM: Homo sapiens
<220> FEATURE:
<223> OTHER INFORMATION: hsa-mir-143

<400> SEQUENCE: 206
gcgcagcgcc cugucuccca gccugaggug cagugcugca ucucugguca guugggaguc    60
ugagaugaag cacuguagcu caggaagaga gaaguuguuc ugcagc                  106

<210> SEQ ID NO 207
<211> LENGTH: 106
<212> TYPE: RNA
<213> ORGANISM: Homo sapiens
<220> FEATURE:
<223> OTHER INFORMATION: hsa-mir-143

<400> SEQUENCE: 207
gcgcagcgcc cugucuccca gccugaggug cagugcugca ucucugguca guugggaguc    60
ugagaugaag cacuguagcu caggaagaga gaaguuguuc ugcagc                  106

<210> SEQ ID NO 208
<211> LENGTH: 86
<212> TYPE: RNA
<213> ORGANISM: Homo sapiens
<220> FEATURE:
<223> OTHER INFORMATION: hsa-mir-144

<400> SEQUENCE: 208
uggggcccug gcugggauau caucauauac uguaaguuug cgaugagaca cuacaguaua    60
gaugauguac uaguccgggc accccc                                         86

<210> SEQ ID NO 209
<211> LENGTH: 73
<212> TYPE: RNA
<213> ORGANISM: Homo sapiens
<220> FEATURE:
<223> OTHER INFORMATION: hsa-mir-146b

<400> SEQUENCE: 209
ccuggcacug agaacugaau uccauaggcu gugagcucua gcaaugcccu guggacucag    60
uucuggugcc cgg                                                       73

<210> SEQ ID NO 210
<211> LENGTH: 84
```

```
<212> TYPE: RNA
<213> ORGANISM: Homo sapiens
<220> FEATURE:
<223> OTHER INFORMATION: hsa-mir-154

<400> SEQUENCE: 210
gugguacuug aagauagguu auccguguug ccuucgcuuu auuugugacg aaucauacac    60
gguugaccua uuuucagua ccaa                                            84

<210> SEQ ID NO 211
<211> LENGTH: 81
<212> TYPE: RNA
<213> ORGANISM: Homo sapiens
<220> FEATURE:
<223> OTHER INFORMATION: hsa-mir-16-2

<400> SEQUENCE: 211
guuccacucu agcagcacgu aaauauuggc guagugaaau auauauuaaa caccaauauu    60
acugugcugc uuuaguguga c                                              81

<210> SEQ ID NO 212
<211> LENGTH: 89
<212> TYPE: RNA
<213> ORGANISM: Homo sapiens
<220> FEATURE:
<223> OTHER INFORMATION: hsa-mir-16-1

<400> SEQUENCE: 212
gucagcagug ccuuagcagc acguaaauau uggcguuaag auucuaaaau uaucuccagu    60
auuaacugug cugcugaagu aagguugac                                      89

<210> SEQ ID NO 213
<211> LENGTH: 84
<212> TYPE: RNA
<213> ORGANISM: Homo sapiens
<220> FEATURE:
<223> OTHER INFORMATION: hsa-mir-17

<400> SEQUENCE: 213
gucagaauaa ugucaaagug cuuacagugc agguagugau augugcaucu acugcaguga    60
aggcacuugu agcauuaugg ugac                                           84

<210> SEQ ID NO 214
<211> LENGTH: 110
<212> TYPE: RNA
<213> ORGANISM: Homo sapiens
<220> FEATURE:
<223> OTHER INFORMATION: hsa-mir-181b-1

<400> SEQUENCE: 214
ccugugcaga gauuauuuuu uaaaagguca caaucaacau ucauugcugu cgguggguug    60
aacugugugg acaagcucac ugaacaauga augcaacugu ggccccgcuu               110

<210> SEQ ID NO 215
<211> LENGTH: 110
<212> TYPE: RNA
<213> ORGANISM: Homo sapiens
<220> FEATURE:
<223> OTHER INFORMATION: hsa-mir-181c

<400> SEQUENCE: 215
cggaaaauuu gccaaggguu uggggaaca uucaaccugu cggugaguuu gggcagcuca     60
```
ggcaaaccau cgaccguuga guggacccug aggccuggaa uugccauccu    110

<210> SEQ ID NO 216
<211> LENGTH: 110
<212> TYPE: RNA
<213> ORGANISM: Homo sapiens
<220> FEATURE:
<223> OTHER INFORMATION: hsa-mir-181c

<400> SEQUENCE: 216
cggaaaauuu gccaagggcuu uggggaaca uucaaccugu cggugaguuu gggcagcuca    60
ggcaaaccau cgaccguuga guggacccug aggccuggaa uugccauccu    110

<210> SEQ ID NO 217
<211> LENGTH: 82
<212> TYPE: RNA
<213> ORGANISM: Homo sapiens
<220> FEATURE:
<223> OTHER INFORMATION: hsa-mir-185

<400> SEQUENCE: 217 aggggggcgag ggauuggaga gaaaggcagu uccugauggu ccccucccca ggggcuggcu    60
uuccucuggu ccuucccucc ca    82

<210> SEQ ID NO 218
<211> LENGTH: 71
<212> TYPE: RNA
<213> ORGANISM: Homo sapiens
<220> FEATURE:
<223> OTHER INFORMATION: hsa-mir-18a

<400> SEQUENCE: 218
uguucuaagg ugcaucuagu gcagauagug aaguagauua gcaucuacug cccuaagugc    60
uccuucuggc a    71

<210> SEQ ID NO 219
<211> LENGTH: 71
<212> TYPE: RNA
<213> ORGANISM: Homo sapiens
<220> FEATURE:
<223> OTHER INFORMATION: hsa-mir-18a

<400> SEQUENCE: 219
uguucuaagg ugcaucuagu gcagauagug aaguagauua gcaucuacug cccuaagugc    60
uccuucuggc a    71

<210> SEQ ID NO 220
<211> LENGTH: 71
<212> TYPE: RNA
<213> ORGANISM: Homo sapiens
<220> FEATURE:
<223> OTHER INFORMATION: hsa-mir-18b

<400> SEQUENCE: 220
uguguuaagg ugcaucuagu gcaguuagug aagcagcuua gaaucuacug cccuaaaugc    60
cccuucuggc a    71

<210> SEQ ID NO 221
<211> LENGTH: 80
<212> TYPE: RNA
<213> ORGANISM: Homo sapiens
<220> FEATURE:
<223> OTHER INFORMATION: hsa-mir-1908

<400> SEQUENCE: 221
cgggaaugcc gcggcgggga cggcgauugg uccguaugug uggugccacc ggccgccggc    60
uccgccccgg ccccgcccc                                                80

<210> SEQ ID NO 222
<211> LENGTH: 92
<212> TYPE: RNA
<213> ORGANISM: Homo sapiens
<220> FEATURE:
<223> OTHER INFORMATION: hsa-mir-191

<400> SEQUENCE: 222
cggcuggaca gcgggcaacg gaaucccaaa agcagcuguu gucuccagag cauuccagcu    60
gcgcuuggau uucgucccu gcucuccugc cu                                  92

<210> SEQ ID NO 223
<211> LENGTH: 84
<212> TYPE: RNA
<213> ORGANISM: Homo sapiens
<220> FEATURE:
<223> OTHER INFORMATION: hsa-mir-196b

<400> SEQUENCE: 223
acuggucggu gauuuaggua guuuccuguu guugggaucc accuuucucu cgacagcacg    60
acacugccuu cauuacuuca guug                                          84

<210> SEQ ID NO 224
<211> LENGTH: 110
<212> TYPE: RNA
<213> ORGANISM: Homo sapiens
<220> FEATURE:
<223> OTHER INFORMATION: hsa-mir-199b

<400> SEQUENCE: 224
ccagaggaca ccuccacucc gucuacccag uguuuagacu aucguucag gacucccaaa    60 uuguacagua gucugcacau ugguuaggcu gggcugggu agacccucgg              110

<210> SEQ ID NO 225
<211> LENGTH: 87
<212> TYPE: RNA
<213> ORGANISM: Homo sapiens
<220> FEATURE:
<223> OTHER INFORMATION: hsa-mir-19b-1

<400> SEQUENCE: 225
cacuguucua ugguuaguuu ugcagguuug cauccagcug ugugauauuc ugcugugcaa    60
auccaugcaa aacugacugu gguagug                                       87

<210> SEQ ID NO 226
<211> LENGTH: 87
<212> TYPE: RNA
<213> ORGANISM: Homo sapiens
<220> FEATURE:
<223> OTHER INFORMATION: hsa-mir-19b-1

<400> SEQUENCE: 226
cacuguucua ugguuaguuu ugcagguuug cauccagcug ugugauauuc ugcugugcaa    60
auccaugcaa aacugacugu gguagug                                       87

<210> SEQ ID NO 227

```
<211> LENGTH: 95
<212> TYPE: RNA
<213> ORGANISM: Homo sapiens
<220> FEATURE:
<223> OTHER INFORMATION: hsa-mir-200b

<400> SEQUENCE: 227
ccagcucggg cagccguggc caucuuacug ggcagcauug gauggaguca ggucucuaau      60
acugccuggu aaugaugacg gcggagcccu gcacg                                95

<210> SEQ ID NO 228
<211> LENGTH: 110
<212> TYPE: RNA
<213> ORGANISM: Homo sapiens
<220> FEATURE:
<223> OTHER INFORMATION: hsa-mir-203a

<400> SEQUENCE: 228
guguugggga cucgcgcgcu gguccagug guucuuaaca guucaacagu ucuguagcgc       60
aauugugaaa uguuuaggac cacuagaccc ggcgggcgcg cgcacagcga                110

<210> SEQ ID NO 229
<211> LENGTH: 71
<212> TYPE: RNA
<213> ORGANISM: Homo sapiens
<220> FEATURE:
<223> OTHER INFORMATION: hsa-mir-20a

<400> SEQUENCE: 229
guagcacuaa agugcuuaua gugcagguag uguuuaguua cuacugcau uaugagcacu       60 uaaaguacug c                                                          71

<210> SEQ ID NO 230
<211> LENGTH: 69
<212> TYPE: RNA
<213> ORGANISM: Homo sapiens
<220> FEATURE:
<223> OTHER INFORMATION: hsa-mir-20b

<400> SEQUENCE: 230
aguaccaaag ugcucauagu gcagguaguu uggcaugac ucuacuguag uaugggcacu       60
uccaguacu                                                             69

<210> SEQ ID NO 231
<211> LENGTH: 110
<212> TYPE: RNA
<213> ORGANISM: Homo sapiens
<220> FEATURE:
<223> OTHER INFORMATION: hsa-mir-210

<400> SEQUENCE: 231
acccggcagu gccuccaggc gcagggcagc ccugcccac cgcacacugc gcugcccag        60 acccacugug cgugugacag cggcugaucu gugccugggc agcgcgaccc                110

<210> SEQ ID NO 232
<211> LENGTH: 72
<212> TYPE: RNA
<213> ORGANISM: Homo sapiens
<220> FEATURE:
<223> OTHER INFORMATION: hsa-mir-21

<400> SEQUENCE: 232
ugucggguag cuuaucagac ugauguugac uguugaaucu cauggcaaca ccagucgaug      60
```

```
ggcugucuga ca                                                           72

<210> SEQ ID NO 233
<211> LENGTH: 84
<212> TYPE: RNA
<213> ORGANISM: Homo sapiens
<220> FEATURE:
<223> OTHER INFORMATION: hsa-mir-25

<400> SEQUENCE: 233
ggccaguguu gagaggcgga gacuugggca auugcuggac gcugcccugg gcauugcacu      60
ugucucgguc ugacagugcc ggcc                                             84

<210> SEQ ID NO 234
<211> LENGTH: 77
<212> TYPE: RNA
<213> ORGANISM: Homo sapiens
<220> FEATURE:
<223> OTHER INFORMATION: hsa-mir-26b

<400> SEQUENCE: 234
ccgggaccca guucaaguaa uucaggauag guugugugcu guccagccug uucuccauua      60
cuuggcucgg ggaccgg                                                     77

<210> SEQ ID NO 235
<211> LENGTH: 86
<212> TYPE: RNA
<213> ORGANISM: Homo sapiens
<220> FEATURE:
<223> OTHER INFORMATION: hsa-mir-301a

<400> SEQUENCE: 235
acugcuaacg aaugcucuga cuuuauugca cuacuguacu uuacagcuag cagugcaaua      60
guauugucaa agcaucugaa agcagg                                           86

<210> SEQ ID NO 236
<211> LENGTH: 78
<212> TYPE: RNA
<213> ORGANISM: Homo sapiens
<220> FEATURE:
<223> OTHER INFORMATION: hsa-mir-301b

<400> SEQUENCE: 236
gccgcaggug cucugacgag guugcacuac ugugcucuga gaagcagugc aaugauauug      60
ucaaagcauc ugggacca                                                    78

<210> SEQ ID NO 237
<211> LENGTH: 86
<212> TYPE: RNA
<213> ORGANISM: Homo sapiens
<220> FEATURE:
<223> OTHER INFORMATION: hsa-mir-323a

<400> SEQUENCE: 237
uugguacuug gagagaggug guccguggcg cguucgcuuu auuuauggcg cacauuacac      60
ggucgaccuc uuugcaguau cuaauc                                           86

<210> SEQ ID NO 238
<211> LENGTH: 83
<212> TYPE: RNA
<213> ORGANISM: Homo sapiens
<220> FEATURE:
```

<223> OTHER INFORMATION: hsa-mir-324

<400> SEQUENCE: 238
cugacuaugc cuccccgcau ccccuagggc auugguguaa agcuggagac ccacugcccc    60
aggugcugcu gggguugua guc                                             83

<210> SEQ ID NO 239
<211> LENGTH: 94
<212> TYPE: RNA
<213> ORGANISM: Homo sapiens
<220> FEATURE:
<223> OTHER INFORMATION: hsa-mir-330

<400> SEQUENCE: 239
cuuuggcgau cacugccucu cugggccugu gucuuaggcu cugcaagauc aaccgagcaa    60
agcacacggc cugcagagag gcagcgcucu gccc                                94

<210> SEQ ID NO 240
<211> LENGTH: 75
<212> TYPE: RNA
<213> ORGANISM: Homo sapiens
<220> FEATURE:
<223> OTHER INFORMATION: hsa-mir-363

<400> SEQUENCE: 240
uguugucggg uggaucacga ugcaauuuug augaguauca uaggagaaaa auugcacggu    60
auccaucugu aaacc                                                     75

<210> SEQ ID NO 241
<211> LENGTH: 70
<212> TYPE: RNA
<213> ORGANISM: Homo sapiens
<220> FEATURE:
<223> OTHER INFORMATION: hsa-mir-369

<400> SEQUENCE: 241
uugaagggag aucgaccgug uuauauucgc uuuauugacu ucgaauaaua cauggugau     60 cuuucucag                                                            70

<210> SEQ ID NO 242
<211> LENGTH: 72
<212> TYPE: RNA
<213> ORGANISM: Homo sapiens
<220> FEATURE:
<223> OTHER INFORMATION: hsa-mir-374a

<400> SEQUENCE: 242
uacaucggcc auuauaauac aaccugauaa guguauagc acuuaucaga uuguauugua    60
auugucugug ua                                                        72

<210> SEQ ID NO 243
<211> LENGTH: 64
<212> TYPE: RNA
<213> ORGANISM: Homo sapiens
<220> FEATURE:
<223> OTHER INFORMATION: hsa-mir-375

<400> SEQUENCE: 243
ccccgcgacg agcccucgc acaaaccgga ccugagcguu uguucguuc ggcucgcgug      60 aggc                                                                 64

-continued

```
<210> SEQ ID NO 244
<211> LENGTH: 66
<212> TYPE: RNA
<213> ORGANISM: Homo sapiens
<220> FEATURE:
<223> OTHER INFORMATION: hsa-mir-376c

<400> SEQUENCE: 244
aaaaggugga uauccuucu auguuuaugu uauuuauggu uaaacauaga ggaaauucca      60
cguuuu                                                                66

<210> SEQ ID NO 245
<211> LENGTH: 66
<212> TYPE: RNA
<213> ORGANISM: Homo sapiens
<220> FEATURE:
<223> OTHER INFORMATION: hsa-mir-378a

<400> SEQUENCE: 245
agggcuccug acuccagguc cuguguguua ccuagaaaua gcacuggacu uggagucaga     60
aggccu                                                               66

<210> SEQ ID NO 246
<211> LENGTH: 72
<212> TYPE: RNA
<213> ORGANISM: Homo sapiens
<220> FEATURE:
<223> OTHER INFORMATION: hsa-mir-451a

<400> SEQUENCE: 246
cuugggaaug gcaaggaaac cguuaccauu acugaguuua guaaggguaa ugguucucuu    60
gcuauaccca ga                                                        72

<210> SEQ ID NO 247
<211> LENGTH: 115
<212> TYPE: RNA
<213> ORGANISM: Homo sapiens
<220> FEATURE:
<223> OTHER INFORMATION: hsa-mir-454

<400> SEQUENCE: 247
ucuguuuauc accagauccu agaaccuau caauauuguc ucugcugugu aaauaguucu     60
gaguagugca auauugcuua uagggguuuug guguuuggaa agaacaaugg gcagg       115

<210> SEQ ID NO 248
<211> LENGTH: 68
<212> TYPE: RNA
<213> ORGANISM: Homo sapiens
<220> FEATURE:
<223> OTHER INFORMATION: hsa-mir-486

<400> SEQUENCE: 248
gcauccugua cugagcugcc ccgaggcccu ucaugcugcc cagcucgggg cagcucagua    60
caggauac                                                             68

<210> SEQ ID NO 249
<211> LENGTH: 68
<212> TYPE: RNA
<213> ORGANISM: Homo sapiens
<220> FEATURE:
<223> OTHER INFORMATION: hsa-mir-486

<400> SEQUENCE: 249
```
gcauccugua cugagcugcc ccgaggcccu ucaugcugcc cagcucgggg cagcucagua       60
caggauac                                                                68

<210> SEQ ID NO 250
<211> LENGTH: 89
<212> TYPE: RNA
<213> ORGANISM: Homo sapiens
<220> FEATURE:
<223> OTHER INFORMATION: hsa-mir-493

<400> SEQUENCE: 250
cuggccucca gggcuuugua caugguaggc uuucauucau ucguuugcac auucggugaa       60
ggucuacugu gugccaggcc cugugccag                                         89

<210> SEQ ID NO 251
<211> LENGTH: 84
<212> TYPE: RNA
<213> ORGANISM: Homo sapiens
<220> FEATURE:
<223> OTHER INFORMATION: hsa-mir-500a

<400> SEQUENCE: 251
gcucccccuc ucuaauccuu gcuaccuggg ugagagugcu gucugaaugc aaugcaccug       60
ggcaaggauu cugagagcga gagc                                              84

<210> SEQ ID NO 252
<211> LENGTH: 91
<212> TYPE: RNA
<213> ORGANISM: Homo sapiens
<220> FEATURE:
<223> OTHER INFORMATION: hsa-mir-532

<400> SEQUENCE: 252
cgacuugcuu ucucuccucc augccuugag uguaggaccg uuggcaucuu aauuacccuc       60
ccacacccaa ggcuugcaaa aaagcgagcc u                                      91

<210> SEQ ID NO 253
<211> LENGTH: 106
<212> TYPE: RNA
<213> ORGANISM: Homo sapiens
<220> FEATURE:
<223> OTHER INFORMATION: hsa-mir-545

<400> SEQUENCE: 253
cccagccugg cacauuagua ggccucagua aauguuuauu agaugaauaa augaaugacu       60
caucagcaaa cauuuauugu gugccugcua aagugagcuc cacagg                      106

<210> SEQ ID NO 254
<211> LENGTH: 97
<212> TYPE: RNA
<213> ORGANISM: Homo sapiens
<220> FEATURE:
<223> OTHER INFORMATION: hsa-mir-550a-1

<400> SEQUENCE: 254
ugaugcuuug cuggcugguc cagugccuga gggaguaaga gcccuguugu uguaagauag       60
ugucuuacuc cccucaggcac aucccaaca agucucu                                97

<210> SEQ ID NO 255
<211> LENGTH: 97
<212> TYPE: RNA
<213> ORGANISM: Homo sapiens

```
<220> FEATURE:
<223> OTHER INFORMATION: hsa-mir-550a-1

<400> SEQUENCE: 255
ugaugcuuug cuggcgguug cagugccuga gggaguaaga gcccuguugu uguaagauag    60
ugucuuacuc ccucaggcac aucuccaaca agucucu                             97

<210> SEQ ID NO 256
<211> LENGTH: 99
<212> TYPE: RNA
<213> ORGANISM: Homo sapiens
<220> FEATURE:
<223> OTHER INFORMATION: hsa-mir-589

<400> SEQUENCE: 256
uccagccugu gcccagcagc cccugagaac cacgucugcu cugagcuggg uacugccugu    60
ucagaacaaa ugccgguucc cagacgcugc cagcuggcc                           99

<210> SEQ ID NO 257
<211> LENGTH: 97
<212> TYPE: RNA
<213> ORGANISM: Homo sapiens
<220> FEATURE:
<223> OTHER INFORMATION: hsa-mir-590

<400> SEQUENCE: 257
uagccaguca gaaaugagcu uauucauaaa agugcaguau ggugaaguca aucuguaauu    60
uuauguauaa gcuagucucu gauugaaaca ugcagca                             97

<210> SEQ ID NO 258
<211> LENGTH: 97
<212> TYPE: RNA
<213> ORGANISM: Homo sapiens
<220> FEATURE:
<223> OTHER INFORMATION: hsa-mir-598

<400> SEQUENCE: 258
gcuugaugau gcugcugaug cuggcgguga ucccgauggu gugagcugga aaugggugc     60 uacgucaucg uugucaucgu caucaucauc auccgag                             97

<210> SEQ ID NO 259
<211> LENGTH: 97
<212> TYPE: RNA
<213> ORGANISM: Homo sapiens
<220> FEATURE:
<223> OTHER INFORMATION: hsa-mir-627

<400> SEQUENCE: 259
uacuuauuac ugguagugag ucucuaagaa aagaggaggu gguuguuuuc cucccucuuuu   60 cuuugagacu cacuaccaau aauaagaaau acuacua                             97

<210> SEQ ID NO 260
<211> LENGTH: 97
<212> TYPE: RNA
<213> ORGANISM: Homo sapiens
<220> FEATURE:
<223> OTHER INFORMATION: hsa-mir-629

<400> SEQUENCE: 260 ucccuuccc aggggagggg cuggguuuac guugggagaa cuuuuacggu gaaccaggag     60
guucucccaa cguaagccca gccccucccc ucugccu                             97
```

```
<210> SEQ ID NO 261
<211> LENGTH: 110
<212> TYPE: RNA
<213> ORGANISM: Homo sapiens
<220> FEATURE:
<223> OTHER INFORMATION: hsa-mir-7-1

<400> SEQUENCE: 261
uuggauguug gccuaguucu guguggaaga cuagugauuu uguuguuuuu agauaacuaa      60
aucgacaaca aaucacaguc ugccauaugg cacaggccau gccucuacag               110

<210> SEQ ID NO 262
<211> LENGTH: 78
<212> TYPE: RNA
<213> ORGANISM: Homo sapiens
<220> FEATURE:
<223> OTHER INFORMATION: hsa-mir-92a-1

<400> SEQUENCE: 262
cuuucuacac agguugggau cgguugcaau gcuguguuuc uguaugguau ugcacuuguc      60
ccggccuguu gaguuugg                                                   78

<210> SEQ ID NO 263
<211> LENGTH: 80
<212> TYPE: RNA
<213> ORGANISM: Homo sapiens
<220> FEATURE:
<223> OTHER INFORMATION: hsa-mir-93

<400> SEQUENCE: 263 cuggggcuc caaagugcug uucgugcagg uagugugauu acccaaccua cugcugagcu       60
agcacuuccc gagccccgg                                                  80

<210> SEQ ID NO 264
<211> LENGTH: 80
<212> TYPE: RNA
<213> ORGANISM: Homo sapiens
<220> FEATURE:
<223> OTHER INFORMATION: hsa-mir-93

<400> SEQUENCE: 264 cuggggcuc caaagugcug uucgugcagg uagugugauu acccaaccua cugcugagcu       60
agcacuuccc gagccccgg                                                  80

<210> SEQ ID NO 265
<211> LENGTH: 72
<212> TYPE: RNA
<213> ORGANISM: Homo sapiens
<220> FEATURE:
<223> OTHER INFORMATION: hsa-mir-941-1

<400> SEQUENCE: 265
uguggacaug ugcccagggc ccgggacagc gccacggaag aggacgcacc cggcugugug      60
cacaugugcc ca                                                         72

<210> SEQ ID NO 266
<211> LENGTH: 86
<212> TYPE: RNA
<213> ORGANISM: Homo sapiens
<220> FEATURE:
<223> OTHER INFORMATION: hsa-mir-942

<400> SEQUENCE: 266
```
auuaggagag uaucuucucu guuuuggcca ugugaguacu cacagcccccu cacacauggc    60 cgaaacagag aaguuacuuu ccuaau    86

<210> SEQ ID NO 267
<211> LENGTH: 78
<212> TYPE: RNA
<213> ORGANISM: Homo sapiens
<220> FEATURE:
<223> OTHER INFORMATION: hsa-mir-96

<400> SEQUENCE: 267
uggccgauuu uggcacuagc acauuuuugc uugugucucu ccgcucugag caaucaugug    60
cagugccaau augggaaa    78

<210> SEQ ID NO 268
<211> LENGTH: 119
<212> TYPE: RNA
<213> ORGANISM: Homo sapiens
<220> FEATURE:
<223> OTHER INFORMATION: hsa-mir-98

<400> SEQUENCE: 268
aggauucugc ucaugccagg gugagguagu aaguuguauu guuguggggu agggauauua    60
ggccccaauu agaagauaac uauacaacuu acuacuuucc cuggugugug gcauauuca    119

<210> SEQ ID NO 269
<211> LENGTH: 21
<212> TYPE: RNA
<213> ORGANISM: Homo sapiens
<220> FEATURE:
<223> OTHER INFORMATION: hsa-miR-382-3p

<400> SEQUENCE: 269
aaucauucac ggacaacacu u    21

<210> SEQ ID NO 270
<211> LENGTH: 76
<212> TYPE: RNA
<213> ORGANISM: Homo sapiens
<220> FEATURE:
<223> OTHER INFORMATION: hsa-mir-382

<400> SEQUENCE: 270
uacuugaaga gaaguuguuc gugguggauu cgcuuuacuu augacgaauc auucacggac    60
aacacuuuuu ucagua    76

<210> SEQ ID NO 271
<211> LENGTH: 23
<212> TYPE: RNA
<213> ORGANISM: Homo sapiens
<220> FEATURE:
<223> OTHER INFORMATION: hsa-miR-181a-5p

<400> SEQUENCE: 271
aacauucaac gcugucggug agu    23

<210> SEQ ID NO 272
<211> LENGTH: 110
<212> TYPE: RNA
<213> ORGANISM: Homo sapiens
<220> FEATURE:
<223> OTHER INFORMATION: hsa-mir-181a-2

```
<400> SEQUENCE: 272
agaagggcua ucaggccagc cuucagagga cuccaaggaa cauucaacgc ugucggugag      60
uuugggauuu gaaaaaacca cugaccguug acuguaccuu gggguccuua                110

<210> SEQ ID NO 273
<211> LENGTH: 22
<212> TYPE: RNA
<213> ORGANISM: Homo sapiens
<220> FEATURE:
<223> OTHER INFORMATION: hsa-miR-32-3p

<400> SEQUENCE: 273
caauuuagug ugugugauau uu                                               22

<210> SEQ ID NO 274
<211> LENGTH: 70
<212> TYPE: RNA
<213> ORGANISM: Homo sapiens
<220> FEATURE:
<223> OTHER INFORMATION: hsa-mir-32

<400> SEQUENCE: 274
ggagauauug cacauuacua aguugcaugu ugucacggcc ucaaugcaau uuagugugug      60
ugauauuuuc                                                             70
```

COMPOSITIONS AND METHODS FOR THE DIAGNOSIS AND TREATMENT OF BONE FRACTURES AND DISORDERS

CROSS-REFERENCE TO RELATED APPLICATIONS

This application is the U.S. national stage of International Patent Application No. PCT/EP2015/063091, filed on Jun. 11, 2015 and entitled COMPOSITIONS AND METHODS FOR THE DIAGNOSIS AND TREATMENT OF BONE FRACTURES AND DISORDERS, which claims the benefit of priority under 35 U.S.C. § 119 from European Patent Application No. 14198560.6, filed on Dec. 17, 2014, and from European Patent Application No. 14172354.4, filed Jun. 13, 2014. The disclosures of the foregoing applications are incorporated herein by reference in their entirety.

FIELD OF THE INVENTION

The present invention relates to the therapy, prophylaxis and diagnosis of disorders that are associated with aberrant bone mineral density, in particular osteoporosis.

BACKGROUND OF THE INVENTION

Osteoporosis is characterized by a systemic reduction in bone mass leading to increased bone fragility and an increased risk of bone fracture.

Current methods for the early assessment of fracture risk as well as treatment response include non-invasive imaging techniques as well as the analysis of clinical parameters and biochemical markers of bone turnover. Recently, microRNAs have been identified to be secreted into the bloodstream from cells of various tissues, possibly indicating pathological processes in different parts of the body. There is evidence that microRNAs play an important role in the development and function of bone forming and bone resorbing cells, specifically osteoblasts and osteoclasts. Both cell types control the homeostasis between bone anabolism and catabolism, and therefore microRNAs play a pivotal physiological role in bone metabolism. To this day, however, little is known whether an imbalance in bone metabolism, which causes bone diseases, may be reflected in the levels of circulating microRNAs.

Osteoporotic fractures are caused by an increase in bone fragility, which can occur due to low bone mass and micro-architectural changes in bone tissue. Such fractures are the critical hard outcome of osteoporosis, which affects more than 75 million people in the United States, Europe and Japan (Kanis et al., 2013). With a lifetime risk of 30%-40% to be affected by vertebral or non-vertebral fractures in developed countries, osteoporosis has an incidence rate similar to that of coronary heart disease. Furthermore, with the exception of forearm fractures, osteoporotic fractures are associated with increased mortality. Most fractures cause acute pain and lead to patient hospitalization, immobilization and often slow recovery.

In addition, osteoporotic symptoms are frequently observed in patients with type 2 diabetes, who overall suffer from an elevated risk of fragility fractures. Diabetes mellitus refers to a group of metabolic diseases in which a subject has high blood sugar. Type 2 diabetes results from insulin resistance, a condition in which cells fail to use insulin properly, sometimes also with an absolute insulin deficiency. This form was previously referred to as non insulin-dependent diabetes mellitus (NIDDM) or "adult-onset diabetes".

In the prophylaxis, diagnosis and management of osteoporosis, the assessment of fracture risk and monitoring of treatment response are two of the most important aspects. Therefore, analysis of bone mass by measuring bone mineral density (BMD) is currently the only clinical parameter of the skeleton that is routinely analyzed in clinical practice and part of the WHO FRAX questionnaire (Kanis et al., 2013). However, due to the lacking correlation with bone strength and bone metabolism (Cefalu, 2004), age- and site-dependent differences in bone density, the assessment of the T-Score (i.e. a comparison of a patient's BMD to that of a healthy thirty-year-old) in combination with other established clinical scores of fracture risk (Rubin et al., 2013) often does not improve the prediction of fracture risk. Particularly in case of patients suffering from type-2 diabetes there is no evidence for correlation between BMD and fracture risk, which demonstrates the need for alternative markers of fracture risk.

In order to estimate the rate of bone formation, bone resorption and therapeutic treatment response, few biochemical bone turnover markers (BTM) have been identified (Vasikaran et al., 2011), such as serum procollagen type I N propeptide (s-PINP), serum C-terminal telopeptide of type I collagen (s-CTX). While the correlation of these markers with bone metabolism has been established, their specificity and sensitivity for fracture risk prediction needs to be further validated. Therefore, only few countries have recommended to incorporate these biochemical markers into clinical practice (Vasikaran et al., 2011).

Other potential markers of bone metabolism may be derived from the signaling pathways that are known to play a major role in bone formation and resorption, such as WNT, BMP-2 or RANKL. For example, proteins derived from Dickkopf-1 (DKK-1) or Sclerostin (SOST) genes can act as binding partners of WNT and WNT-receptors, thereby regulating its activity and subsequently bone formation (Canalis, 2013). However, the pre-analytical stability of these proteins in serum/plasma in response to diet, exercise and circadian rhythm is questionable, and so is the general significance for bone metabolism due to the fact that these proteins are produced in other tissues as well and might be regulated in response to other diseases. Especially in respect to certain types of cancer, WNT-signalling has been shown to drive the progression of disease (Anastas & Moon, 2013).

Recently, increased attention has been attributed to the importance of microRNAs (miRNAs), small non-coding RNAs that regulate gene expression (Bartel, 2009), in the control of bone metabolism (Dong, Yang, Guo, & Kang, 2012; Zhao et al., 2013). Several miRNAs have been shown to silence osteogenic inhibitors during stem cell differentiation into osteocytes (Trompeter et al., 2013), to regulate BMP2-mediated osteoblast proliferation and differentiation (Li et al., 2008), or to orchestrate the activity of WNT-signalling (Kapinas, Kessler, & Delany, 2009). Therefore, the potential of miRNAs as therapeutic agents for accelerating bone regeneration and/or as diagnostic tools for evaluating bone metabolism and fracture risk has recently been acknowledged (van Wijnen et al., 2013). The impressive stability of miRNA in serum and plasma even after being subjected to harsh conditions, the limited number of miRNAs (<500 found secreted in plasma/serum), their simple chemical composition, the lack of posttranscriptional modification and the availability of advanced and well established, highly sensitive screening techniques define miRNAs as excellent candidates for biomarkers. In fact, blood-circulating miRNAs have already been analyzed in the context of disease (Keller et al., 2011), especially cancer and cardiovascular disease, or non-pathological processes such as ageing (Weiner et al., 2013). A combination of miRNAs that can control the onset and progression of osteoporosis or can serve as surrogate markers for this pathological process, is a specific osteoporosis signature whose use would represent a non-invasive approach to predict the fracture risk as well as targets for therapeutic control of the progression of osteoporosis.

WO2013155085 suggests a diagnostic method for low bone mineral density that detects hsa-miR-133a in monocytes.

Recently, five freely circulating miRNAs and bone tissue miRNAs have been identified and implicated with osteoporotic fractures (Seeliger et al., 2014).

WO2007023306 describes the use of miRNA-223 for diagnosis of a bone disease.

Wang Y. et al., 2012, PlosOne, 7,4, e34641 report miR-133a as potential biomarker associated with postmenopausal osteoporosis.

WO2011144761 describes miR-31 for use in the treatment of bone disorders.

SUMMARY OF THE INVENTION

It is the objective of the present invention, to broaden both the scope, specificity and validity in diagnosing osteoporosis or osteopenia and predicting fractures, and to provide novel agents for the therapy of osteoporosis by stabilizing bone homeostasis and accelerating fracture healing.

The problem is solved by the present invention.

The inventors have detected specific miRNAs that are up- or down-regulated in blood samples derived from patients with recent as well as non-recent osteoporotic fractures.

The present invention specifically provides a selected set of miRNAs that are specifically up- or down-regulated and are thus useful as valuable biomarkers and represent a diagnostic signature applicable both over a broad range of bone disease stages and age groups.

According to the invention there is provided an in vitro method of diagnosing osteoporosis, determining the risk of osteoporotic fractures or monitoring of treatment success in a subject, comprising the steps of:

a) providing a blood or serum sample from said subject;
b) measuring the level of two or more miRNAs selected from any of 1. group II miRNAs consisting of hsa-miR-188-3p, hsa-miR-382-3p, hsa-let-7i-3p, hsa-miR-1227-3p, hsa-miR-127-3p, hsa-miR-133b, hsa-miR-135a-5p, hsa-miR-136-3p, hsa-miR-143-3p, hsa-miR-155-5p, hsa-miR-181a-3p, hsa-miR-1908, hsa-miR-190a, hsa-miR-192-5p, hsa-miR-193b-3p, hsa-miR-196b-5p, hsa-miR-199b-5p, hsa-miR-200b-3p, hsa-miR-203a, hsa-miR-205-5p, hsa-miR-20b-5p, hsa-miR-214-3p, hsa-miR-215, hsa-miR-223-5p, hsa-miR-27a-3p, hsa-miR-30e-3p, hsa-miR-323a-3p, hsa-miR-330-3p, hsa-miR-342-5p, hsa-miR-369-3p, hsa-miR-376c-3p, hsa-miR-377-3p, hsa-miR-378a-5p, hsa-miR-410, hsa-miR-454-3p, hsa-miR-487b, hsa-miR-495-3p, hsa-miR-500a-5p, hsa-miR-502-5p, hsa-miR-542-5p, hsa-miR-548a-3p, hsa-miR-550a-5p, hsa-miR-576-3p, hsa-miR-582-3p, hsa-miR-624-5p, hsa-miR-642a-5p, hsa-miR-941, and hsa-miR-942 or isoforms or variants thereof, and/or 2. group III miRNAs consisting of hsa-miR-181a-5p, hsa-miR-32-3p, hsa-let-7b-5p, hsa-let-7g-5p, hsa-let-7i-5p, hsa-miR-106a-5p, hsa-miR-106b-5p, hsa-miR-127-3p, hsa-miR-132-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-16-2-3p, hsa-miR-16-5p, hsa-miR-17-5p, hsa-miR-181b-5p, hsa-miR-181c-3p, hsa-miR-181c-5p, hsa-miR-185-5p, hsa-miR-18a-3p, hsa-miR-18a-5p, hsa-miR-18b-5p, hsa-miR-1908, hsa-miR-191-5p, hsa-miR-196b-5p, hsa-miR-199b-5p, hsa-miR-19b-1-5p, hsa-miR-19b-3p, hsa-miR-200b-3p, hsa-miR-203a, hsa-miR-20a-5p, hsa-miR-20b-5p, hsa-miR-210, hsa-miR-21-3p, hsa-miR-25-3p, hsa-miR-26b-5p, hsa-miR-301a-3p, hsa-miR-301b, hsa-miR-323a-3p, hsa-miR-324-5p, hsa-miR-330-3p, hsa-miR-363-3p, hsa-miR-369-3p, hsa-miR-374a-5p, hsa-miR-375, hsa-miR-376c-3p, hsa-miR-378a-5p, hsa-miR-451a, hsa-miR-454-3p, hsa-miR-486-3p, hsa-miR-486-5p, hsa-miR-493-5p, hsa-miR-500a-5p, hsa-miR-532-3p, hsa-miR-545-3p, hsa-miR-550a-3p, hsa-miR-550a-5p, hsa-miR-589-5p, hsa-miR-590-3p, hsa-miR-598, hsa-miR-627, hsa-miR-629-5p, hsa-miR-7-5p, hsa-miR-92a-3p, hsa-miR-93-3p, hsa-miR-93-5p, hsa-miR-941, hsa-miR-942, hsa-miR-96-5p, and hsa-miR-98-5p or isoforms or variants thereof, and/or 3. group I miRNAs consisting of hsa-miR-10a-5p, hsa-miR-10b-5p, hsa-miR-125b-5p, hsa-miR-127-3p, hsa-miR-133a, hsa-miR-133b, hsa-miR-143-3p, hsa-miR-18a-3p, hsa-miR-194-5p, hsa-miR-30a-5p, hsa-miR-328-3p, hsa-miR-376a-3p, hsa-miR-409-3p, hsa-miR-574-3p, or isoforms or variants thereof in said serum or blood sample and c) comparing the level of said miRNAs with the level of the corresponding miRNA in a reference blood or serum sample from a healthy individual, wherein a difference by more than 1.5 fold in said level when compared to the reference sample is indicative of osteoporosis or the risk of fractures, specifically of osteoporotic fractures.

In an alternative embodiment of the invention, the level of said miRNAs can be compared with the average level of corresponding miRNAs in healthy subjects, specifically in a pool of samples derived from healthy subjects, wherein a difference by more than one standard deviations, specifically by about 1.5, 1.6, 1.7, 1.8, 1.9, specifically about 2 standard deviations or more is indicative of osteoporosis with increased risk of future fractures, specifically of osteoporotic fractures.

According to a further embodiment, a difference by more than 2.5 standard deviations, specifically about 3, specifically about 3.5, specifically more than 3.5 standard deviations is indicative of osteoporosis with high risk of future fractures, specifically of osteoporotic fractures.

Thus it is within the embodiment of the invention to use either a single reference sample from a healthy subject or a pool of samples derived from healthy subjects for comparison with the respective sample from a subject to be diagnosed. Said pool can consist of 2, 3, 4, 5, 6, 7, or more samples, specifically up to 10, 100 or more than 100 blood samples from different individuals.

In a specific embodiment of the invention, an in vitro method of diagnosing osteoporosis or predicting the risk of fractures in selected subjects or subject populations is provided, comprising the steps of:

a. providing a blood sample from a subject which is not suffering from or not having a predisposition to develop diabetes mellitus, specifically diabetes mellitus type II, b. measuring the level of two or more miRNAs selected from any of group I miRNAs and/or group II miRNAs as specifically listed above and optionally, in addition c. one or more further miRNAs that are differentially regulated in osteoporotic individuals as compared to healthy individuals, and/or that are involved in osteogenic differentiation and/or in osteoclastogenic activation; and d. comparing the level of said miRNAs, or isoforms and variants thereof with the average level in a cohort of healthy individuals, wherein a difference by more than one standard deviations, specifically about 1.5, specifically about 2 standard deviations compared to the reference is indicative of osteoporosis with increased risk of future osteoporotic fractures, while a difference by more than 2.5 standard deviations, specifically about 3, specifically about 3.5, more specifically more than 3.5 standard deviations is indicative of osteoporosis with high risk of future fractures.

In a further specific embodiment of the invention, an in vitro method of diagnosing osteoporosis or predicting the risk of fractures in selected subject populations is provided, comprising the steps of:

a) providing a blood sample from a subject which is diagnosed of suffering from or has a predisposition to develop diabetes mellitus, specifically diabetes mellitus type II, b) measuring the level of two or more miRNAs selected from group III miRNAs as specifically listed above and optionally, in addition c) one or more further miRNAs that are differentially regulated in osteoporotic individuals as compared to healthy individuals, and/or that are involved in osteogenic differentiation and/or in osteoclastogenic activation; and d) comparing the level of said miRNAs, or isoforms and variants thereof with the average level in a cohort or pool of healthy individuals, wherein a difference by more than one standard deviations, specifically about 1.5, specifically about 2 standard deviations compared to the reference is indicative of osteoporosis with increased risk of future osteoporotic fractures, while a difference by more than 2.5 standard deviations, specifically about 3, specifically about 3.5, more specifically more than 3.5 standard deviations is indicative of osteoporosis with high risk of future fractures.

In a further embodiment of the invention, the level of two or more human miRNAs from group I miRNAs are measured according to the method of the invention. Specifically, the level of 3, 4, 5, 6, 7, 8, 9, 10, 11, 12, 13 or 14 miRNAs of group I are determined and compared with the level of a standard reference sample which may be a single sample or a pool of samples from healthy donors.

In a further embodiment of the invention, the level of said two or more human miRNAs from group II miRNAs are measured according to the method of the invention. Specifically, the level of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47 or 48 miRNAs of group II are determined and compared with the level of a standard reference sample which may be a single sample or a pool of samples from healthy donors.

In a further embodiment of the invention, the level of said two or more human miRNAs from group III miRNAs are measured according to the method of the invention. Specifically, the level of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73 or 74 miRNAs of group III are determined and compared with the level of a standard reference sample which may be a single sample or a pool of samples from healthy donors.

Also any combinations of measurements of the miRNA levels of said group I, group II, and group III miRNAs as listed above are of course incorporated in the scope of the present invention.

According to a further embodiment of the invention, the level of at least 3, preferably at least 4, at least 5, at least 6, at least 7, . . . up to 136 miRNAs of any of groups I, II or III is measured.

According to a specific embodiment of the invention, the level of all miRNAs of any of group I and/or group II and/or group III miRNAs is measured.

According to a specific aspect, a method is provided, wherein the level of hsa-miR-127-3p, hsa-miR-133b and hsa-miR-143-3p, is measured.

A further specific aspect is to provide the inventive method, wherein the level of hsa-miR-106a-5p, hsa-miR-127-3p, hsa-miR-133b, hsa-miR-143-3p, hsa-miR-18a-3p, hsa-miR-196b-5p, hsa-miR-199b-5p, hsa-miR-200b-3p, hsa-miR-203a, hsa-miR-20b-5p, hsa-miR-323a-3p, hsa-miR-330-3p, hsa-miR-369-3p, hsa-miR-376c-3p, hsa-miR-378a-5p, hsa-miR-454-3p, hsa-miR-500a-5p, hsa-miR-550a-5p, hsa-miR-941, and hsa-miR-942 is measured.

According to a further aspect of the inventive method, the levels of at least two of hsa-miR-188-3p, hsa-miR-382-3p, hsa-miR-942 and hsa-miR-155-5p are measured specifically for diagnosis of osteoporosis or determining the risk of fractures in individuals, specifically post-menopausal women that have no signs of diabetes mellitus type 2 disease. Optionally, said at least two miRNAs as listed above can be measured in combination with at least one of hsa-miR-136-3p, hsa-miR-181a-3p, hsa-miR-378a-5p, hsa-miR-502-5p, hsa-miR-550a-5p, hsa-miR-576-3p and hsa-miR-582-3p.

In yet a further aspect of the present invention, the levels of at least two of miR-550a-5p, miR-32-3p, miR-96-5p and miR-486-3p are measured specifically for diagnosis of osteoporosis or determining the risk of fractures in individuals, specifically post-menopausal women that suffer from diabetes mellitus disease. Optionally, said at least two miRNAs as listed above can be measured in combination with at least one of hsa-let-7g-5p, hsa-miR-141-3p, hsa-miR-143-5p, hsa-miR-16-2-3p, hsa-miR-181a-5p, hsa-miR-181c-3p, hsa-miR-203a, hsa-miR-323a-3p, hsa-miR-500a-5p, hsa-miR-532-39, hsa-miR-7-5p, hsa-miR-92a-3p.

In a further aspect, one or more further miRNAs are detected by the method of the invention, wherein said miRNAs are i) differentially regulated in osteoporotic individuals as compared to healthy individuals and are ii) involved in osteogenic differentiation and/or in osteoclastogenic activation.

In yet a further embodiment, additional miRNAs are detected, which are selected from group IV miRNAs, consisting of hsa-miR-100, hsa-miR-124a, hsa-miR-148a, hsa-miR-23a, hsa-miR-24, hsa-miR-31, hsa-miR-22-3p and hsa-miR-93.

In a further embodiment of the invention further miRNAs are measured in the inventive method which are selected from group V miRNAs, consisting of hsa-miR-140-5p, hsa-miR-146a-5p, hsa-miR-155-5p, hsa-miR-199a-5p, hsa-miR-20a, hsa-miR-200a, hsa-miR-217, hsa-miR-218, hsa-miR-26a, hsa-miR-27b, hsa-miR-2861, hsa-miR-29a-3p, hsa-miR-29b-3p, hsa-miR-29c-3p, hsa-miR-204-5p, hsa-miR-335-5p, hsa-miR-34c, hsa-miR-370-3p, hsa-miR-3960, hsa-miR-503-5p, or isoforms and variants thereof.

According to an alternative embodiment of the invention, a method is provided to determine whether a subject has osteoporosis or is at risk of developing osteoporosis comprising the steps of:

a) providing a blood or serum sample from said subject;

b) measuring the level of two or more miRNAs selected from any of group II, III or I miRNAs, or any of the other above listed miRNAs or isoforms or variants thereof in said serum or blood sample and c) comparing the level of said miRNAs with the level of the corresponding miRNA in a reference blood or serum sample from a healthy individual, d) treating osteoporosis in the subject showing a difference of more than 1.5 fold in said level of miRNAs when compared to the reference sample.

In a further embodiment, the subjects are osteopenia patients suffering from or being at risk of developing bone fractures, or patients being at risk of or suffering from type 2 diabetes mellitus, wherein said subjects receive treatment if the level of two or more of the respective miRNAs as listed above show a enhancement or reduction of more than 1.5 fold when compared to the reference sample.

The present invention thus also provides a method for monitoring a subject and/or for the prognosis of bone fraction, specifically of osteoporotic bone fraction.

The inventive method can be used as standard testing for any subjects where a risk for fractures shall be determined, specifically said subjects are osteoporosis patients suffering from or being at risk of developing bone fractures, or patients being at risk of or suffering from diabetes mellitus, specifically from type 2 diabetes mellitus.

According to a specific embodiment of the invention, the difference in miRNA levels is determined by quantitative or digital PCR, DNA/RNA sequencing, microarray, Luminex™ luminescence based nucleic acid assays, or other hybridization-based techniques.

The present invention also provides a composition for use in treating or preventing osteoporosis or fractures consisting of the a) replacement of endogenous microRNAs using at least one, specifically at least two isolated, synthetic human miRNAs including isoforms from miRNA groups I, II or III and/or b) inhibition and/or degradation of at least two of miR-NAs of groups I, II or III by administration of synthetic antagonists/inhibitor molecules which
  i. bind, cleave and therefore decrease the level of said miRNAs; and/or
  ii. bind and sequester the target miRNA, therefore down-regulating expression of the sequences coding for said miRNAs.

Specifically ribozymes may be used therfore.

Specifically, said composition can be used in the preparation of a medicament.

According to a further embodiment of the invention, a method for treating or preventing osteoporosis or fractures in a subject, comprising administering an effective amount of a) at least two isolated human miRNAs from miRNA groups I, II or III and/or b) an antagonist/inhibitor of at least two of miRNAs of groups I, II or III that
  i) decreases the level of said miRNAs; and/or
  ii) inhibits or down-regulates expression of the sequences coding for said miRNAs.

FIGURES

FIG. 1: Multivariate classification models. a) Receiver operating characteristic (ROC) curves for classification of post-menopausal women with non-recent fractures (Fx) from control patients (Co), based on combinations of 1-4 miRNAs: hsa-miR-188-3p, hsa-miR-382-3, hsa-miR-942, and hsa-miR-155-5p. b) Boxplots representing normalized Cp-values of the miRNAs from a) in serum samples of post-menopausal women with and without non-recent osteoporotic fractures. c) ROC curves for classification of type-2 diabetic women suffering from non-recent osteoporotic fractures (DMFx) from diabetic control patients without fractures (DM), based on combinations of 1-4 miRNAs: miR-550a-5p, miR-32-3p, miR-96-5p, miR-486-3p. d) Boxplots representing normalized Cp-values of the miRNAs in c) in serum samples of DMFx vs DM samples.

Figure 2:
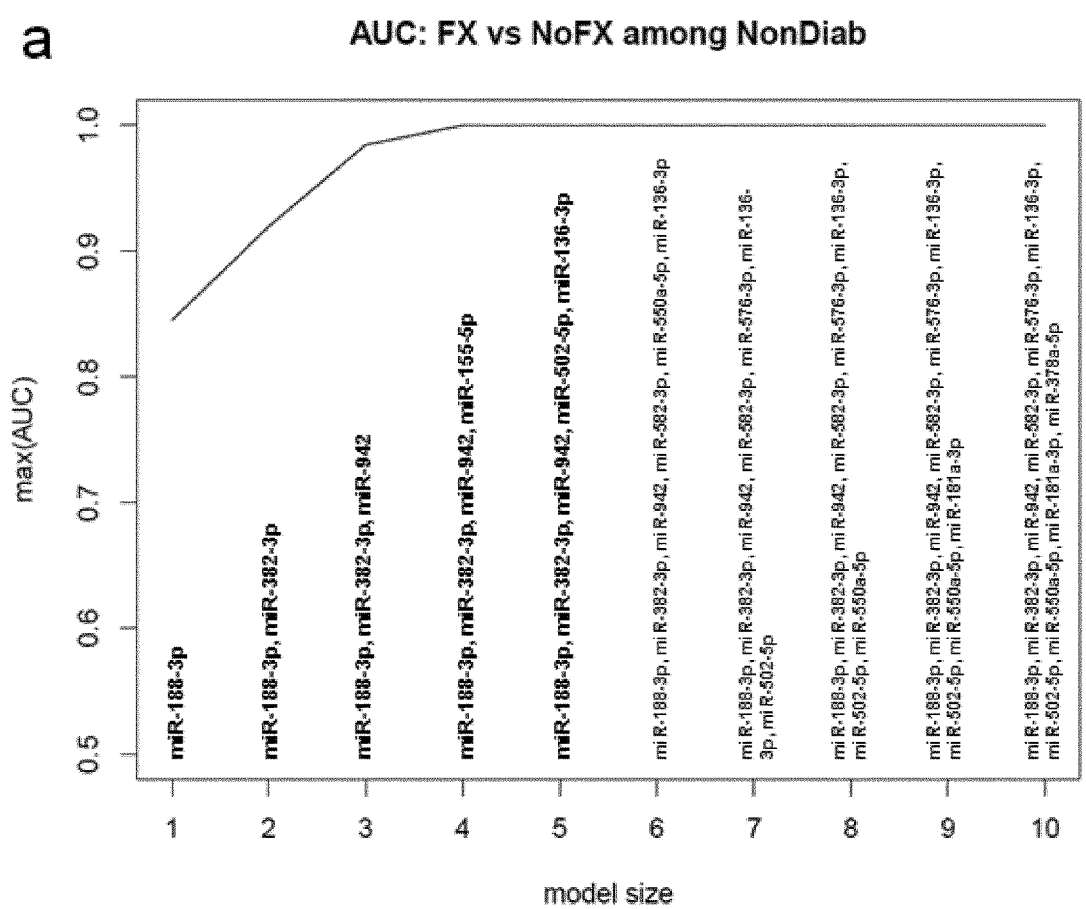
Figure 2:
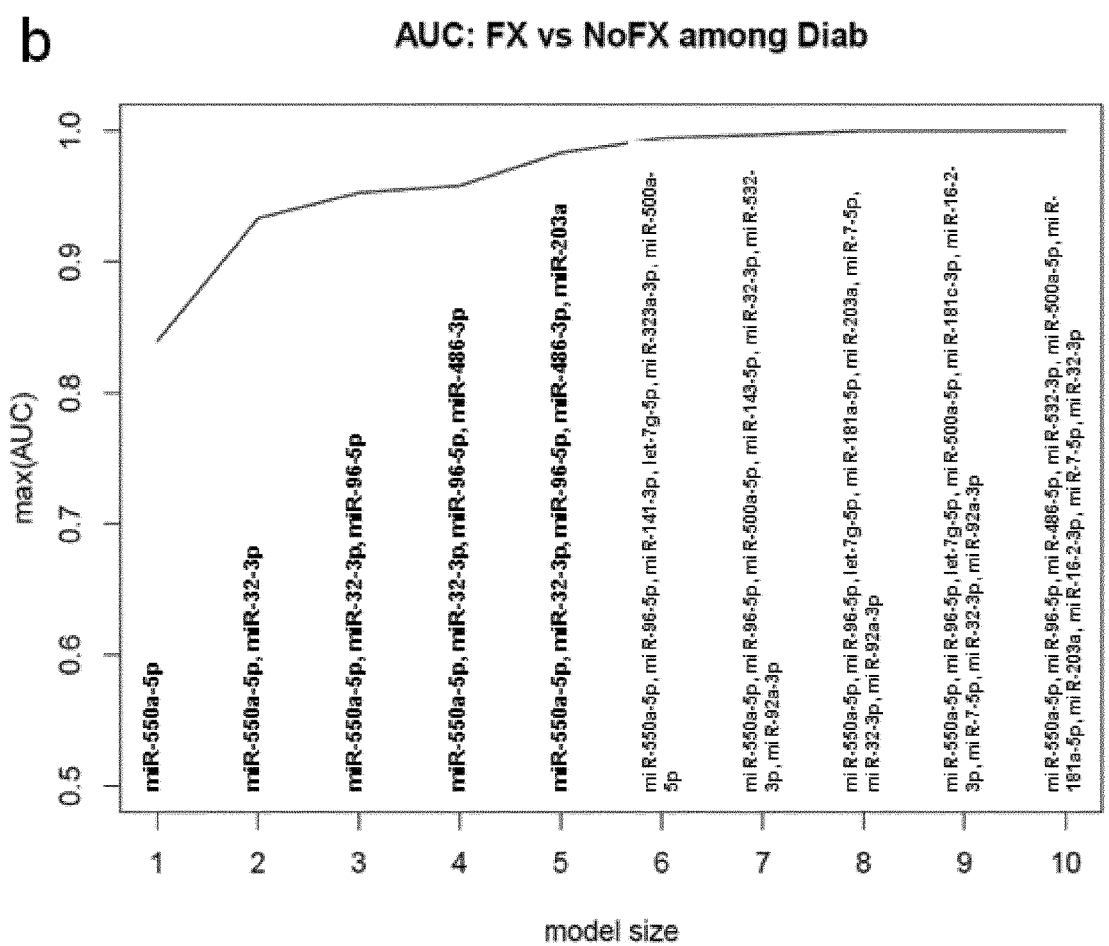

FIG. 2: Multivariate classification models: Expansion or replacement of 4-parameter models by additional miRNA improves classification performance. a) Osteoporosis in post-menopausal women without type-2 diabetes: the effect of combining the analysis of hsa-miR-188-3p with up to 9 miRNAs on the classification of female fracture patients is shown as AUC values derived from ROC-analysis. b) Osteoporosis in patients with type-2 diabetes: the effect of combining the analysis of miR-550a-5p with up to 9 microRNAs on the classification of female fracture patients with type-2 diabetes is shown as AUC values from ROC-analysis. AUC=1.0 presents a perfect classification.

DETAILED DESCRIPTION OF THE INVENTION

Osteogenic differentiation is defined as the process during which a mesenchymal stem cell or adipose tissue derived stem cell becomes activated to proliferate and differentiate into an osteoblast. This process is characterized by secretion of alkaline phosphatase (ALP), changes in gene expression such as Osteocalcin, RUNX2, ALP, and elevated calcium incorporation.

Osteoclastogenic formation is defined as the process during which monocytes (i.e. macrophages) are activated by RANKL and M-CSF to form osteoclasts, which are characterized by release of $H^+$, specific proteases and other enzymes such as tartreate resistant acidic phosphatase (TRAP), Cathepsin K, which assist in bone resorption.

As used herein, the term "blood sample" refers to serum, plasma, whole blood and its components, blood derived products or preparations. Plasma and serum are very useful as shown in the examples.

As used herein, the term "subject" or "individual" or "patient" shall refer to a warm-blooded mammalian, particularly a human being.

The term "patient" includes human and other mammalian subjects that receive either prophylactic or therapeutic treatment or are diagnosed of a specific disease, like but not limited to osteoporosis or diabetes mellitus.

The term "treatment" is thus meant to include both prophylactic and therapeutic treatment.

As used therein, the term "cohort of individuals" or "pool of individuals" shall refer to a group of healthy individuals and may specifically refer to the samples received from said individuals. The number of individuals of a cohort can vary, i.e. it may comprise 2, 3, 4, 5, 6, 7 or more individuals, however it also may be a larger group of subjects, like for example but not limited to 10, 50, 100 or more individuals. According to the embodiment of the invention the cohort may also comprise large cohorts of 500 or more individuals.

According to the invention, the term "about" encompasses the explicitly recited values as well as small deviations therefrom. Accordingly, a deviation from a recited value for 10%, preferably 5%, preferably 1% is encompassed by the term "about". According to the invention, subjects with primary osteoporosis (post-menopausal) with mean ages of about 60 years were assessed, which stands in contrast to bone loss and fracture risk due to senile osteoporosis, which affects subjects of about 70 years or older.

The term "treatment success" as used herein is defined as maintaining the bone density or delaying the process of osteoporosis and decreasing the risk of breaking a bone (osteoporotic fracture) as a result of osteoporosis. Hence, a marker that predicts treatment success should be preferentially related to the clinical outcome for a patient, i.e. the reduction in fracture risk. Moderate treatment success reduces fracture risk by about 25% up to about 50%. High treatment success results in a risk reduction by more than 50%.

The present invention provides selected miRNAs for use in a method for diagnosing osteoporosis, determining the risk of developing osteoporotic lesions or fractures or monitoring the treatment in subjects undergoing therapy, specifically osteoporosis or diabetes treatment.

Said miRNAs are hsa-miR-382-3p, hsa-miR-181a-5p, hsa-miR-32-3p hsa-let-7b-5p, hsa-let-7g-5p, hsa-let-7i-3p, hsa-let-7i-5p, hsa-miR-106a-5p, hsa-miR-106b-5p, hsa-miR-10a-5p, hsa-miR-10b-5p, hsa-miR-1227-3p, hsa-miR-125b-5p, hsa-miR-127-3p, hsa-miR-132-3p, hsa-miR-133a, hsa-miR-133b, hsa-miR-135a-5p, hsa-miR-136-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-155-5p, hsa-miR-16-2-3p, hsa-miR-16-5p, hsa-miR-17-5p, hsa-miR-181a-3p, hsa-miR-181b-5p, hsa-miR-181c-3p, hsa-miR-181c-5p, hsa-miR-185-5p, hsa-miR-188-3p, hsa-miR-18a-3p, hsa-miR-18a-5p, hsa-miR-18b-5p, hsa-miR-1908, hsa-miR-190a, hsa-miR-191-5p, hsa-miR-192-5p, hsa-miR-193b-3p, hsa-miR-194-5p, hsa-miR-196b-5p, hsa-miR-199b-5p, hsa-miR-19b-1-5p, hsa-miR-19b-3p, hsa-miR-200b-3p, hsa-miR-203a, hsa-miR-205-5p, hsa-miR-20a-5p, hsa-miR-20b-5p, hsa-miR-210, hsa-miR-21-3p, hsa-miR-214-3p, hsa-miR-215, hsa-miR-223-5p, hsa-miR-25-3p, hsa-miR-26b-5p, hsa-miR-27a-3p, hsa-miR-301a-3p, hsa-miR-301b, hsa-miR-30a-5p, hsa-miR-30e-3p, hsa-miR-323a-3p, hsa-miR-324-5p, hsa-miR-328-3p, hsa-miR-330-3p, hsa-miR-342-5p, hsa-miR-363-3p, hsa-miR-369-3p, hsa-miR-374a-5p, hsa-miR-375, hsa-miR-376a-3p, hsa-miR-376c-3p, hsa-miR-377-3p, hsa-miR-378a-5p, hsa-miR-409-3p, hsa-miR-410, hsa-miR-451a, hsa-miR-454-3p, hsa-miR-486-3p, hsa-miR-486-5p, hsa-miR-487b, hsa-miR-493-5p, hsa-miR-495-3p, hsa-miR-500a-5p, hsa-miR-502-5p, hsa-miR-532-3p, hsa-miR-542-5p, hsa-miR-545-3p, hsa-miR-548a-3p, hsa-miR-550a-3p, hsa-miR-550a-5p, hsa-miR-574-3p, hsa-miR-576-3p, hsa-miR-582-3p, hsa-miR-589-5p, hsa-miR-590-3p, hsa-miR-598, hsa-miR-624-5p, hsa-miR-627, hsa-miR-629-5p, hsa-miR-642a-5p, hsa-miR-7-5p, hsa-miR-92a-3p, hsa-miR-93-3p, hsa-miR-93-5p, hsa-miR-941, hsa-miR-942, hsa-miR-96-5p and hsa-miR-98-5p- or isoforms or variants thereof.

The detection of an increase or decrease of the level of two or more of said miRNAs compared to the level in healthy subjects can be used for predicting a risk of osteoporosis or fractures in a subject.

Specifically, measuring an increase of the level of group I miRNAs, specifically of two or more of said miRNAs, consisting of hsa-miR-10a-5p, hsa-miR-10b-5p, hsa-miR-125b-5p, hsa-miR-127-3p, hsa-miR-133a, hsa-miR-133b, hsa-miR-143-3p, hsa-miR-18a-3p, hsa-miR-194-5p, hsa-miR-30a-5p, hsa-miR-328-3p, hsa-miR-376a-3p, hsa-miR-409-3p, hsa-miR-574-3p, or isoforms or variants thereof can be a specific indicative for osteoporosis or risk for developing osteoporosis. Said increase or decrease of miRNAs is specifically based on data derived from blood or serum levels in subjects who were suffering from recent fractures.

Specifically, measuring an increase of the level of group II miRNAs, specifically of two or more of said miRNAs, consisting of hsa-miR-382-3p, hsa-let-7i-3p, hsa-miR-1227-3p, hsa-miR-127-3p, hsa-miR-133b, hsa-miR-135a-5p, hsa-miR-136-3p, hsa-miR-143-3p, hsa-miR-155-5p, hsa-miR-181a-3p, hsa-miR-188-3p, hsa-miR-1908, hsa-miR-190a, hsa-miR-192-5p, hsa-miR-193b-3p, hsa-miR-196b-5p, hsa-miR-199b-5p, hsa-miR-200b-3p, hsa-miR-203a, hsa-miR-205-5p, hsa-miR-20b-5p, hsa-miR-214-3p, hsa-miR-215, hsa-miR-223-5p, hsa-miR-27a-3p, hsa-miR-30e-3p, hsa-miR-323a-3p, hsa-miR-330-3p, hsa-miR-342-5p, hsa-miR-369-3p, hsa-miR-376c-3p, hsa-miR-377-3p, hsa-miR-378a-5p, hsa-miR-410, hsa-miR-454-3p, hsa-miR-487b, hsa-miR-495-3p, hsa-miR-500a-5p, hsa-miR-502-5p, hsa-miR-542-5p, hsa-miR-548a-3p, hsa-miR-550a-5p, hsa-miR-576-3p, hsa-miR-582-3p, hsa-miR-624-5p, hsa-miR-642a-5p, hsa-miR-941, hsa-miR-942 or isoforms or variants thereof, can be used as a specific indicative for osteoporosis or risk of osteoporosis Said increase or decrease of miRNAs is specifically based on data derived from blood or serum levels in subjects who were suffering from non-recent fractures.

According to a specific embodiment, hsa-miR-188 is combined with at least one of miRNAs of groups II or III.

According to a further specific embodiment, hsa-miR-382 is combined with at least one of miRNAs of groups II or III.

According to a further specific embodiment, hsa-miR-155 is combined with at least one of miRNAs of groups II or III.

According to a further specific embodiment, hsa-miR-502 is combined with at least one of miRNAs of groups II or III.

According to a further specific embodiment, hsa-miR-136 is combined with at least one of miRNAs of groups II or III.

According to a further specific embodiment, hsa-miR-203 is combined with at least one of miRNAs of groups II or III.

According to a further specific embodiment, hsa-miR-550 is combined with at least one of miRNAs of groups II or III.

Specifically, measuring an increase of the level of group III miRNAs, specifically of two or more of said miRNAs, consisting of hsa-miR-181a-5p, hsa-miR-32-3p, hsa-let-7b-5p, hsa-let-7g-5p, hsa-let-7i-5p, hsa-miR-106a-5p, hsa-miR-106b-5p, hsa-miR-127-3p, hsa-miR-132-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-16-2-3p, hsa-miR-16-5p, hsa-miR-17-5p, hsa-miR-181b-5p, hsa-miR-181c-3p, hsa-miR-181c-5p, hsa-miR-185-5p, hsa-miR-18a-3p, hsa-miR-18a-5p, hsa-miR-18b-5p, hsa-miR-1908, hsa-miR-191-5p, hsa-miR-196b-5p, hsa-miR-199b-5p, hsa-miR-19b-1-5p, hsa-miR-19b-3p, hsa-miR-200b-3p, hsa-miR-203a, hsa-miR-20a-5p, hsa-miR-20b-5p, hsa-miR-210, hsa-miR-21-3p, hsa-miR-25-3p, hsa-miR-26b-5p, hsa-miR-301a-3p, hsa-miR-301b, hsa-miR-323a-3p, hsa-miR-324-5p, hsa-miR-330-3p, hsa-miR-363-3p, hsa-miR-369-3p, hsa-miR-374a-5p, hsa-miR-375, hsa-miR-376c-3p, hsa-miR-378a-5p, hsa-miR-451a, hsa-miR-454-3p, hsa-miR-486-3p, hsa-miR-486-5p, hsa-miR-493-5p, hsa-miR-500a-5p, hsa-miR-532-3p, hsa-miR-545-3p, hsa-miR-550a-3p, hsa-miR-550a-5p, hsa-miR-589-5p, hsa-miR-590-3p, hsa-miR-598, hsa-miR-627, hsa-miR-629-5p, hsa-miR-7-5p, hsa-miR-92a-3p, hsa-miR-93-3p, hsa-miR-93-5p, hsa-miR-941, hsa-miR-942, hsa-miR-96-5p and hsa-miR-98-5p or isoforms or variants thereof can be a specific indicative for osteoporosis or risk for developing osteoporosis or risk of bone lesions or fractures in subjects who are suffering from type II diabetes.

According to a further specific embodiment, hsa-miR-32 is combined with at least one of miRNAs of groups II or III.

According to a further specific embodiment, hsa-miR-486 is combined with at least one of miRNAs of groups II or III.

According to a further specific embodiment, hsa-miR-96 is combined with at least one of miRNAs of groups II or III.

According to a further specific embodiment, hsa-miR-942 is combined with at least one of miRNAs of groups II or III.

Specifically, the measurement or detection of the levels of additional miRNAs consisting of hsa-miR-100, hsa-miR-124a, hsa-miR-148a, hsa-miR-23a, hsa-miR-24, hsa-miR-31, hsa-miR-22-3p and hsa-miR-93 or isoforms or variants thereof in combination with at least two of any of group I, II or III miRNAs can be a further indicative for osteoporosis or risk for developing osteoporosis or risk of bone lesions or fractures in subjects.

Specifically, the measurement or detection of the levels of additional miRNAs consisting of hsa-miR-140-5p, hsa-miR-146a-5p, hsa-miR-199a-5p, hsa-miR-20a, hsa-miR-200a, hsa-miR-217, hsa-miR-218, hsa-miR-26a, hsa-miR-27b, hsa-miR-2861, hsa-miR-29a-3p, hsa-miR-29b-3p, hsa-miR-29c-3p, hsa-miR-204-5p, hsa-miR-335-5p, hsa-miR-34c, hsa-miR-370-3p, hsa-miR-3960, hsa-miR-503-5p, or isoforms and variants thereof in combination with at least two of any of group I, II or III miRNAs can be a further indication for osteoporosis or risk for developing osteoporosis or risk of bone lesions or fractures in subjects.

Specifically, different levels of at least two of miR-188-3p, miR-382-3p, miR-155-5p, and miR-942 compared with the level of healthy subjects are indicative of fracture risk in post-menopausal women without type-2 diabetes. The sensitivity and specificity of the diagnosis of fracture risk and/or osteoporosis in this group of patients can further be improved by including additional miRNA markers selected from hsa-miR-136-3p, hsa-miR-181a-3p, hsa-miR-378a-5p, hsa-miR-502-5p, hsa-miR-550a-5p, hsa-miR-576-3p, and/or hsa-miR-582-3p into the analysis. Specific embodiments, but not limited thereto, are combinations of markers:

miR-188-3p and miR-382-3p;
miR-188-3p, miR-382-3p and miR-942;
miR-188-3p, miR-382-3p, miR-155-5p, and miR-942;
miR-188-3p, miR-382-3p, miR-942, hsa-miR-502-5p and hsa-miR-136-3p;
miR-188-3p, miR-382-3p, miR-942, hsa-miR-582-3p, hsa-miR-576-3p, hsa-miR-136-3p and hsa-miR-502-5p;
miR-188-3p, miR-382-3p, miR-942, hsa-miR-582-3p, hsa-miR-576-3p, hsa-miR-136-3p, hsa-miR-502-5p, hsa-miR-550a-5p;
miR-188-3p, miR-382-3p, miR-942, hsa-miR-582-3p, hsa-miR-576-3p, hsa-miR-136-3p, hsa-miR-502-5p, hsa-miR-550a-5p and hsa-miR-181a-3p;
miR-188-3p, miR-382-3p, miR-942, hsa-miR-582-3p, hsa-miR-576-3p, hsa-miR-136-3p, hsa-miR-502-5p, hsa-miR-550a-5p, hsa-miR-181a-3p and hsa-miR-378a-5p.

According to further alternative embodiments, different levels of at least two of miR-550a-5p, miR-32-3p, miR-96-5p, miR-486-3p compared with the level of healthy subjects are indicative of fracture risk in post-menopausal women suffering from type-2 diabetes. The sensitivity and specificity of the diagnosis of fracture risk and/or osteoporosis in this group of patients can further be improved by including additional miRNA markers selected from hsa-let-7g-5p, hsa-miR-141-3p, hsa-miR-143-5p, hsa-miR-16-2-3p, hsa-miR-181a-5p, hsa-miR-181c-3p, hsa-miR-203a, hsa-miR-323a-3p, hsa-miR-500a-5p, hsa-miR-532-3p, hsa-miR-7-5p, hsa-miR-92a-3p. Specific embodiments, but not limited thereto, are combinations of markers:

miR-550a-5p and miR-32-3p;
miR-550a-5p, miR-32-3p and miR-96-5p;
miR-550a-5p, miR-32-3p, miR-96-5p and miR-486-3p;
miR-550a-5p, miR-32-3p, miR-96-5p, miR-486-3p and hsa-miR-203a;
miR-550a-5p, miR-96-5p hsa-let-7g-5p, hsa-miR-141-3p, hsa-miR-323a-3p and hsa-miR-500a-5p;
miR-550a-5p, miR-96-5p, miR-32-3p hsa-miR-500a-5p, hsa-miR-143-5p, miR 532-3p and hsa-miR-92-3p; miR-550a-5p, miR-96-5p, miR-32-3p, hsa-let-7g-5p, hsa-miR-181a-5p, hsa-miR-203a, hsa-let-7g-5p, hsa-miR-92a-3p;
miR-550a-5p, miR-96-5p, miR-32-3p, hsa-let-7g-5p, hsa-miR-500a-5p, hsa-miR-181c-5p, hsa-miR-16-2-3p, hsa-let-7-5p, hsa-miR-92a-3p;
miR-550a-5p, miR-96-5p, miR-486-3p, miR 532-3p, hsa-miR-500a-5p, hsa-miR-181a-5p, hsa-miR-203a, miR-16-2-3p, hsa-let-7-5p, hsa-miR-32-3p.

As used herein, the term "microRNA" or "miRNA" or "miR" designates a non-coding RNA molecule of between 17 and 25 nucleotides which hybridizes to and regulates the expression of a coding messenger RNA. The term "miRNA molecule" refers to any nucleic acid molecule representing the miRNA, including natural miRNA molecules, i.e. the mature miRNA, pre-miRNA, pri-miRNA.

"miR precursor", "pre-miRNA" or "pre-miR" designates a non-coding RNA having a hairpin structure, which contains a miRNA. A pre-miRNA is the product of cleavage of a primary mi-RNA transcript, or "pri-miR" by the double-stranded RNA-specific ribonuclease known as Drosha. The precursors may be forms of the respective polynucleotides as they occur during maturation of the respective polynucleotides. Specifically, examples of said precursors are listed in tables 2 to 4, specifically they are of SEQ ID Nos. 16 to 30, 78 to 124, 270, 197 to 268, 272 and/or 274.

Nucleotide sequences of mature miRNAs and their respective precursors are known in the art and available from the database miRBase at http://www.mirbase.org/index.shtml or from Sanger database at http://microrna.sanger-.ac.uk/sequences/ftp.shtml. The nucleotide sequences are also specifically disclosed in tables 2 to 4 including reference to the respective gene bank accession numbers.

Identical polynucleotides as used herein in the context of a polynucleotide to be detected or inhibited in context of the present invention may have a nucleic acid sequence with an identity of at least 90%, 95%, 97%, 98% or 99% to a polynucleotide comprising or consisting of the nucleotide sequence of any one of SEQ ID Nos. 1 to 15, 269, 31 to 77, 125 to 196, 271 and/or 273.

Furthermore, identical polynucleotides as used herein in the context of a polynucleotide to be detected or inhibited in context of the present invention may have a nucleic acid sequence with an identity of at least 90%, 95%, 97%, 98% or 99% to a polynucleotide comprising or consisting of the nucleotide sequence of any one of SEQ ID Nos. 1 to 15, 269, 31 to 77, 125 to 196, 271 and/or 273 including one, two, three or more nucleotides of the corresponding pre-miRNA sequence at the 5' end and/or the 3' end of the respective seed sequence.

For the purpose of the invention, "isoforms and variants" (which have also be termed "isomirs") of a reference miRNA include trimming variants (5' trimming variants in which the 5' dicing site is upstream or downstream from the reference miRNA sequence; 3' trimming variants: the 3' dicing site is upstream or downstream from the reference miRNA sequence), or variants having one or more nucleotide modifications (3' nucleotide addition to the 3' end of the reference miRNA; nucleotide substitution by changing nucleotides from the miRNA precursor), or the complementary mature microRNA strand including its isoforms and variants (for example for a given 5' mature microRNA the complementary 3' mature microRNA and vice-versa). With regard to nucleotide modification, the nucleotides relevant for RNA/RNA binding, i.e. the 5'-seed region and nucleotides at the cleavage/anchor side are exempt from modification.

In the following, if not otherwise stated, the term "miRNA" encompasses 3p and 5p strands and also its isoforms and variants.

Specifically, the term "miR-respective_number-3p" as used herein in the specification also encompasses its complementary 5p miRNA and vice versa.

In specific embodiments, the miRNAs of interest are detected using a nucleotide that hybridizes, preferably under stringent conditions, with said miRNA of interest and measuring the hybridization signal.

In a preferred embodiment, the level of the miRNAs of interest is determined by polymerase chain reaction (PCR). PCR methods are well known in the art and widely used, they include quantitative real time PCR, semi-quantitative PCR, multiplex PCR, digital PCR, or any combination thereof. In a particularly preferred embodiment, the levels of miRNAs are determined by quantitative real time PCR (qRT-PCR). Methods of determining the levels of miRNAs using qRT-PCR are known in the art, and are usually preceded by reverse transcription of a miRNA into a cDNA.

In the PCR methods useful in the present invention, the primers are usually based on the mature miRNA molecule, but may include chemical modifications to optimize hybridization behavior.

qRT-PCR methods may determine an absolute level of expression of a miRNA. Alternatively, qRT-PCR methods may determine the relative quantity of a miRNA. The relative quantity of a miRNA may be determined by normalizing the level of the miRNA to the level of one or more internal standard nucleic acid sequences. In general, such internal standard nucleic acid sequences should have a constant level in the analyzed blood or serum sample. For instance, internal standard nucleic acid sequences may be constitutively transcribed RNA nucleic acid sequences such as mRNAs like glyceraldehyde-3-phosphate-dehydrogenase (GAPDH), beta-actin (ACTB), or non-coding RNAs such as 5S and 18S ribosomal RNA, RNU48, RNU44, and RNU6. In addition miRNAs that have constant and high levels in serum or plasma, such as miR-23a-3p, miR-23b-3p, miR-15-5p or miR-16-5p can be used as references for relative quantification. In addition, synthetic RNA sequences added in an equimolar amount during RNA isolation or cDNA synthesis can be used as references for relative quantification of specific miRNAs.

An overview of real time PCR quantification methods useful in the present invention is given by Schmittgen et al., 2008, Methods. January; 44(1): 31-38.

Primers for detection of miRNAs are commercially available, e.g. as microRNA LNA™ PCR primer sets from Exiqon.

Since miRNAs are relatively short molecules, it may be useful, as suggested, e.g. in WO2011/14476, to lengthen them by adding adenosine monomers to the strand (a technique known as polyadenylation) before reverse transcription and amplification. Briefly, the RNA may be extracted from the sample by a suitable reagent (e.g. Trizol reagent), polyadenylated in the presence of ATP and poly(A) polymerase, reverse transcribed into cDNA using a poly(T) adapter and 5' RACE sequence, and amplified using a forward primer derived from the 3' end of the miRNA and a reverse RACE primer. Improvements of this technique include designing the RACE primer with a nucleotide at its 3' end (constituting an A, C, or G, but not a T, so to exclude priming anywhere on the polyA sequence and enforce priming on the miRNA sequence) or RACE primers which are anchored at the 3' cDNA end of a specific microRNA using 2, 3, 4, or more nucleotides with or without chemical modification.

The detection of a miRNA may also be achieved by other methods known in the art, e.g. those described in WO2011/14476, like by the deep sequencing method, bead-based quantification, e.g. Illumina bead-arrays, hydrogel-particle based quantification, e.g. Firefly™, by microarray technology, e.g. the Ncode™ human miRNA array available from Invitrogen, chip arrays available from Affymetrix, Agilent, or microarrays which employ LNA-backbone capture probes (miRCURY LNA™ arrays), e.g., from Exiqon.

The difference in miRNA levels can also be determined using multiplex chemiluminescence-based nucleic acid assays such as Panomics, or reporter plasmid assays ("biosensors") containing reporter proteins with microRNA-complementary regulatory sites, or other hybridization-based techniques known in the art.

The use of miRNAs in a method of the invention is useful for diagnosing bone disorders associated with low bone mineral density (due to aberrant bone metabolism which is reflected in secreted miRNAs) like osteoporosis and, in particular, for assessing the risk of osteoporotic fractures.

The present invention specifically provides a set of miRNAs that represent a diagnostic signature applicable both over a broad range of bone disease stages and age groups. In particular, detection of miRNAs a), which are differentially regulated in the blood or serum of younger patients than those recruited by Seeliger et al., supra, b), which are differentially regulated in patients with non-recent fractures, and/or c), which are differentially regulated in type-2 diabetes patients with non-recent fractures, provides a diagnostic and predictive tool that has a higher significance for early diagnosis, long-term prognosis, and screening of patients with high risk of fractures.

Biomarkers with prognostic value for disease progression are of utmost importance to minimize the occurrence of severe osteoporotic fractures. Currently, a high incidence in osteoporotic fractures can be attributed to unspecific diagnostic methods that are largely based on bone imaging and routine clinical parameters and overt characteristics such as sex, age, life style and family history and FRAX™ scores. Evaluation of these parameters are however, not directly relevant for bone metabolism and osteoblast/osteoclast activity. Therefore high variation in the individual fracture-risk persists, albeit general guidelines that involve FRAX™ and BMD. Early diagnosis using microRNAs relies on a read out of bone metabolism and thus the pathophysiology of the diseases itself. This analysis is therefore more specific to the individual patient.

According to another aspect, the invention relates to therapeutical compositions for the treatment of bone fractures and bone disorders like osteoporosis, or in the context of type-2 diabetes, in particular for the prevention or healing of fractures.

Specifically, a composition can comprise a. at least one, specifically at least two isolated or synthetic human miRNAs from miRNAs hsa-miR-382-3p, hsa-miR-181a-5p, hsa-miR-32-3p, hsa-let-7b-5p, hsa-let-7g-5p, hsa-let-7i-3p, hsa-let-7i-5p, hsa-miR-106a-5p, hsa-miR-106b-5p, hsa-miR-10a-5p, hsa-miR-10b-5p, hsa-miR-1227-

3p, hsa-miR-125b-5p, hsa-miR-127-3p, hsa-miR-132-3p, hsa-miR-133a, hsa-miR-133b, hsa-miR-135a-5p, hsa-miR-136-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-155-5p, hsa-miR-16-2-3p, hsa-miR-16-5p, hsa-miR-17-5p, hsa-miR-181a-3p, hsa-miR-181b-5p, hsa-miR-181c-3p, hsa-miR-181c-5p, hsa-miR-185-5p, hsa-miR-188-3p, hsa-miR-18a-3p, hsa-miR-18a-5p, hsa-miR-18b-5p, hsa-miR-1908, hsa-miR-190a, hsa-miR-191-5p, hsa-miR-192-5p, hsa-miR-193b-3p, hsa-miR-194-5p, hsa-miR-196b-5p, hsa-miR-199b-5p, hsa-miR-19b-1-5p, hsa-miR-19b-3p, hsa-miR-200b-3p, hsa-miR-203a, hsa-miR-205-5p, hsa-miR-20a-5p, hsa-miR-20b-5p, hsa-miR-210, hsa-miR-21-3p, hsa-miR-214-3p, hsa-miR-215, hsa-miR-223-5p, hsa-miR-25-3p, hsa-miR-26b-5p, hsa-miR-27a-3p, hsa-miR-301a-3p, hsa-miR-301b, hsa-miR-30a-5p, hsa-miR-30e-3p, hsa-miR-323a-3p, hsa-miR-324-5p, hsa-miR-328-3p, hsa-miR-330-3p, hsa-miR-342-5p, hsa-miR-363-3p, hsa-miR-369-3p, hsa-miR-374a-5p, hsa-miR-375, hsa-miR-376a-3p, hsa-miR-376c-3p, hsa-miR-377-3p, hsa-miR-378a-5p, hsa-miR-409-3p, hsa-miR-410, hsa-miR-451a, hsa-miR-454-3p, hsa-miR-486-3p, hsa-miR-486-5p, hsa-miR-487b, hsa-miR-493-5p, hsa-miR-495-3p, hsa-miR-500a-5p, hsa-miR-502-5p, hsa-miR-532-3p, hsa-miR-542-5p, hsa-miR-545-3p, hsa-miR-548a-3p, hsa-miR-550a-3p, hsa-miR-550a-5p, hsa-miR-574-3p, hsa-miR-576-3p, hsa-miR-582-3p, hsa-miR-589-5p, hsa-miR-590-3p, hsa-miR-598, hsa-miR-624-5p, hsa-miR-627, hsa-miR-629-5p, hsa-miR-642a-5p, hsa-miR-7-5p, hsa-miR-92a-3p, hsa-miR-93-3p, hsa-miR-93-5p, hsa-miR-941, hsa-miR-942, hsa-miR-96-5p, hsa-miR-98-5p or isoforms and variants thereof and/or b. an antagonist/inhibitor of at least one, specifically at least two of miRNAs of hsa-miR-382-3p, hsa-miR-181a-5p, hsa-miR-32-3p, hsa-let-7b-5p, hsa-let-7g-5p, hsa-let-7i-3p, hsa-let-7i-5p, hsa-miR-106a-5p, hsa-miR-106b-5p, hsa-miR-10a-5p, hsa-miR-10b-5p, hsa-miR-1227-3p, hsa-miR-125b-5p, hsa-miR-127-3p, hsa-miR-132-3p, hsa-miR-133a, hsa-miR-133b, hsa-miR-135a-5p, hsa-miR-136-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-155-5p, hsa-miR-16-2-3p, hsa-miR-16-5p, hsa-miR-17-5p, hsa-miR-181a-3p, hsa-miR-181b-5p, hsa-miR-181c-3p, hsa-miR-181c-5p, hsa-miR-185-5p, hsa-miR-188-3p, hsa-miR-18a-3p, hsa-miR-18a-5p, hsa-miR-18b-5p, hsa-miR-1908, hsa-miR-190a, hsa-miR-191-5p, hsa-miR-192-5p, hsa-miR-193b-3p, hsa-miR-194-5p, hsa-miR-196b-5p, hsa-miR-199b-5p, hsa-miR-19b-1-5p, hsa-miR-19b-3p, hsa-miR-200b-3p, hsa-miR-203a, hsa-miR-205-5p, hsa-miR-20a-5p, hsa-miR-20b-5p, hsa-miR-210, hsa-miR-21-3p, hsa-miR-214-3p, hsa-miR-215, hsa-miR-223-5p, hsa-miR-25-3p, hsa-miR-26b-5p, hsa-miR-27a-3p, hsa-miR-301a-3p, hsa-miR-301b, hsa-miR-30a-5p, hsa-miR-30e-3p, hsa-miR-323a-3p, hsa-miR-324-5p, hsa-miR-328-3p, hsa-miR-330-3p, hsa-miR-342-5p, hsa-miR-363-3p, hsa-miR-369-3p, hsa-miR-374a-5p, hsa-miR-375, hsa-miR-376a-3p, hsa-miR-376c-3p, hsa-miR-377-3p, hsa-miR-378a-5p, hsa-miR-409-3p, hsa-miR-410, hsa-miR-451a, hsa-miR-454-3p, hsa-miR-486-3p, hsa-miR-486-5p, hsa-miR-487b, hsa-miR-493-5p, hsa-miR-495-3p, hsa-miR-500a-5p, hsa-miR-502-5p, hsa-miR-532-3p, hsa-miR-542-5p, hsa-miR-545-3p, hsa-miR-548a-3p, hsa-miR-550a-3p, hsa-miR-550a-5p, hsa-miR-574-3p, hsa-miR-576-3p, hsa-miR-582-3p, hsa-miR-589-5p, hsa-miR-590-3p, hsa-miR-598, hsa-miR-624-5p, hsa-miR-627, hsa-miR-629-5p, hsa-miR-642a-5p, hsa-miR-7-5p, hsa-miR-92a-3p, hsa-miR-93-3p, hsa-miR-93-5p, hsa-miR-941, hsa-miR-942, hsa-miR-96-5p, hsa-miR-98-5p, or isoforms and variants thereof that
  i decreases the level of said miRNAs; and/or
  ii inhibits or down-regulates expression of the sequences coding for said miRNAs or degrades or cleaves said miRNAs, specifically selected from ribozymes.

According to another aspect, the composition further contains one or more miRNAs selected from hsa-miR-140-5p, hsa-miR-146a-5p, hsa-miR-199a-5p, hsa-miR-20a, hsa-miR-200a, hsa-miR-217, hsa-miR-218, hsa-miR-26a, hsa-miR-27b, hsa-miR-2861, hsa-miR-29a-3p, hsa-miR-29b-3p, hsa-miR-29c-3p, hsa-miR-204-5p, hsa-miR-335-5p, hsa-miR-34c, hsa-miR-370-3p, hsa-miR-3960, hsa-miR-503-5p, or isoforms and variants thereof, as defined herein, or inhibitors or antagonists thereof that decrease the level of said miRNAs; and/or
inhibits or down-regulates expression of the sequences coding for said miRNAs or degrades or cleaves said miRNAs, specifically selected from ribozymes.

According to another aspect, the composition further contains one or more miRNAs selected from hsa-miR-188-3p, hsa-miR-382-3p, hsa-miR-942, hsa-miR-155-5p, optionally in combination with hsa-miR-136-3p, hsa-miR-181a-3p, hsa-miR-378a-5p, hsa-miR-502-5p, hsa-miR-550a-5p, hsa-miR-576-3p, hsa-miR-582-3p or isoforms and variants thereof, as defined herein, or inhibitors or antagonists thereof that decrease the level of said miRNAs; and/or
inhibits or down-regulates expression of the sequences coding for said miRNAs or degrades or cleaves said miRNAs, specifically selected from ribozymes.

According to yet another aspect the composition further contains one or more miRNAs selected from miR-550a-5p, miR-32-3p, miR-96-5p, miR-486-3p, optionally in combination with hsa-let-7g-5p, hsa-miR-141-3p, hsa-miR-143-5p, hsa-miR-16-2-3p, hsa-miR-181a-5p, hsa-miR-181c-3p, hsa-miR-203a, hsa-miR-323a-3p, hsa-miR-500a-5p, hsa-miR-532-3p, hsa-miR-7-5p, hsa-miR-92a-3p 3p or isoforms and variants thereof, as defined herein, or inhibitors or antagonists thereof that decrease the level of said miRNAs; and/or
inhibits or down-regulates expression of the sequences coding for said miRNAs or degrades or cleaves said miRNAs, specifically selected from ribozymes.

These miRNAs or their inhibitors/antagonists respectively, may be used in combination with the miRNAs listed in the paragraph above or as single components or in any combination thereof.

Whether the miRNA itself or an inhibitor/antagonist thereof is incorporated as the active ingredient in the therapeutical composition not only depends on whether such miRNA is up- or down-regulated in a patient at risk of an osteoporotic fracture, but on its specific function in osteogenic differentiation or in osteoclastogenic activation. By way of example, if a miRNA, which functions as an inhibitor of osteogenic differentiation, is found upregulated in osteoporosis, as shown in table 1 or specifically, as known for miR 31-5p, or if it functions as a promoter of osteoclastogenesis like miR-148a-5p, an inhibitor/antagonist of such miRNA will be the active ingredient in the composition of the invention.

In the following, if not otherwise stated, the term "miRNA therapeutic" is used for both the miRNA itself and the respective miRNA inhibitor/antagonist.

A miRNA therapeutic is generally based on the sequence of the targeted mature miRNA. Therapeutics for miRNA replacement therapies need to share most of the sequence of the mature miRNA which is substituted. Exact sequence homology is required in the 5' seed region of the miRNA. Therapeutics designed to specifically inhibit miRNA function (anti-microRNA oligonucleotides, AMO) need to be complementary to the targeted sequence so that a stable hybridization and hence sequestration of the miRNA is achieved. AMOs may contain chemical modifications which cause stable RNA duplex formation, such as a phosphorothioate backbone, or LNA and 2'OMe modifications of the sugar residues, respectively.

Whether a miRNA that is up- or downregulated in serum/plasma of subjects with bone disorders, may be causally related to the disease due to its function in bone formation, can be determined by assessing the effect of these miRNAs on osteogenic differentiation: synthetic microRNA transfection in mesenchymal stem cells is performed prior to the initiation of osteogenic differentiation. Using assays that quantitate the early osteogenic marker alkaline phosphatase (ALP), e.g. by qPCR, western blot, or enzymatically, or assays determining calcium deposition, e.g. by Alizarin staining, as described by Deng et al. (Deng et al., 2014), conclusions about the importance of a miRNA for bone formation can be drawn.

Alternatively, a miRNA therapeutic may be routinely tested for usefulness in the present invention by transfecting MSCs or, as a model for MSCs, adipose tissue-derived stem cells (ASCs), with mammalian vector constructs containing the DNA sequence encoding the miRNA therapeutic and determining its effect on osteogenic differentiation as described above.

MSCs and ASCs may be obtained by known methods, e.g. as described by Wolbank et al., 2007 (Tissue Eng 13, 1173-1183) and Wolbank et al., 2009 (Tissue Eng Part A 15, 1843-1854).

A miRNA that is confirmed to be involved in bone regeneration and thus to promote bone healing, is useful as the active ingredient in a pharmaceutical composition of the invention.

Whether a miRNA that is up- or downregulated in serum/plasma of subjects with bone disorders, may be causally related to the disease due to its function in bone resorption, can be determined by assessing the effect of these miRNAs on osteoclast formation: synthetic microRNA transfection in CD14+ peripheral blood mononuclear cells is performed prior to the initiation of osteoclast formation through RANKL and M-CSF. Using assays that quantitate osteoclast markers such as tartrate-resistant acid phosphatase (TRAP) activity, Calcitonin receptor and RANK expression, conclusions about the importance of a miRNA for bone resorption can be drawn. A miRNA can be obtained from a miR precursor using intact cells or cell lysates or it can be produced in vitro using isolated processing enzymes, such as isolated Drosha/Dgcr8 and Dicer. A miRNA may also be produced by chemical synthesis, without having been processed from a miR precursor.

Antagonists/inhibitors of miRNAs are well known in the art and customized miRNA inhibitors are commercially available. For example, antagonists/inhibitors of in context of the present invention may be nucleic acid molecules such as antagomiRs (Kriitzfeldt, Nature (2005), 438: 685-689) or any other T-O-methyl-RNA oligonucleotide having phosphorothioates bonds and a cholesterol tail, miRCURY LNA™ microRNA inhibitors (Exiqon), in vivo LNA™ miRNA inhibitors (Exiqon), tiny LNAs (Obad, Nat Genet (2011), 43(4): 371-378), miR-decoys or miR-sponges (Ebert, Nat Methods (2007), 4: 721-726; Bond, Nat Med (2008), 14: 1271-1277) or the like. An antagonist/inhibitor might also be or derived from miRNA degrading enzymes as described in Chatterjee, Nature (2009), 461: 546-9, hammerhead ribozymes as described in Tedeschi, Drug Discov Today (2009), 14: 776-783, or antogomirzymes as described in Jadhav, Angew Chem Int Ed Engl (2009), 48(14): 2557-2560. In context of the present invention, the antagmiRs, miCURY LNA™ microRNA inhibitors, in vivo LNA™ miR inhibitors, tiny LNAs, miR decoys or miR sponges.

In a further embodiment, the active ingredient of the pharmaceutical composition is selected according to the principles of so-called "personalized medicine", i.e. correlated with the results of the diagnostic method of the invention, which would, in this case, be a so-called "companion" diagnostic. This means that the decision over therapeutic administration of a miRNA with the aim to either substitute or inhibit a specific miRNA, is closely linked to an accompanying diagnostic procedure where the level of the specific miRNA is analyzed in an individual.

Osteoclast-specific promoters such as Calcitonin receptor (CalcR), RANK (receptor activator of NFkB), colony stimulating factor 1 receptor (c-Fms), and Cathepsin K (CathK) may be used.

In embodiments of local administration, e.g. for accelerating bone healing after a fracture, the nucleic acid molecule encoding the miRNA therapeutic may be delivered to the site of interest by means of viral or nonviral vectors or as naked DNA or RNA. As reviewed by Pelled et al., 2010 (Tissue Engineering: Part B, Volume 16, No. 1, 13-20), localization of the therapeutic molecule within the fracture site may be assured either by physical placement at the target site or by gene release from a three dimensional biomaterial implanted at or near the defect area, including biological glues such as polymers of fibrinogen and thrombin. Useful physical placement methods include direct injection of the miRNA, or lipid-microRNA complexes formed from agents such as Polyethylenimine (PEI) therapeutic into the fracture site. Preferably, in order for the nucleic acid molecule to penetrate cells in situ, it is delivered in complexed state using such as liposomes or PEI. Alternatively, the miRNA could be transcribed by a virus. Preferably, an adenoviral vector is used, as described for expressing bone morphogenetic protein (BMP) by Egermann et al., 2006 (Hum Gene Ther. May; 17 (5):507-17).

Alternatively to using a vector, in vivo electroporation or sonoporation may be used to deliver the therapeutic locally. Using these methods, the miRNA or the miRNA-encoding DNA molecule is directly injected into a fracture and an electric pulse or ultrasonic wave is applied to the site either trans- or percutaneously. Said miRNAs or antagonists/inhibitors thereof may also be part of fibrin sealants, specifically used for bone repair and regeneration.

In a further embodiment, mesenchymal stem cells derived from any source, including but not limited to bone marrow, adipose tissue, umbilical tissue, urine, or placenta, genetically engineered to overexpress or suppress the therapeutic miRNA may be implanted at the defect site (Marie, 2011, Osteoporos Int 22:2023-2026, Deng et al., supra).

In an alternative embodiment, localizing the miRNA therapeutic at the site of interest, e.g. the fracture site, e.g. by transgene expression, is achieved by first binding the miRNA therapeutic DNA/RNA to a delivery system (e.g. by adsorption, entrapment or immobilization, or by covalent binding; Luginbuehl et al., 2004, Eur J Pharm Biopharm 58:197-208) and then implanting the gene-activated matrix (GAM) into the defect site, e.g. as described by Fang et al., 1996 (Proc Natl Acad Sci USA 93, 5753).

Useful matrices (GAMs, "gene-activated matrices") have been described in the context with matrices for the delivery of the miRNA. Also when the therapeutically active miRNA or an inhibitor/antagonist thereof is administered locally, either as such or incorporated in a matrix, it may advantageously be linked to a bone-targeting molecule. This may be accomplished by linking the delivery vehicle, e.g. a liposome, which is used to complex the miRNA therapeutic, with the bone-targeting molecule. In the case that a nucleic acid molecule is to be administered locally, incorporation of the bone-targeting molecule is achieved by linking it to the surface of the delivery vehicle. The same applies for a CPP.

Any miRNA therapeutic of the invention, either containing the miRNA molecule or the nucleic acid molecule encoding it, or an antisense inhibitor, may be combined with one or more other agents e.g. teriparatide, denosumab, blosozumab, romosozumab, bisphosphonates such as alendronate, zolendronate, or one or more bone growth factors or the respective encoding nucleic acid molecules, e.g. a BMP like BMP-2 and/or BMP-7, or RNAs, like e.g. RNAs antagonizing miR-31.

The invention furthermore comprises the following items:

1. An in vitro method of diagnosing osteoporosis or determining the risk of osteoporotic fractures or monitoring of treatment success in a subject, comprising the steps of:
   a) providing a blood sample from said subject;
   b) measuring the level of two or more miRNAs selected from any of
      i. group II miRNAs consisting of hsa-miR-188-3p, hsa-miR-382-3p, hsa-let-7i-3p, hsa-miR-1227-3p, hsa-miR-127-3p, hsa-miR-133b, hsa-miR-135a-5p, hsa-miR-136-3p, hsa-miR-143-3p, hsa-miR-155-5p, hsa-miR-181a-3p, hsa-miR-1908, hsa-miR-190a, hsa-miR-192-5p, hsa-miR-193b-3p, hsa-miR-196b-5p, hsa-miR-199b-5p, hsa-miR-200b-3p, hsa-miR-203a, hsa-miR-205-5p, hsa-miR-20b-5p, hsa-miR-214-3p, hsa-miR-215, hsa-miR-223-5p, hsa-miR-27a-3p, hsa-miR-30e-3p, hsa-miR-323a-3p, hsa-miR-330-3p, hsa-miR-342-5p, hsa-miR-369-3p, hsa-miR-376c-3p, hsa-miR-377-3p, hsa-miR-378a-5p, hsa-miR-410, hsa-miR-454-3p, hsa-miR-487b, hsa-miR-495-3p, hsa-miR-500a-5p, hsa-miR-502-5p, hsa-miR-542-5p, hsa-miR-548a-3p, hsa-miR-550a-5p, hsa-miR-576-3p, hsa-miR-582-3p, hsa-miR-624-5p, hsa-miR-642a-5p, hsa-miR-941, hsa-miR-942 or isoforms or variants thereof, and/or
      ii. group III miRNAs consisting of hsa-miR-181a-5p, hsa-miR-32-3p, hsa-let-7b-5p, hsa-let-7g-5p, hsa-let-7i-5p, hsa-miR-106a-5p, hsa-miR-106b-5p, hsa-miR-127-3p, hsa-miR-132-3p, hsa-miR-140-3p, hsa-miR-141-3p, hsa-miR-143-3p, hsa-miR-143-5p, hsa-miR-144-3p, hsa-miR-146b-5p, hsa-miR-154-5p, hsa-miR-16-2-3p, hsa-miR-16-5p, hsa-miR-17-5p, hsa-miR-181b-5p, hsa-miR-181c-3p, hsa-miR-181c-5p, hsa-miR-185-5p, hsa-miR-18a-3p, hsa-miR-18a-5p, hsa-miR-18b-5p, hsa-miR-1908, hsa-miR-191-5p, hsa-miR-196b-5p, hsa-miR-199b-5p, hsa-miR-19b-1-5p, hsa-miR-19b-3p, hsa-miR-200b-3p, hsa-miR-203a, hsa-miR-20a-5p, hsa-miR-20b-5p, hsa-miR-210, hsa-miR-21-3p, hsa-miR-25-3p, hsa-miR-26b-5p, hsa-miR-301a-3p, hsa-miR-301b, hsa-miR-323a-3p, hsa-miR-324-5p, hsa-miR-330-3p, hsa-miR-363-3p, hsa-miR-369-3p, hsa-miR-374a-5p, hsa-miR-375, hsa-miR-376c-3p, hsa-miR-378a-5p, hsa-miR-451a, hsa-miR-454-3p, hsa-miR-486-3p, hsa-miR-486-5p, hsa-miR-493-5p, hsa-miR-500a-5p, hsa-miR-532-3p, hsa-miR-545-3p, hsa-miR-550a-3p, hsa-miR-550a-5p, hsa-miR-589-5p, hsa-miR-590-3p, hsa-miR-598, hsa-miR-627, hsa-miR-629-5p, hsa-miR-7-5p, hsa-miR-92a-3p, hsa-miR-93-3p, hsa-miR-93-5p, hsa-miR-941, hsa-miR-942, hsa-miR-96-5p, hsa-miR-98-5p or isoforms or variants thereof and/or
      iii. group I miRNAs consisting of hsa-miR-10a-5p, hsa-miR-10b-5p, hsa-miR-125b-5p, hsa-miR-127-3p, hsa-miR-133a, hsa-miR-133b, hsa-miR-143-3p, hsa-miR-18a-3p, hsa-miR-194-5p, hsa-miR-30a-5p, hsa-miR-328-3p, hsa-miR-376a-3p, hsa-miR-409-3p, hsa-miR-574-3p, or isoforms or variants thereof
   in said blood sample and either
   c) comparing the level of said miRNAs with the level of the corresponding miRNA in a reference blood sample from a healthy individual,
   wherein a difference by more than 1.5 fold in said level when compared to the reference sample is indicative of osteoporosis and an elevated risk of osteoporotic fractures or
   d) comparing the level of said miRNAs with the average level of corresponding miRNAs in healthy subjects, wherein a difference by more than one standard deviations is indicative of osteoporosis with an increased risk of future osteoporotic fractures.

2. The method according to item 1, wherein the difference of more than 2.5-fold is indicative of osteoporosis with a high risk of future osteoporotic fractures.

3. The method according to item 1 or 2, wherein the level of said two or more human miRNAs are selected from group I miRNAs.

4. The method according to item 1 to 3, wherein the level of said two or more human miRNAs are selected from group II miRNAs.

5. The method according to item 1 to 4, wherein the level of said two or more human miRNAs are selected group III miRNAs.

6. The method according to any one of items 1 to 5, wherein the level of at least three, preferably at least four, preferably at least 5 miRNAs of any of groups I, II or III is measured.

7. The method according to item 1 or 2, wherein the level of all miRNAs of any of group I and/or group II and/or group III miRNAs is measured.

8. The method according to any one of items 1 or 2, wherein the levels of hsa-miR-127-3p, hsa-miR-133b, hsa-miR-143-3p, are measured.

9. The method according to any one of items 1 or 2, wherein the level of hsa-miR-106a-5p, hsa-miR-127-3p, hsa-miR-133b, hsa-miR-143-3p, hsa-miR-18a-3p, hsa-miR-196b-5p, hsa-miR-199b-5p, hsa-miR-200b-3p, hsa-miR-203a, hsa-miR-20b-5p, hsa-miR-323a-3p, hsa-miR-330-3p, hsa-miR-369-3p, hsa-miR-376c-3p, hsa-miR-378a-5p, hsa-miR-454-3p, hsa-miR-500a-5p, hsa-miR-550a-5p, hsa-miR-941, and hsa-miR-942 are measured.

10. The method according to item 1 or 2, wherein the levels of at least two of hsa-miR-188-3p, hsa-miR-382-3p, hsa-miR-942, hsa-miR-155-5p are measured.

11. The method according to item 10, wherein the levels of at least one further miR selected from the group consisting of hsa-miR-136-3p, hsa-miR-181a-3p, hsa-miR-378a-5p, hsa-miR-502-5p, hsa-miR-550a-5p, hsa-miR-576-3p, hsa-miR-582-3p are measured.

12. The method according to item 1 or 2, wherein the levels of at least two of miR-550a-5p, miR-32-3p, miR-96-5p, miR-486-3p are measured.

13. The method according to item 12, wherein the levels of at least one further miRNA selected from the group consisting of hsa-let-7g-5p, hsa-miR-141-3p, hsa-miR-143-

5p, hsa-miR-16-2-3p, hsa-miR-181a-5p, hsa-miR-181c-3p, hsa-miR-203a, hsa-miR-323a-3p, hsa-miR-500a-5p, hsa-532-3p, hsa-miR-7-5p, hsa-miR-92a-3p is measured.

14. The method according to any one of items 1 to 13, wherein one or more further miRNAs are detected, said miRNAs being differentially regulated in osteoporotic individuals as compared to healthy individuals and involved in osteogenic differentiation and/or in osteoclastogenic activation.

15. The method according to any one of items 1 to 14, wherein said further miRNAs are selected from group IV miRNAs, consisting of hsa-miR-100, hsa-miR-124a, hsa-miR-148a, hsa-miR-23a, hsa-miR-24, hsa-miR-31, hsa-miR-22-3p and hsa-miR-93.

16. The method according to any one of items 1 to 15, wherein said further miRNAs are selected from group V miRNAs, consisting of hsa-miR-140-5p, hsa-miR-146a-5p, hsa-miR-199a-5p, hsa-miR-20a, hsa-miR-200a, hsa-miR-217, hsa-miR-218, hsa-miR-223, hsa-miR-26a, hsa-miR-27b, hsa-miR-2861, hsa-miR-29a-3p, hsa-miR-29b-3p, hsa-miR-29c-3p, hsa-miR-204-5p, hsa-miR-335-5p, hsa-miR-34c, hsa-miR-370-3p, hsa-miR-3960, hsa-miR-503-5p, or isoforms and variants thereof.

17. Use of a method according to any one of items 1 to 16 for monitoring a subject.

18. Use of a method according to any one of items 1 to 16 for the prognosis of bone fraction.

19. The method according to any one of items 1 to 16, wherein the subjects are osteoporosis patients suffering from or being at risk of developing bone fractures, or patients being at risk of or suffering from type 2 diabetes mellitus.

20. The method according to any one of items 1 to 16, wherein the difference in miRNA levels is determined by quantitative or digital PCR, sequencing, microarray, Luminex nucleic acid assays, or other hybridization-based techniques.

21. Composition for use in treating or preventing osteoporosis or fractures comprising
at least two synthetic human miRNAs from miRNA groups I, II or III and/or
an antagonist/inhibitor of at least two of miRNAs of groups I, II or III that decreases the level of said miRNAs; and/or inhibits or down-regulates expression of the sequences coding for said miRNAs or degrades said miRNAs or degrades or cleaves said miRNAs.

22. Composition according to item 21 for use in the preparation of a medicament.

23. Method for treating or preventing osteoporosis or fractures in a subject, comprising administering an effective amount of
at least two isolated human miRNAs from miRNA groups I, II or III and/or
an antagonist/inhibitor of at least two of miRNAs of groups I, II or III that
a. decreases the level of said miRNAs; and/or
b. inhibits or down-regulates expression of the sequences coding for said miRNAs or degrades said miRNAs or degrades or cleaves said miRNAs.

The examples described herein are illustrative of the present invention and are not intended to be limitations thereon. Different embodiments of the present invention have been described according to the present invention. Many modifications and variations may be made to the techniques described and illustrated herein without departing from the spirit and scope of the invention. Accordingly, it should be understood that the examples are illustrative only and are not limiting upon the scope of the invention.

EXAMPLES

Example 1: Circulating microRNAs in Response to Recent Femoral-Neck Fractures

Study Design

For the analysis of miRNAs in recent fractures the focus was put on patients younger than those selected by Seeliger et al., 2014, supra, since diagnosis preferentially occurs early during disease development, i.e. at younger age.

Ethical approval was granted by the upper Austrian ethics committee for the collection of serum samples from 14 subjects by centrifugation at room temperature at 2000×g for 15 minutes after incubation at room temperature for 30 minutes. Subjects were classified into two groups (n=7) based on prior occurrence of osteoporotic femoral fractures (FIG. 1a). Of the analyzed characteristics such as age, body mass index (BMI), sampling interval after surgery, BMD T-Score, Vitamin D and PTH, only BMI showed significant differences.

RNA Isolation

Serum samples were frozen at −80° C. for long term storage. Upon RNA isolation, serum was thawed at 37° C., centrifuged at 12.000×g for 5 minutes to remove cellular debris and 200 µl serum were homogenized in 750 µl Qiazol containing 35 fmol synthetic cel-miR-39-3p spike-in control. RNA isolation was performed using chloroform and the miRNeasy isolation kit (Qiagen, Germany) for RNA precipitation and purification with the following deviations from the standard protocol: 200 µl plasma were homogenized in 750 µl Qiazol. Exactly 500 µl aqueous phase were taken, 1 µl Glycogen (Ambion, Tex.) was added to a final concentration of 50 µg/ml and precipitated with 750 µl 100% Ethanol. Columns were washed three times with RPE buffer and plasma-RNA was eluted once in 30 µl nuclease-free water and stored at −80° C. Quantitation of cel-miR-39-3p was performed in quadruplicates on a Qiagen Rotorgene using the respective Taqman microRNA Assay Kit and Mastermix (Applied Biosystems).

qPCR Analysis

Screening of miRNA expression was performed by Exiqon Inc. in Denmark using 384-well serum/plasma focus panels, which cover 175 distinct human miRNAs that have been repeatedly found to circulate in serum or plasma. First, 4 µl of isolated RNA were reverse transcribed in 20 µl reactions using the miRCURY LNA Universal RT reaction kit. UniSp3 and UniSp6 are synthetic controls that were added at this step and subsequently analyzed to detect presence of enzyme inhibitors. RT-reactions were diluted 50-fold prior to qPCR analysis and each miRNA was assayed once per sample in a 10 µl reaction using the Roche LC 480 Real-Time PCR System (Roche, Germany).

Data Analysis

Melting curve analysis was performed and miRNA PCR reactions with more than one peak were excluded from the analysis. Amplification efficiencies were calculated using algorithms similar to the linreg software package. Efficiencies ranged between 1.8 and 2.1 for most miRNAs. Individual reactions that gave efficiencies <1.6 were excluded from the dataset. Background levels for each miRNA were generated by assaying a "no template" cDNA synthesis control on a full serum/plasma focus panel plate. The majority of miRNA assays did not yield any signal and background Cp was set to 42. We required every miRNA assay to exhibit signals >5 Cps lower than the background value to be included in the analysis. Normalization of Cp-values was performed based on the average Cp of the miRNA assays detected across all 14 samples (124 assays). Normfinder software was used to confirm that the stability of the average Cp was higher than the stability of any individual miRNA assay in the data set. The following equation was used for normalization: normalized Cp (dCp)=average Cp (124 assays)−assay Cp (sample). This results in a delta Cp (dCp) value, which is a relative $\log_2$-transformed measure for expression where higher values indicate a higher concentration and lower dCp values indicate lower concentration in plasma.

Non-parametric t-statistics were calculated using the Mann-Whitney U test and fold changes between the average expression values for each group were calculated. In total, fifteen miRNAs showed a high difference (Fold Change >1.5) between recent fracture and control samples.

Example 2: Circulating microRNAs in Patients with Prevalent or Incident Non-Recent Osteoporotic Fractures with and without Type-2 Diabetes Study Design for Prevalent Osteoporotic Fractures Serum samples of 74 postmenopausal women (17 controls without fracture history (Co), 19 controls with history of fragility fractures (Fx), 19 type 2 diabetic women without fractures (DM) and 19 type 2 diabetic women with history of fragility fractures (DMFx)) have been collected during the study conduct. To be included in the study, all women had to be postmenopausal, aged 50-75 with a body mass index ranging from 18 to 37 kg/m2. All subjects were required to be mobile and able to move without walkers. For subjects enrolled in the diabetic group, a minimum of 3 years history of treatment for type 2 diabetes by oral medications and/or insulin was required. Caucasian, Asian and African-American women were included. Subjects with fractures were only included if the fractures were caused by a low energy trauma such as falls from standing height or less and if they were sustained after menopause. Patients with pathologic fractures of other origin such as local tumors, tumour-like lesions or focal demineralizations as visualized on radiographs were excluded from the study.

Exclusion criteria comprised all medical conditions that could affect bone metabolism such as severe neuropathic disease, juvenile or premenopausal idiopathic osteoporosis, hyperthyroidism, hyperparathyroidsm, a recent history of longer (>3 months) periods of immobilization, chronic drug use, alcoholism, chronic gastrointestinal disease, significant chronic renal impairment (CKD stages IV and V), significant chronic hepatic impairment, unstable cardiovascular disease or uncontrolled hypertension. In addition any chronic treatment over the last six months with adrenal or anabolic steroids, estrogens, antacids, anticonvulsants, anticoagulants, pharmacological doses of Vitamin A, fluorides, bisphosphonates, calcitonin, tamoxifen or parathyroid hormone (PTH) was considered a criterion for exclusion. Due to their proven impact on bone mass and bone structure subjects who were on anti-diabetic agents such as rosiglitazone or pioglitazone were also excluded from the study.

The study protocol was approved by the UCSF Committee of Human Research (CHR) and all patients gave written informed consent before participation. Blood specimens were collected between 8 and 11 am after 12 hours of overnight fasting according to the laboratory's handling instructions. For serum samples, blood was allowed to clot in an upright position for 40 minutes and then centrifuged at 2500 rpm for 15 min within one hour of collection. None of the samples showed signs of hemolysis on visual inspection. Serum was subsequently transferred to 1.5 ml plastic screw-cap vials and stored at −80° C. until further analysis.

Study Design for Incident Osteoporotic Fractures

A prospective nested case-control study-design with 443 postmenopausal women over age 66 from the AGES-Reykjavik cohort was generated. The aim of this study was the identification of circulating microRNAs for the prediction of first osteoporotic fractures (incident fracture) or additional osteoporotic fractures. For that purpose blood samples are analyzed at baseline for serum microRNA levels and correlated with the patient outcome after the first follow up at 5.4 years. In total the study design included 4 groups: a control group comprising 100 healthy individuals without prevalent fractures and who did not sustain fractures during the 5.4 year follow-up, a fracture group comprising 172 patients of which 100 had sustained a first incident fracture during the follow up and 72 patients who already had one or more prevalent fractures before sustaining an additional fracture during the follow-up period, a control diabetic group comprising 100 individuals that had been diagnosed with type-2 diabetes but did not have prevalent or sustain incident fractures during the follow up, and a diabetic fracture group consisting of 71 patients of which 35 had sustained a first incident fracture within the 5.4 year follow-up and 36 patients who had prevalent fracture at baseline and one or more additional incident fractures during the follow up period.

In fracture groups, patients with high energy trauma and stressfractures were excluded. Prevalent fractures that had happened 18 months before study visit or less were excluded. Only subjects were included that exhibited kidney functions above 30 ml/min (eGFR), a BMI of >20 kg/m2, no history of longstanding or recent immobilization, no current intake of bone affecting medications and no self-reported or medical record based evidence of kidney disease, liver disease, chronic gastrointestinal disease, hyperparathyroidism, ovariectomy, chronic alcoholism, or idiopathic osteoporosis.

RNA Isolation

For RNA isolation, 200 µl serum were thawed at 37° C., centrifuged at 12,000×g for 5 minutes and homogenized in 1000 µl Qiazol containing synthetic RNA spike-in controls (Exiqon, Denmark) at three different concentrations to monitor the efficiency of small RNA purification. RNA isolation was performed using chloroform extraction and the miRNeasy isolation kit (Qiagen, Germany) for RNA precipitation and purification with the following deviations from the standard protocol: exactly 650 µl aqueous phase after extraction were taken, and 1 µl Glycogen (Ambion, Tex., USA) was added to a final concentration of 50 µg/ml and precipitated with 975 µl 100% Ethanol. Columns were washed three times with RPE buffer and RNA was eluted once in 30 µl nuclease-free water and stored at −80° C.

qPCR Analysis

The qPCR-based high-throughput quantification of miRNAs was performed in 384-well plate using reagents by Exiqon. First, 10 µl of isolated RNA were reverse transcribed in 50 µl reactions using the Universal cDNA Synthesis Kit II. UniSp6 and cel-miR-39-3p were are added during this step to monitor the presence of enzyme inhibitors. cDNA samples ere diluted 100-fold prior to qPCR analysis in pre-coated Pick&Mix 384-well plates with custom design. Using an epMotion P5073 liquid handling robot (Eppendorf, Germany), 10 µl of qPCR mix were distributed to each well of the qPCR palte. Each miRNA is assayed once per sample in a 10 µl reaction using the Roche LC 480 Real-Time PCR System (Roche, Germany).

Data Analysis

Melting curve analysis was performed and miRNA PCR reactions with more than one peak were excluded from the analysis. Amplification efficiencies were calculated using algorithms similar to the linreg software package. Efficiencies ranged between 1.8 and 2.1 for most miRNAs. Individual reactions that gave efficiencies <1.6 were excluded from the dataset. Background levels for each miRNA were generated by assaying a "no template" cDNA synthesis control on a full serum/plasma focus panel plate. The majority of miRNA assays did not yield any signal and background Cp was set to 42. The expression data was prefiltered according to the following criteria: i) features with more than 50% empty-values were excluded; ii) features with a p-value of <0.05 in a single-factor ANOVA analysis between any of the 4 groups were selected; iii) features with chi-square test p-value <0.1, indicating unequal distribution of negative signals between fracture and non-fracture samples or diabetes and non-diabetes samples, were selected. The aim of this step was to allow only features with trend towards regulation in any of the 4 groups to be further processed. The Ct-values of the remaining 146 features were corrected for the global mean of spike-in control levels and finally, empty values were replaced by imputed values, based on the assumption of normal distributed values.

Gene-wise linear models were fitted incorporating class information, e.g. fracture vs. no fracture, or diabetic fracture vs diabetic control, by generalized least squares. The p-values of the test whether the class coefficient is different from 0 were adjusted for multiple testing using the method proposed by Benjamini and Hochberg. The limma package from the Bioconductor repository was used. Every single model was evaluated by means of the AUC values and misclassification rates of a 5-fold cross validation using the support vector machine as a base classifier. The smallest model size that obtained an AUC value close to the maximum AUC value was chosen. The entire procedure was repeated with simulated data that incorporated the same dimensionality and correlation structure as the original data but exhibited no difference in means between classes. The maximal resulting AUC value was used as a reference point characterized by zero reproducibility. All models selected using the two step method described above clearly yielded superior results as compared to the reference point.

Results

For the classification of non-diabetic fracture patients, a combination of 4 microRNAs (FIGS. 1a and b) was identified that yielded an AUC value of 0.978. This combination consisted of miR-188-3p, miR-942, miR-155-5p, and miR-382-3p. Further incorporation of miRNAs (up to 10 miR-NAs in total) in the classification model could improve AUC to a value of 1.0 (FIG. 2a), of which miR-136-3p and miR-502-5p had the strongest effect on the classification.

For the classification of diabetic fracture patients, a combination of 4 microRNAs (FIGS. 1c and d) was identified that yielded an AUC value of 0.933. This combination consisted of miR-550a-5p, miR-96-5p, miR-32-3p, and miR-486-3p. Further incorporation of miRNAs (up to 10 miRNAs in total) in the classification model could improve AUC to a value of 1.0 (FIG. 2b), of which miR-203a and miR-141-3p, and let-323a-3p had the strongest effect on the classification.

Example 3: Analysis of microRNA Function in the Context of Osteogenic Differentiation Human adipose-derived stem cells (ASCs) were obtained from subcutaneous adipose tissue, which was derived from outpatient tumescence liposuction under local anesthesia with patient consent. ASCs were isolated as described before (Wolbank et al., 2007a; Wolbank et al., 2007b; Wolbank et al., 2009a) and cultured in DMEM-low glucose/HAM's F-12 supplemented with 4 mM L-glutamine, 10% fetal calf serum (FCS, PAA) and 1 ng/mL recombinant human basic fibroblast growth factor (rhFGF, R&D Systems) at 37° C., 5% $CO_2$ and 95% air humidity. Cells were passaged once or twice a week at a split ratio of 1:2 according to the growth rate.

Induction of Osteogenic Differentiation in ASCs

All differentiation protocols were carried out in 24 well cell culture plates. For osteogenic differentiation ASCs were seeded at a density of $2 \times 10^3$ cell per well. 72 hours after seeding cells were incubated with osteogenic differentiation medium (DMEM-low glucose, 10% FCS, 4 mM L-glutamine, 10 nM dexamethasone, 150 µM ascorbate-2-phosphat, 10 mM β-glycerolphosphate and 10 nM vitamine-D3) up to 4 weeks.

Alizarin Red S Staining

For Alizarin staining of calcified structures, cells were fixed for 1 hour in 70% ethanol at −20° C. After brief rinsing, cells were stained for 20 minutes with 40 mM Alizarin Red solution (Sigma) and washed with PBS. For quantification Alizarin was extracted for 30 minutes using 200 µl 0.1 M HCL/0.5% SDS solution. The extracted dye was measured at 425 nm.

Transfections

ASCs were transfected using siPORT™ NeoFX™ transfection reagent (Applied Biosystems). Cells were transfected with 10 nM precursor microRNA, or scrambled miRNA control #2 (Ambion) according to the manufacturer's protocol. Three days after transfection, differentiation was started as described above.

Results

Transfection of hsa-miR-10b-5p, hsa-miR-203a, hsa-miR-376a-3p, and miR-550a-5p resulted in a significant inhibition of osteogenic differentiation by 50% or more. Transfection of hsa-miR-188-3p, hsa-miR-199b-5p, and miR-148a-5p resulted in a significant acceleration of osteogenic differentiation by more than 200% and up to 400%.

Tables

TABLE 1

| # | Patient Cohort | miRNA ID | Log2 Fold Change (diseased vs control) | p-Value |
|---|---|---|---|---|
| 1 | recent OFX | hsa-miR-10a-5p | 0.95 | 0.0012 |
| 2 | Group I | hsa-miR-10b-5p | 1.01 | 0.0012 |
| 3 | | hsa-miR-106a-5p | −0.33 | 0.078 |
| 4 | | hsa-miR-125b-5p | 0.54 | 0.2734 |
| 5 | | hsa-miR-127-3p | 0.83 | 0.1634 |
| 6 | | hsa-miR-133a | −0.55 | 0.3295 |
| 7 | | hsa-miR-133b | −1.47 | 0.0280 |
| 8 | | hsa-miR-143-3p | −0.51 | 0.1010 |
| 9 | | hsa-miR-18a-3p | −0.50 | 0.2741 |
| 10 | | hsa-miR-194-5p | 0.49 | 0.2266 |
| 11 | | hsa-miR-30a-5p | 0.72 | 0.1092 |
| 12 | | hsa-miR-328-3p | −0.62 | 0.0344 |
| 13 | | hsa-miR-376a-3p | 0.77 | 0.1160 |
| 14 | | hsa-miR-409-3p | 0.86 | 0.2042 |
| 15 | | hsa-miR-574-3p | −0.51 | 0.2016 |
| 1 | non-recent OFX | hsa-let-7i-3p | −0.56 | 0.206 |
| 2 | Group II | hsa-miR-1227-3p | 0.53 | 0.643 |
| 3 | | hsa-miR-127-3p | −1.04 | 0.145 |
| 4 | | hsa-miR-133b | −0.81 | 0.086 |
| 5 | | hsa-miR-135a-5p | −0.90 | 0.030 |
| 6 | | hsa-miR-136-3p | −0.87 | 0.055 |
| 7 | | hsa-miR-143-3p | −0.64 | 0.210 |
| 8 | | hsa-miR-155-5p | −1.11 | 0.013 |

TABLE 1-continued

| # | Patient Cohort | miRNA ID | Log2 Fold Change (diseased vs control) | p-Value |
|---|---|---|---|---|
| 9 | | hsa-miR-181a-3p | -2.93 | 0.000 |
| 10 | | hsa-miR-188-3p | -1.72 | 0.003 |
| 11 | | hsa-miR-1908 | -0.90 | 0.484 |
| 12 | | hsa-miR-190a | -1.37 | 0.052 |
| 13 | | hsa-miR-192-5p | -0.64 | 0.090 |
| 14 | | hsa-miR-193b-3p | -0.74 | 0.137 |
| 15 | | hsa-miR-196b-5p | -0.64 | 0.201 |
| 16 | | hsa-miR-199b-5p | -0.62 | 0.553 |
| 17 | | hsa-miR-200b-3p | -0.61 | 0.236 |
| 18 | | hsa-miR-203a | 0.87 | 0.725 |
| 19 | | hsa-miR-205-5p | -0.53 | 0.162 |
| 20 | | hsa-miR-20b-5p | -0.67 | 0.225 |
| 21 | | hsa-miR-214-3p | -0.57 | 0.209 |
| 22 | | hsa-miR-215 | -0.61 | 0.124 |
| 23 | | hsa-miR-223-5p | -0.58 | 0.144 |
| 24 | | hsa-miR-27a-3p | -0.52 | 0.145 |
| 25 | | hsa-miR-30e-3p | -0.63 | 0.100 |
| 26 | | hsa-miR-323a-3p | -0.67 | 0.165 |
| 27 | | hsa-miR-330-3p | 1.02 | 0.088 |
| 28 | | hsa-miR-342-5p | -1.16 | 0.035 |
| 29 | | hsa-miR-369-3p | -1.04 | 0.055 |
| 30 | | hsa-miR-376c-3p | -0.74 | 0.152 |
| 31 | | hsa-miR-377-3p | -1.02 | 0.062 |
| 32 | | hsa-miR-378a-5p | -1.19 | 0.016 |
| 33 | | hsa-miR-410 | -0.59 | 0.151 |
| 34 | | hsa-miR-454-3p | -0.59 | 0.179 |
| 35 | | hsa-miR-487b | -0.91 | 0.132 |
| 36 | | hsa-miR-495-3p | -1.02 | 0.089 |
| 37 | | hsa-miR-500a-5p | -0.96 | 0.122 |
| 38 | | hsa-miR-502-5p | -1.36 | 0.040 |
| 39 | | hsa-miR-542-5p | -1.43 | 0.126 |
| 40 | | hsa-miR-548a-3p | -0.66 | 0.252 |
| 41 | | hsa-miR-550a-5p | 2.17 | 0.052 |
| 42 | | hsa-miR-576-3p | -1.58 | 0.002 |
| 43 | | hsa-miR-582-3p | -1.55 | 0.020 |
| 44 | | hsa-miR-624-5p | -0.69 | 0.197 |
| 45 | | hsa-miR-642a-5p | -1.56 | 0.018 |
| 46 | | hsa-miR-941 | -0.66 | 0.442 |
| 47 | | hsa-miR-942 | -1.88 | 0.002 |
| 48 | | Hsa-miR-382-3p | -2.11 | 0.471 |
| 1 | non-recent DMFX Group III | hsa-let-7b-5p | 0.97 | 0.005 |
| 2 | | hsa-let-7g-5p | 0.99 | 0.002 |
| 3 | | hsa-let-7i-5p | 0.91 | 0.002 |
| 4 | | hsa-miR-106a-5p | 0.96 | 0.009 |
| 5 | | hsa-miR-106b-5p | 1.01 | 0.006 |
| 6 | | hsa-miR-127-3p | -1.29 | 0.487 |
| 7 | | hsa-miR-132-3p | 0.84 | 0.015 |
| 8 | | hsa-miR-140-3p | 0.78 | 0.014 |
| 9 | | hsa-miR-141-3p | 1.27 | 0.002 |
| 10 | | hsa-miR-143-3p | 0.87 | 0.080 |
| 11 | | hsa-miR-143-5p | 1.42 | 0.007 |
| 12 | | hsa-miR-144-3p | 0.94 | 0.009 |
| 13 | | hsa-miR-146b-5p | 0.90 | 0.012 |
| 14 | | hsa-miR-154-5p | -1.64 | 0.127 |
| 15 | | hsa-miR-16-2-3p | 1.03 | 0.001 |
| 16 | | hsa-miR-16-5p | 0.89 | 0.008 |
| 17 | | hsa-miR-17-5p | 0.98 | 0.032 |
| 18 | | hsa-miR-181b-5p | 0.83 | 0.035 |
| 19 | | hsa-miR-181c-3p | 1.51 | 0.002 |
| 20 | | hsa-miR-181c-5p | 1.25 | 0.004 |
| 21 | | hsa-miR-185-5p | 0.81 | 0.024 |
| 22 | | hsa-miR-18a-3p | 0.77 | 0.051 |
| 23 | | hsa-miR-18a-5p | 0.88 | 0.020 |
| 24 | | hsa-miR-18b-5p | 0.92 | 0.019 |
| 25 | | hsa-miR-1908 | -1.43 | 0.186 |
| 26 | | hsa-miR-191-5p | 0.99 | 0.006 |
| 27 | | hsa-miR-196b-5p | 1.03 | 0.037 |
| 28 | | hsa-miR-199b-5p | 1.35 | 0.082 |
| 29 | | hsa-miR-19b-1-5p | 2.38 | 0.007 |
| 30 | | hsa-miR-19b-3p | 0.76 | 0.018 |
| 31 | | hsa-miR-200b-3p | 0.94 | 0.050 |
| 32 | | hsa-miR-203a | 1.98 | 0.007 |
| 33 | | hsa-miR-20a-5p | 0.92 | 0.013 |
| 34 | | hsa-miR-20b-5p | 1.12 | 0.068 |
| 35 | | hsa-miR-210 | 0.78 | 0.023 |
| 36 | | hsa-miR-21-3p | 1.09 | 0.003 |
| 37 | | hsa-miR-25-3p | 0.82 | 0.016 |
| 38 | | hsa-miR-26b-5p | 0.79 | 0.023 |
| 39 | | hsa-miR-301a-3p | 1.15 | 0.005 |
| 40 | | hsa-miR-301b | 1.17 | 0.010 |
| 41 | | hsa-miR-323a-3p | 1.21 | 0.002 |
| 42 | | hsa-miR-324-5p | 1.15 | 0.017 |
| 43 | | hsa-miR-330-3p | 1.23 | 0.022 |
| 44 | | hsa-miR-363-3p | 0.83 | 0.008 |
| 45 | | hsa-miR-369-3p | -1.29 | 0.011 |
| 46 | | hsa-miR-374a-5p | 0.84 | 0.017 |
| 47 | | hsa-miR-375 | 1.30 | 0.004 |
| 48 | | hsa-miR-376c-3p | -0.98 | 0.052 |
| 49 | | hsa-miR-378a-5p | 1.09 | 0.023 |
| 50 | | hsa-miR-451a | 0.91 | 0.012 |
| 51 | | hsa-miR-454-3p | 0.99 | 0.023 |
| 52 | | hsa-miR-486-3p | 1.16 | 0.018 |
| 53 | | hsa-miR-486-5p | 1.04 | 0.003 |
| 54 | | hsa-miR-493-5p | -0.85 | 0.607 |
| 55 | | hsa-miR-500a-5p | 1.93 | 0.001 |
| 56 | | hsa-miR-532-3p | 0.87 | 0.006 |
| 57 | | hsa-miR-545-3p | 1.33 | 0.017 |
| 58 | | hsa-miR-550a-3p | 0.98 | 0.032 |
| 59 | | hsa-miR-550a-5p | 4.84 | 0.000 |
| 60 | | hsa-miR-589-5p | 0.83 | 0.719 |
| 61 | | hsa-miR-590-3p | 0.92 | 0.055 |
| 62 | | hsa-miR-598 | 0.87 | 0.068 |
| 63 | | hsa-miR-627 | 0.97 | 0.034 |
| 64 | | hsa-miR-629-5p | 0.96 | 0.009 |
| 65 | | hsa-miR-7-5p | 1.40 | 0.001 |
| 66 | | hsa-miR-92a-3p | 0.81 | 0.002 |
| 67 | | hsa-miR-93-3p | 0.86 | 0.042 |
| 68 | | hsa-miR-93-5p | 0.93 | 0.018 |
| 69 | | hsa-miR-941 | 1.70 | 0.024 |
| 70 | | hsa-miR-942 | 2.36 | 0.000 |
| 71 | | hsa-miR-96-5p | 1.35 | 0.000 |
| 72 | | hsa-miR-98-5p | 0.85 | 0.031 |
| 73 | | hsa-miR-181a-5p | 0.74 | 0.041 |
| 74 | | hsa-miR-32-3p | 1.11 | 0.021 |

TABLE 2

Recent Osteoporotic Fracture vs Control

| mature ID | mature Sequence | SEQ ID | mature Accession | precursor-miRNA | precursor miRNA Sequence | SEQ ID | precursor miRNA Accession |
|---|---|---|---|---|---|---|---|
| hsa-miR-10a-5p | UACCCUGUAGAUCCGAAUUUGUG | 1 | MIMAT0000253 | hsa-mir-10a | GAUCUGUCUGUCUUCUGUAUAUACCCUGUAGAUCCGAAUUUGUGUAAGGAAUUUUGUGGUCACAAAUUCGUAUCUAGGGGAAUAUGUAGUUGACAUAAACACUCCGCUCU | 16 | MI0000266 |

TABLE 2-continued

Recent Osteoporotic Fracture vs Control

| mature ID | mature Sequence | SEQ ID | mature Accession | precursor-miRNA | precursor miRNA Sequence | SEQ ID | precursor miRNA Accession |
|---|---|---|---|---|---|---|---|
| hsa-miR-10b-5p | UACCCUGUAGAACCGAAUUUGUG | 2 | MIMAT0000254 | hsa-mir-10b | CCAGAGGUUGUAACGUUGUCUAUAUAUACCCUGUAGAACCGAAUUUGUGUGGUAUCCGUAUAGUCACAGAUUCGAUUCUAGGGGAAUAUAUGGUCGAUGCAAAAACUUCA | 17 | MI0000267 |
| hsa-miR-106a-5p | AAAAGUGCUUACAGUGCAGGUAG | 3 | MIMAT0000103 | hsa-mir-106a | CCUUGGCCAUGUAAAAGUGCUUACAGUGCAGGUAGCUUUUUGAGAUCUACUGCAAUGUAAGCACUUCUUACAUUACCAUGG | 18 | MI0000113 |
| hsa-miR-125b-5p | UCCCUGAGACCCUAACUUGUGA | 4 | MIMAT0000423 | hsa-mir-125b-1 | UGCGCUCCUCUCAGUCCCUGAGACCCUAACUUGUGAUGUUUACCGUUUAAAUCCACGGGUUAGGCUCUUGGGAGCUGCGAGUCGUGCU | 19 | MI0000446 |
| hsa-miR-127-3p | UCGGAUCCGUCUGAGCUUGGCU | 5 | MIMAT0000446 | hsa-mir-127 | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC | 20 | MI0000472 |
| hsa-miR-133a-3p | UUUGGUCCCCUUCAACCAGCUG | 6 | MIMAT0000427 | hsa-mir-133a-1 | ACAAUGCUUUGCUAGAGCUGGUAAAAUGGAACCAAAUCGCCUCUUCAAUGGAUUUGGUCCCCUUCAACCAGCUGUAGCUAUGCAUUGA | 21 | MI0000450 |
| hsa-miR-133b | UUUGGUCCCCUUCAACCAGCUA | 7 | MIMAT0000770 | hsa-mir-133b | CCUCAGAAGAAAGAUGCCCCCUGCUCUGGCUGGUCAAACGGAACCAAGUCCGUCUUCCUGAGAGGUUUGGUCCCUUCAACCAGCUACAGCAGGGCUGGCAAUGCCCAGUCCUUGGAGA | 22 | MI0000822 |
| hsa-miR-143-3p | UGAGAUGAAGCACUGUAGCUC | 8 | MIMAT0000435 | hsa-mir-143 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | 23 | MI0000459 |
| hsa-miR-18a-3p | ACUGCCCUAAGUGCUCCUUCUGG | 9 | MIMAT0002891 | hsa-mir-18a | UGUUCUAAGGUGCAUCUAGUGCAGAUAGUGAAGUAGAUUAGCAUCUACUGCCCUAAGUGCUCCUUCUGGCA | 24 | MI0000072 |
| hsa-miR-194-5p | UGUAACAGCAACUCCAUGUGGA | 10 | MIMAT0000460 | hsa-mir-194-1 | AUGGUGUUAUCAAGUGUAACAGCAACUCCAUGUGGACUGUGUACCAAUUCCAGUGGAGAUGCUGUUACUUUUGAUGGUUACCAA | 25 | MI0000488 |

TABLE 2-continued

Recent Osteoporotic Fracture vs Control

| mature ID | mature Sequence | SEQ ID | mature Accession | precursor-miRNA | precursor miRNA Sequence | SEQ ID | precursor miRNA Accession |
|---|---|---|---|---|---|---|---|
| hsa-miR-30a-5p | UGUAAAC AUCCUCG ACUGGAA G | 11 | MIMAT0000087 | hsa-mir-30a | GCGACUGUAAACAU CCUCGACUGGAAGC UGUGAAGCCACAGA UGGGCUUUCAGUCG GAUGUUUGCAGCUG C | 26 | MI0000088 |
| hsa-miR-328-3p | CUGGCCC UCUCUGC CCUUCCG U | 12 | MIMAT0000752 | hsa-mir-328 | UGGAGUGGGGGGC AGGAGGGGCUCAGG GAGAAAGUGCAUAC AGCCCCUGGCCCUCU CUGCCCUUCCGUCCC CUG | 27 | MI0000804 |
| hsa-miR-376a-3p | AUCAUAG AGGAAAA UCCACGU | 13 | MIMAT0000729 | hsa-mir-376a-1 | UAAAAGGUAGAUUC UCCUUCUAUGAGUA CAUUAUUUAUGAUU AAUCAUAGAGGAAA AUCCACGUUUUC | 28 | MI0000784 |
| hsa-miR-409-3p | GAAUGUU GCUCGGU GAACCCCU | 14 | MIMAT0001639 | hsa-mir-409 | UGGUACUCGGGGAG AGGUUACCCGAGCAA CUUUGCAUCUGGAC GACGAAUGUUGCUC GGUGAACCCCUUUU CGGUAUCA | 29 | MI0001735 |
| hsa-miR-574-3p | CACGCUCA UGCACAC ACCCACA | 15 | MIMAT0003239 | hsa-mir-574 | GGGACCUGCGUGGG UGCGGGCGUGUGAG UGUGUGUGUGUGA GUGUGUGUCGCUCC GGGUCCACGCUCAU GCACACACCCACACG CCCACACUCAGG | 30 | MI0003581 |

TABLE 3

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| hsa-let-7i-3p | 31 | CUGCGCAA GCUACUGC CUUGCU | MIMAT0004585 | hsa-let-7i | 78 | CUGGCUGAGGUAGU AGUUUGUGCUGUUG GUCGGGUUGUGACA UUGCCCGCUGUGGA GAUAACUGCGCAAGC UACUGCCUUGCUA | MI0000434 |
| hsa-miR-1227-3p | 32 | CGUGCCAC CCUUUUCC CCAG | MIMAT0005580 | hsa-mir-1227 | 79 | GUGGGGCCAGGCGG UGGUGGGCACUGCU GGGGUGGGCACAGC AGCCAUGCAGAGCG GGCAUUUGACCCCG UGCCACCCUUUUCCC CAG | MI0006316 |
| hsa-miR-127-3p | 33 | UCGGAUCC GUCUGAGC UUGGCU | MIMAT0000446 | hsa-mir-127 | 80 | UGUGAUCACUGUCU CCAGCCUGCUGAAGC UCAGAGGGCUCUGA UUCAGAAAGAUCAU CGGAUCCGUCUGAG CUUGGCUGGUCGGA AGUCUCAUCAUC | MI0000472 |
| hsa-miR-133b | 34 | UUUGGUC CCCUUCAA CCAGCUA | MIMAT0000770 | hsa-mir-133b | 81 | CCUCAGAAGAAAGAU GCCCCCUGCUCUGGC UGGUCAAACGGAACC AAGUCCGUCUUCCU GAGAGGUUUGGUCC CCUUCAACCAGCUAC | MI0000822 |

TABLE 3-continued

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| | | | | | | AGCAGGGCUGGCAAUGCCCAGUCCUUGGAGA | |
| hsa-miR-135a-5p | 35 | UAUGGCUUUUUAUUCCUAUGUGA | MIMAT0000428 | hsa-mir-135a-1 | 82 | AGGCCUCGCUGUUCUCUAUGGCUUUUUAUUCCUAUGUGAUUCUACUGCUCACUCAUAUAGGGAUUGGAGCCGUGGCGCACGGCGGGGACA | MI0000452 |
| hsa-miR-136-3p | 36 | CAUCAUCGUCUCAAAUGAGUCU | MIMAT0004606 | hsa-mir-136 | 83 | UGAGCCCUCGGAGGACUCCAUUUGUUUUGAUGAUGGAUUCUUAUGCUCCAUCAUCGUCUCAAAUGAGUCUUCAGAGGGUUCU | MI0000475 |
| hsa-miR-143-3p | 37 | UGAGAUGAAGCACUGUAGCUC | MIMAT0000435 | hsa-mir-143 | 84 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | MI0000459 |
| hsa-miR-155-5p | 38 | UUAAUGCUAAUCGUGAUAGGGGU | MIMAT0000646 | hsa-mir-155 | 85 | CUGUUAAUGCUAAUCGUGAUAGGGGUUUGCCUCCAACUGACUCCUACAUAUUAGCAUUAACAG | MI0000681 |
| hsa-miR-181a-3p | 39 | ACCAUCGACCGUUGAUUGUACC | MIMAT0000270 | hsa-mir-181a-1 | 86 | UGAGUUUUGAGGUUGCUUCAGUGAACAUUCAACGCUGUCGGUGAGUUUGGAAUUAAAAUCAAAACCAUCGACCGUUGAUUGUACCCUAUGGCUAACCAUCAUCUACUCCA | MI0000289 |
| hsa-miR-188-3p | 40 | CUCCCACAUGCAGGGUUUGCA | MIMAT0004613 | hsa-mir-188 | 87 | UGCUCCCUCUCUCACAUCCCUUGCAUGGUGGAGGGUGAGCUUUCUGAAAACCCCUCCCACAUGCAGGGUUUGCAGGAUGGCGAGCC | MI0000484 |
| hsa-miR-1908-5p | 41 | CGGCGGGGACGGCGAUUGGUC | MIMAT0007881 | hsa-mir-1908 | 88 | CGGGAAUGCCGCGGCGGGGACGGCGAUUGGUCCGUAUGUGUGGUGCCACCGGCCGCCGGCUCCGCCCCGGCCCCGCCCC | MI0008329 |
| hsa-miR-190a-5p | 42 | UGAUAUGUUUGAUAUAUUAGGU | MIMAT0000458 | hsa-mir-190a | 89 | UGCAGGCCUCUGUGUGAUAUGUUUGAUAUAUUAGGUUGUAUUUUAAUCCAACUAUAUAUCAAACAUAUUCCUACAGUGUCUUGCC | MI0000486 |
| hsa-miR-192-5p | 43 | CUGACCUAUGAAUUGACAGCC | MIMAT0000222 | hsa-mir-192 | 90 | GCCGAGACCGAGUGCACAGGGCUCUGACCUAUGAAUUGACAGCCAGUGCUCUCGUCUCCCCUCUGGCUGCCAAUUCCAUAGGUCACAGGUAUGUUCGCCUCAAUGCCAGC | MI0000234 |

TABLE 3-continued

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| hsa-miR-193b-3p | 44 | AACUGGCCCUCAAAGUCCCGCU | MIMAT0002819 | hsa-mir-193b | 91 | GUGGUCUCAGAAUCGGGGUUUUGAGGGCGAGAUGAGUUUAUGUUUUAUCCAACUGGCCCUCAAAGUCCCGCUUUUGGGGUCAU | MI0003137 |
| hsa-miR-196b-5p | 45 | UAGGUAGUUUCCUGUUGUUGGG | MIMAT0001080 | hsa-mir-196b | 92 | ACUGGUCGGUGAUUUAGGUAGUUUCCUGUUGUUGGGAUCCACCUUUCUCUCGACAGCACGACACUGCCUUCAUUACUUCAGUUG | MI0001150 |
| hsa-miR-199b-5p | 46 | CCCAGUGUUUAGACUAUCUGUUC | MIMAT0000263 | hsa-mir-199b | 93 | CCAGAGGACACCUCCACUCCGUCUACCCAGUGUUUAGACUAUCUGUUCAGGACUCCCAAAUUGUACAGUAGUCUGCACAUUGGUUAGGCUGGGCUGGGUUAGACCCUCGG | MI0000282 |
| hsa-miR-200b-3p | 47 | UAAUACUGCCUGGUAAUGAUGA | MIMAT0000318 | hsa-mir-200b | 94 | CCAGCUCGGGCAGCCGUGGCCAUCUUACUGGGCAGCAUUGGAUGGAGUCAGGUCUCUAAUACUGCCUGGUAAUGAUGACGGCGGAGCCCUGCACG | MI0000342 |
| hsa-miR-203a | 48 | GUGAAAUGUUUAGGACCACUAG | MIMAT0000264 | hsa-mir-203a | 95 | GUGUUGGGGACUCGCGCGCUGGGUCCAGUGGUUCUUAACAGUUCAACAGUUCUGUAGCGCAAUUGUGAAAUGUUUAGGACCACUAGACCCGGCGGGCGCGGCGACAGCGA | MI0000283 |
| hsa-miR-205-5p | 49 | UCCUUCAUUCCACCGGAGUCUG | MIMAT0000266 | hsa-mir-205 | 96 | AAAGAUCCUCAGACAAUCCAUGUGCUUCUCUUGUCCUUCAUUCCACCGGAGUCUGUCUCAUACCCAACCAGAUUUCAGUGGAGUGAAGUUCAGGAGGCAUGGAGCUGACA | MI0000285 |
| hsa-miR-20b-5p | 50 | CAAAGUGCUCAUAGUGCAGGUAG | MIMAT0001413 | hsa-mir-20b | 97 | AGUACCAAAGUGCUCAUAGUGCAGGUAGUUUUGCAUGACUCUACUGUAGUAUGGGCACUUCCAGUACU | MI0001519 |
| hsa-miR-214-3p | 51 | ACAGCAGGCACAGACAGGCAGU | MIMAT0000271 | hsa-mir-214 | 98 | GGCCUGGCUGGACAGAGUUGUCAUGUGUCUGCCUGUCUACACUUGCUGUGCAGAACAUCCGCUCACCUGUACAGCAGGCACAGACAGGCAGUCACAUGACAACCCAGCCU | MI0000290 |
| hsa-miR-215-5p | 52 | AUGACCUAUGAAUUGACAGAC | MIMAT0000272 | hsa-mir-215 | 99 | AUCAUUCAGAAAUGGUAUACAGGAAAAUGACCUAUGAAUUGACAGACAAUAUAGCUGAGUUUGUCUGUCAUUUCUUUAGGCCAAUAUUCUGUAUGACUGUGCUACUUCAA | MI0000291 |

TABLE 3-continued

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| hsa-miR-223-5p | 53 | CGUGUAUUUGACAAGCUGAGUU | MIMAT0004570 | hsa-mir-223 | 100 | CCUGGCCUCCUGCAGUGCCACGCUCCGUGUAUUUGACAAGCUGAGUUGGACACUCCAUGUGGUAGAGUGUCAGUUUGUCAAAUACCCCAAGUGCGGCACAUGCUUACCAG | MI0000300 |
| hsa-miR-27a-3p | 54 | UUCACAGUGGCUAAGUUCCGC | MIMAT0000084 | hsa-mir-27a | 101 | CUGAGGAGCAGGGCUUAGCUGCUUGUGAGCAGGGUCCACACCAAGUCUGUUCACAGUGGCUAAGUUCCGCCCCCAG | MI0000085 |
| hsa-miR-30e-3p | 55 | CUUUCAGUCGGAUGUUUACAGC | MIMAT0000693 | hsa-mir-30e | 102 | GGGCAGUCUUUGCUACUGUAAACAUCCUUGACUGGAAGCUGUAAGGUGUUCAGAGGAGCUUUCAGUCGGAUGUUUACAGCGGCAGGCUGCCA | MI0000749 |
| hsa-miR-323a-3p | 56 | CACAUUACACGGUCGACCUCU | MIMAT0000755 | hsa-mir-323a | 103 | UUGGUACUUGGAGAGAGGUGGUCCUGUGCGCGUUCGCUUUAUUUAUGGCGCACAUUACACGGUCGACCUCUUUGCAGUAUCUAAUC | MI0000807 |
| hsa-miR-330-3p | 57 | GCAAAGCACACGGCCUGCAGAGA | MIMAT0000751 | hsa-mir-330 | 104 | CUUUGGCGAUCACUGCCUCUCUGGGCCUGUGUCUUAGGCUCUGCAAGAUCAACCGAGCAAAGCACACGGCCUGCAGAGAGGCAGCGCUCUGCCC | MI0000803 |
| hsa-miR-342-5p | 58 | AGGGGUGCUAUCUGUGAUUGA | MIMAT0004694 | hsa-mir-342 | 105 | GAAACUGGGCUCAAGGUGAGGGGUGCUAUCUGUGAUUGAGGGACAUGGUUAAUGGAAUUGUCUCACACAGAAAUCGCACCCGUCACCUUGGCCUACUUA | MI0000805 |
| hsa-miR-369-3p | 59 | AAUAAUACAUGGUUGAUCUUU | MIMAT0000721 | hsa-mir-369 | 106 | UUGAAGGGAGAUCGACCGUGUUAUAUUCGCUUUAUUGACUUCGAAUAAUACAUGGUUGAUCUUUUCUCAG | MI0000777 |
| hsa-miR-376c-3p | 60 | AACAUAGAGGAAAUUCCACGU | MIMAT0000720 | hsa-mir-376c | 107 | AAAAGGUGGAUAUUCCUUCUAUGUUUAUGUUAUUUAUGGUUAAACAUAGAGGAAAUUCCACGUUUU | MI0000776 |
| hsa-miR-377-3p | 61 | AUCACACAAAGGCAACUUUUGU | MIMAT0000730 | hsa-mir-377 | 108 | UUGAGCAGAGGUUGCCCUUGGUGAAUUCGCUUUAUUUAUGUUGAAUCACACAAAGGCAACUUUUGUUUG | MI0000785 |
| hsa-miR-378a-5p | 62 | CUCCUGACUCCAGGUCCUGUGU | MIMAT0000731 | hsa-mir-378a | 109 | AGGGCUCCUGACUCCAGGUCCUGUGUGUUACCUAGAAAUAGCACUGGACUUGGAGUCAGAAGGCCU | MI0000786 |
| hsa-miR-382-3p | 269 | AAUCAUUCACGGACAACACUU | MIMAT0022697 | hsa-mir-382 | 270 | UACUUGAAGAGAAGUUGUUCGUGGUGGAUUCGCUUUACUUAU | MI0000790 |

TABLE 3-continued

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| | | | | | | GACGAAUCAUUCAC GGACAACACUUUUU UCAGUA | |
| hsa-miR-410-3p | 63 | AAUAUAACACAGAUGGCCUGU | MIMAT0002171 | hsa-mir-410 | 110 | GGUACCUGAGAAGAGGUUGUCUGUGAUGAGUUCGCUUUUAUUAAUGACGAAUAUAACACAGAUGGCCUGUUUUCAGUACC | MI0002465 |
| hsa-miR-454-3p | 64 | UAGUGCAAUAUUGCUUAUAGGGU | MIMAT0003885 | hsa-mir-454 | 111 | UCUGUUUAUCACCAGAUCCUAGAACCCUAUCAAUAUUGUCUCUGCUGUGUAAAUAGUUCUGAGUAGUGCAAUAUUGCUUAUAGGGUUUUGGUGUUUGGAAAGAACAAUGGGCAGG | MI0003820 |
| hsa-miR-487b-3p | 65 | AAUCGUACAGGGUCAUCCACUU | MIMAT0003180 | hsa-mir-487b | 112 | UUGGUACUUGGAGAGUGGGUUUAUCCCUGUCCUGUUCGUUUUGCUCAUGUCGAAUCGUACAGGGUCAUCCACUUUUUUCAGUAUCAA | MI0003530 |
| hsa-miR-495-3p | 66 | AAACAAACAUGGUGCACUUCUU | MIMAT0002817 | hsa-mir-495 | 113 | UGGUACCUGAAAAGAAGUUGCCCAUGUUAUUUUCGCUUUAUAUGUGACGAAACAAACAUGGUGCACUUCUUUUUCGGUAUCA | MI0003135 |
| hsa-miR-500a-5p | 67 | UAAUCCUUGCUACCUGGGUGAGA | MIMAT0004773 | hsa-mir-500a | 114 | GCUCCCCCUCUCUAAUCCUUGCUACCUGGGUGAGAGUGCUGUCUGAAUGCAAUGCACCUGGGCAAGGAUUCUGAGAGCGAGAGC | MI0003184 |
| hsa-miR-502-5p | 68 | AUCCUUGCUAUCUGGGUGCUA | MIMAT0002873 | hsa-mir-502 | 115 | UGCUCCCCCUCUCUAAUCCUUGCUAUCUGGGUGCUAGUGCUGGCUCAAUGCAAUGCACCUGGGCAAGGAUUCAGAGAGGGGAGCU | MI0003186 |
| hsa-miR-542-5p | 69 | UCGGGGAUCAUCAUGUCACGAGA | MIMAT0003340 | hsa-mir-542 | 116 | CAGAUCUCAGACAUCUCGGGGAUCAUCAUGUCACGAGAUACCAGUGUGCACUUGUGACAGAUUGAUAACUGAAAGGUCGGGAGCCACUCAUCUUCA | MI0003686 |
| hsa-miR-548a-3p | 70 | CAAAACUGGCAAUUACUUUUGC | MIMAT0003251 | hsa-mir-548a-1 | 117 | UGCAGGGAGGUAUUAAGUUGGUGCAAAAGUAAUUGUGAUUUUGCCAUUAAAAGUAACGACAAAACUGGCAAUUACUUUUGCACCAAACCUGGUAUU | MI0003593 |
| hsa-miR-550a-5p | 71 | AGUGCCUGAGGGAGUAAGAGCCC | MIMAT0004800 | hsa-mir-550a-1 | 118 | UGAUGCUUUGCUGGCUGGUGCAGUGCCUGAGGGAGUAAGAGCCCCUGUUGUUGUAAGAUAGUGUCUUACUCCCUCAGGCACAUCUCAACAAGUCUCU | MI0003600 |

TABLE 3-continued

Non-recent Osteoporotic Fracture vs Control

| mature ID | SEQ ID | mature Seq | mature Acc | hairpin | SEQ ID | hairpin Seq | hairpin Acc |
|---|---|---|---|---|---|---|---|
| hsa-miR-576-3p | 72 | AAGAUGUGGAAAAAUUGGAAUC | MIMAT0004796 | hsa-mir-576 | 119 | UACAAUCCAACGAGGAUUCUAAUUUCUCCACGUCUUUGGUAAUAAGGUUUGGCAAAGAUGUGGAAAAAUUGGAAUCCUCAUUCGAUUGGUUAUAACCA | MI0003583 |
| hsa-miR-582-3p | 73 | UAACUGGUUGAACAACUGAACC | MIMAT0004797 | hsa-mir-582 | 120 | AUCUGUGCUCUUUGAUUACAGUUGUUCAACCAGUUACUAAUCUAACUAAUUGUAACUGGUUGAACAACUGAACCCAAGGGGUGCAAAGUAGAAACAUU | MI0003589 |
| hsa-miR-624-5p | 74 | UAGUACCAGUACCUUGUGUUCA | MIMAT0003293 | hsa-mir-624 | 121 | AAUGCUGUUUCAAGGUAGUACCAGUACCUUGUGUUCAGUGGAACCAAGGUAAACACAAGGUAUUGGUAUUACCUUGAGAUAGCAUUACACCUAAGUG | MI0003638 |
| hsa-miR-642a-5p | 75 | GUCCCUCUCCAAAUGUGUCUUG | MIMAT0003312 | hsa-mir-642a | 122 | AUCUGAGUUGGGAGGGUCCCUCUCCAAAUGUGUCUUGGGGUGGGGGAUCAAGACACAUUUGGAGAGGGAACCUCCCAACUCGGCCUCUGCCAUCAUU | MI0003657 |
| hsa-miR-941 | 76 | CACCCGGCUGUGUGCACAUGUGC | MIMAT0004984 | hsa-mir-941-1 | 123 | UGUGGACAUGUGCCCAGGGCCCGGGACAGCGCCACGGAAGAGGACGCACCCGGCUGUGUGCACAUGUGCCCA | MI0005763 |
| hsa-miR-942-5p | 77 | UCUUCUCUGUUUUGGCCAUGUG | MIMAT0004985 | hsa-mir-942 | 124 | AUUAGGAGAGUAUCUUCUCUGUUUUGGCAUGUGUGUACUCACAGCCCCUCACACAUGGCCGAAACAGAGAAGUUACUUUCCUAAU | MI0005767 |

TABLE 4

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| hsa-let-7b-5p | 125 | UGAGGUAGUAGGUUGUGUGGUU | MIMAT0000063 | hsa-let-7b | 197 | CGGGGUGAGGUAGUAGGUUGUGUGGUUUCAGGGCAGUGAUGUUGCCCCUCGGAAGAUAACUAUACAACCUACUGCCUUCCCUG | MI0000063 |
| hsa-let-7g-5p | 126 | UGAGGUAGUAGUUUGUACAGUU | MIMAT0000414 | hsa-let-7g | 198 | AGGCUGAGGUAGUAGUUUGUACAGUUUGAGGGUCUAUGAUACCACCCGGUACAGGAGAUAACUGUACAGGCCACUGCCUUGCCA | MI0000433 |
| hsa-let-7i-5p | 127 | UGAGGUAGUAGUUUGUGCUGUU | MIMAT0000415 | hsa-let-7i | 199 | CUGGCUGAGGUAGUAGUUUGUGCUGUUGGUCGGGUUGUGACAUUGCCCGCUGU | MI0000434 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | | | | | GGAGAUAACUGCGCAAGCUACUGCCUUGCUA | |
| hsa-miR-106a-5p | 128 | AAAAGUGCUUACAGUGCAGGUAG | MIMAT0000103 | hsa-mir-106a | 200 | CCUUGGCCAUGUAAAAGUGCUUACAGUGCAGGUAGCUUUUUGAGAUCUACUGCAAUGUAAGCACUUCUUACAUUACCAUGG | MI0000113 |
| hsa-miR-106b-5p | 129 | UAAAGUGCUGACAGUGCAGAU | MIMAT0000680 | hsa-mir-106b | 201 | CCUGCCGGGGCUAAAGUGCUGACAGUGCAGAUAGUGGUCCUCUCCGUGCUACCGCACUGUGGGUACUUGCUGCUCCAGCAGG | MI0000734 |
| hsa-miR-127-3p | 130 | UCGGAUCCGUCUGAGCUUGGCU | MIMAT0000446 | hsa-mir-127 | 202 | UGUGAUCACUGUCUCCAGCCUGCUGAAGCUCAGAGGGCUCUGAUUCAGAAAGAUCAUCGGAUCCGUCUGAGCUUGGCUGGUCGGAAGUCUCAUCAUC | MI0000472 |
| hsa-miR-132-3p | 131 | UAACAGUCUACAGCCAUGGUCG | MIMAT0000426 | hsa-mir-132 | 203 | CCGCCCCCGCGUCUCCAGGGCAACCGUGGCUUUCGAUUGUUACUGUGGGAACUGGAGGUAACAGUCUACAGCCAUGGUCGCCCCGCAGCACGCCCACGCGC | MI0000449 |
| hsa-miR-140-3p | 132 | UACCACAGGGUAGAACCACGG | MIMAT0004597 | hsa-mir-140 | 204 | UGUGUCUCUCUCUGUGUCCUGCCAGUGGUUUUACCCUAUGGUAGGUUACGUCAUGCUGUUCUACCACAGGGUAGAACCACGGACAGGAUACCGGGGCACC | MI0000456 |
| hsa-miR-141-3p | 133 | UAACACUGUCUGGUAAAGAUGG | MIMAT0000432 | hsa-mir-141 | 205 | CGGCCGGCCCUGGGUCCAUCUUCCAGUACAGUGUUGGAUGGUCUAAUUGUGAAGCUCCUAACACUGUCUGGUAAAGAUGGCUCCCGGGUGGGUUC | MI0000457 |
| hsa-miR-143-3p | 134 | UGAGAUGAAGCACUGUAGCUC | MIMAT0000435 | hsa-mir-143 | 206 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | MI0000459 |
| hsa-miR-143-5p | 135 | GGUGCAGUGCUGCAUCUCUGGU | MIMAT0004599 | hsa-mir-143 | 207 | GCGCAGCGCCCUGUCUCCCAGCCUGAGGUGCAGUGCUGCAUCUCUGGUCAGUUGGGAGUCUGAGAUGAAGCACUGUAGCUCAGGAAGAGAGAAGUUGUUCUGCAGC | MI0000459 |
| hsa-miR-144-3p | 136 | UACAGUAUAGAUGAUGUACU | MIMAT0000436 | hsa-mir-144 | 208 | UGGGGCCCUGGCUGGGAUAUCAUCAUAUACUGUAAGUUUGCGAUGAGACACUACAGUAUAGAUGAUGU | MI0000460 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | | | | | ACUAGUCCGGGCACCCCC | |
| hsa-miR-146b-5p | 137 | UGAGAACUGAAUUCCAUAGGCU | MIMAT0002809 | hsa-mir-146b | 209 | CCUGGCACUGAGAACUGAAUUCCAUAGGCUGUGAGCUCUAGCAAUGCCCUGUGGACUCAGUUCUGGUGCCCGG | MI0003129 |
| hsa-miR-154-5p | 138 | UAGGUUAUCCGUGUUGCCUUCG | MIMAT0000452 | hsa-mir-154 | 210 | GUGGUACUUGAAGAUAGGUUAUCCGUGUUGCCUUCGCUUUAUUUGUGACGAAUCAUACACGGUUGACCUAUUUUUCAGUACCAA | MI0000480 |
| hsa-miR-16-2-3p | 139 | CCAAUAUUACUGUGCUGCUUUA | MIMAT0004518 | hsa-mir-16-2 | 211 | GUUCCACUCUAGCAGCACGUAAAUAUUGGCGUAGUGAAAUAUAUAUUAAACACCAAUAUUACUGUGCUGCUUUAGUGUGAC | MI0000115 |
| hsa-miR-16-5p | 140 | UAGCAGCACGUAAAUAUUGGCG | MIMAT0000069 | hsa-mir-16-1 | 212 | GUCAGCAGUGCCUUAGCAGCACGUAAAUAUUGGCGUUAAGAUUCUAAAAUUAUCUCCAGUAUUAACUGUGCUGCUGAAGUAAGGUUGAC | MI0000070 |
| hsa-miR-17-5p | 141 | CAAAGUGCUUACAGUGCAGGUAG | MIMAT0000070 | hsa-mir-17 | 213 | GUCAGAAUAAUGUCAAAGUGCUUACAGUGCAGGUAGUGAUAUGUGCAUCUACUGCAGUGAAGGCACUUGUAGCAUUAUGGUGAC | MI0000071 |
| hsa-miR-181a-5p | 271 | AACAUUCAACGCUGUCGGUGAGU | MIMAT0000256 | hsa-mir-181a-2 | 272 | AGAAGGGCUAUCAGGCCAGCCUUCAGAGGACUCCAAGGAACAUUCAACGCUGUCGGUGAGUUUGGGAUUUGAAAAAACCACUGACCGUUGACUGUACCUUGGGGUCCUUA | MI0000269 |
| hsa-miR-181b-5p | 142 | AACAUUCAUUGCUGUCGGUGGGU | MIMAT0000257 | hsa-mir-181b-1 | 214 | CCUGUGCAGAGAUUAUUUUUUAAAAGGUCACAAUCAACAUUCAUUGCUGUCGGUGGGUUGAACUGUGUGGACAAGCUCACUGAACAAUGAAUGCAACUGUGGCCCCGCUU | MI0000270 |
| hsa-miR-181c-3p | 143 | AACCAUCGACCGUUGAGUGGAC | MIMAT0004559 | hsa-mir-181c | 215 | CGGAAAAUUUGCCAAGGGUUUGGGGGAACAUUCAACCUGUCGGUGAGUUUGGGCAGCUCAGGCAAACCAUCGACCGUUGAGUGGACCCUGAGGCCUGGAAUUGCCAUCCU | MI0000271 |
| hsa-miR-181c-5p | 144 | AACAUUCAACCUGUCGGUGAGU | MIMAT0000258 | hsa-mir-181c | 216 | CGGAAAAUUUGCCAAGGGUUUGGGGGAACAUUCAACCUGUCGGUGAGUUUGGGCAGCUCAGGCAAACCAUCGACCGUUGAGU | MI0000271 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | | | | | GGACCCUGAGGCCU GGAAUUGCCAUCCU | |
| hsa-miR-185-5p | 145 | UGGAGAGAAAGGCAGUUCCUGA | MIMAT0000455 | hsa-mir-185 | 217 | AGGGGGCGAGGGAUUGGAGAGAAAGGCAGUUCCUGAUGGUCCCUCCCCAGGGGCUGGCUUUCCUCUGGUCCUUCCCUCCCA | MI0000482 |
| hsa-miR-18a-3p | 146 | ACUGCCCUAAGUGCUCCUUCUGG | MIMAT0002891 | hsa-mir-18a | 218 | UGUUCUAAGGUGCAUCUAGUGCAGAUAGUGAAGUAGAUUAGCAUCUACUGCCCUAAGUGCUCCUUCUGGCA | MI0000072 |
| hsa-miR-18a-5p | 147 | UAAGGUGCAUCUAGUGCAGAUAG | MIMAT0000072 | hsa-mir-18a | 219 | UGUUCUAAGGUGCAUCUAGUGCAGAUAGUGAAGUAGAUUAGCAUCUACUGCCCUAAGUGCUCCUUCUGGCA | MI0000072 |
| hsa-miR-18b-5p | 148 | UAAGGUGCAUCUAGUGCAGUUAG | MIMAT0001412 | hsa-mir-18b | 220 | UGUGUUAAGGUGCAUCUAGUGCAGUUAGUGAAGCAGCUUAGAAUCUACUGCCCUAAAUGCCCCUUCUGGCA | MI0001518 |
| hsa-miR-1908-5p | 149 | CGGCGGGGACGGCGAUUGGUC | MIMAT0007881 | hsa-mir-1908 | 221 | CGGGAAUGCCGCGGCGGGGACGGCGAUUGGUCCGUAUGUGUGGUGCCACCGGCCGCCGGCUCCGCCCCGGCCCCCGCCCC | MI0008329 |
| hsa-miR-191-5p | 150 | CAACGGAAUCCCAAAAGCAGCUG | MIMAT0000440 | hsa-mir-191 | 222 | CGGCUGGACAGCGGGCAACGGAAUCCCAAAAGCAGCUGUUGUCUCCAGAGCAUUCCAGCUGCGCUUGGAUUUCGUCCCCUGCUCUCCUGCCU | MI0000465 |
| hsa-miR-196b-5p | 151 | UAGGUAGUUUCCUGUUGUUGGG | MIMAT0001080 | hsa-mir-196b | 223 | ACUGGUCGGUGAUUUAGGUAGUUUCCUGUUGUUGGGAUCCACCUUUCUCUCGACAGCACGACACUGCCUUCAUUACUUCAGUUG | MI0001150 |
| hsa-miR-199b-5p | 152 | CCCAGUGUUUAGACUAUCUGUUC | MIMAT0000263 | hsa-mir-199b | 224 | CCAGAGGACACCUCCACUCCGUCUACCCAGUGUUUAGACUAUCUGUUCAGGACUCCCAAAUUGUACAGUAGUCUGCACAUUGGUUAGGCUGGGCUGGGUUAGACCCUCGG | MI0000282 |
| hsa-miR-19b-1-5p | 153 | AGUUUUGCAGGUUUGCAUCCAGC | MIMAT0004491 | hsa-mir-19b-1 | 225 | CACUGUUCUAUGGUUAGUUUUGCAGGUUUGCAUCCAGCUGUGUGAUAUUCUGCUGUGCAAAUCCAUGCAAAACUGACUGUGGUAGUG | MI0000074 |
| hsa-miR-19b-3p | 154 | UGUGCAAAUCCAUGCAAAACUGA | MIMAT0000074 | hsa-mir-19b-1 | 226 | CACUGUUCUAUGGUUAGUUUUGCAGGUUUGCAUCCAGCUGUGUGAUAUUCUGCU | MI0000074 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | | | | | GUGCAAAUCCAUGCAAAACUGACUGUGGUAGUG | |
| hsa-miR-200b-3p | 155 | UAAUACUGCCUGGUAAUGAUGA | MIMAT0000318 | hsa-mir-200b | 227 | CCAGCUCGGGCAGCCGUGGCCAUCUUACUGGGCAGCAUUGGAUGGAGUCAGGUCUCUAAUACUGCCUGGUAAUGAUGACGGCGGAGCCCUGCACG | MI0000342 |
| hsa-miR-203a | 156 | GUGAAAUGUUUAGGACCACUAG | MIMAT0000264 | hsa-mir-203a | 228 | GUGUUGGGGACUCGCGCGCUGGGUCCAGUGGUUCUUAACAGUUCAACAGUUCUGUAGCGCAAUUGUGAAAUGUUUAGGACCACUAGACCCGGCGGGCGCGGCGACAGCGA | MI0000283 |
| hsa-miR-20a-5p | 157 | UAAAGUGCUUAUAGUGCAGGUAG | MIMAT0000075 | hsa-mir-20a | 229 | GUAGCACUAAAGUGCUUAUAGUGCAGGUAGUGUUUAGUUAUCUACUGCAUUAUGAGCACUUAAAGUACUGC | MI0000076 |
| hsa-miR-20b-5p | 158 | CAAAGUGCUCAUAGUGCAGGUAG | MIMAT0001413 | hsa-mir-20b | 230 | AGUACCAAAGUGCUCAUAGUGCAGGUAGUUUUGGCAUGACUCUACUGUAGUAUGGGCACUUCCAGUACU | MI0001519 |
| hsa-miR-210-3p | 159 | CUGUGCGUGUGACAGCGGCUGA | MIMAT0000267 | hsa-mir-210 | 231 | ACCCGGCAGUGCCUCCAGGCGCAGGGCAGCCCCUGCCCACCGCACACUGCGCUGCCCCAGACCCACUGUGCGUGUGACAGCGGCUGAUCUGUGCCUGGGCAGCGCGACCC | MI0000286 |
| hsa-miR-21-3p | 160 | CAACACCAGUCGAUGGGCUGU | MIMAT0004494 | hsa-mir-21 | 232 | UGUCGGGUAGCUUAUCAGACUGAUGUUGACUGUUGAAUCUCAUGGCAACACCAGUCGAUGGGCUGUCUGACA | MI0000077 |
| hsa-miR-25-3p | 161 | CAUUGCACUUGUCUCGGUCUGA | MIMAT0000081 | hsa-mir-25 | 233 | GGCCAGUGUUGAGAGGCGGAGACUUGGGCAAUUGCUGGACGCUGCCCUGGGCAUUGCACUUGUCUCGGUCUGACAGUGCCGGC | MI0000082 |
| hsa-miR-26b-5p | 162 | UUCAAGUAAUUCAGGAUAGGU | MIMAT0000083 | hsa-mir-26b | 234 | CCGGGACCCAGUUCAAGUAAUUCAGGAUAGGUUGUGUGCUGUCCAGCCUGUUCUCCAUUACUUGGCUCGGGACCGG | MI0000084 |
| hsa-miR-301a-3p | 163 | CAGUGCAAUAGUAUUGUCAAAGC | MIMAT0000688 | hsa-mir-301a | 235 | ACUGCUAACGAAUGCUCUGACUUUAUUGCACUACUGUACUUUACAGCUAGCAGUGCAAUAGUAUUGUCAAAGCAUCUGAAAGCAGG | MI0000745 |
| hsa-miR-301b | 164 | CAGUGCAAUGAUA | MIMAT0004958 | hsa-mir-301b | 236 | GCCGCAGGUGCUCUGACGAGGUUGCACU | MI0005568 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | UUGUCAAAGC | | | | ACUGUGCUCUGAGAAGCAGUGCAAUGAUAUUGUCAAAGCAUCUGGGACCA | |
| hsa-miR-32-3p | 273 | CAAUUUAGUGUGUGUGAUAUUU | MIMAT0004505 | hsa-mir-32 | 274 | GGAGAUAUUGCACAUUACUAAGUUGCAUGUUGUCACGGCCUCAAUGCAAUUUAGUGUGUGUGAUAUUUUC | MI0000090 |
| hsa-miR-323a-3p | 165 | CACAUUACACGGUCGACCUCU | MIMAT0000755 | hsa-mir-323a | 237 | UUGGUACUUGGAGAGAGGUGGUCCGUGGCGCGUUCGCUUUAUUUAUGGCGCACAUUACACGGUCGACCUCUUUUGCAGUAUCUAAUC | MI0000807 |
| hsa-miR-324-5p | 166 | CGCAUCCCCUAGGGCAUUGGUGU | MIMAT0000761 | hsa-mir-324 | 238 | CUGACUAUGCCUCCCCGCAUCCCUAGGGCAUUGGUGUAAAGCUGGAGACCCACUGCCCCAGGUGCUGCUGGGGGUUGUAGUC | MI0000813 |
| hsa-miR-330-3p | 167 | GCAAAGCACACGGCCUGCAGAGA | MIMAT0000751 | hsa-mir-330 | 239 | CUUUGGCGAUCACUGCCUCUCUGGGCCUGUGUCUUAGGCUCUGCAAGAUCAACCGAGCAAAGCACACGGCCUGCAGAGAGGCAGCGCUCUGCCC | MI0000803 |
| hsa-miR-363-3p | 168 | AAUUGCACGGUAUCCAUCUGUA | MIMAT0000707 | hsa-mir-363 | 240 | UGUUGUCGGGUGGAUCACGAUGCAAUUUUGAUGAGUAUCAUAGGAGAAAAAUUGCACGGUAUCCAUCUGUAAACC | MI0000764 |
| hsa-miR-369-3p | 169 | AAUAAUACAUGGUUGAUCUUU | MIMAT0000721 | hsa-mir-369 | 241 | UUGAAGGGAGAUCGACCGUGUUAUAUUCGCUUUAUUGACUUCGAAUAAUACAUGGUUGAUCUUUUCUCAG | MI0000777 |
| hsa-miR-374a-5p | 170 | UUAUAAUACAACCUGAUAAGUG | MIMAT0000727 | hsa-mir-374a | 242 | UACAUCGGCCAUUAUAAUACAACCUGAUAAGUGUUAUAGCACUUAUCAGAUUGUAUUGUAAUUGUCUGUGUA | MI0000782 |
| hsa-miR-375 | 171 | UUUGUUCGUUCGGCUCGCGUGA | MIMAT0000728 | hsa-mir-375 | 243 | CCCCGCGACGAGCCCCUCCGCACAAACCGGACCUGAGCGUUUGUUCGUUCGGCUCGCGUGAGGC | MI0000783 |
| hsa-miR-376c-3p | 172 | AACAUAGAGGAAAUUCCACGU | MIMAT0000720 | hsa-mir-376c | 244 | AAAAGGUGGAUAUUCCUUCUAUGUUUAUGUUAUUUAUGGUUAAACAUAGAGGAAAUUCCACGUUUU | MI0000776 |
| hsa-miR-378a-5p | 173 | CUCCUGACUCCAGGUCCUGUGU | MIMAT0000731 | hsa-mir-378a | 245 | AGGGCUCCUGACUCCAGGUCCUGUGUUUACCUAGAAAUAGCACUGGACUUGGAGUCAGAAGGCCU | MI0000786 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| hsa-miR-451a | 174 | AAACCGUUACCAUUACUGAGUU | MIMAT0001631 | hsa-mir-451a | 246 | CUUGGGAAUGGCAAGGAAACCGUUACCAUUACUGAGUUUAGUAAUGGUAAUGGUUCUCUUGCUAUACCCAGA | MI0001729 |
| hsa-miR-454-3p | 175 | UAGUGCAAUAUUGCUUAUAGGGU | MIMAT0003885 | hsa-mir-454 | 247 | UCUGUUUAUCACCAGAUCCUAGAACCCUAUCAAUAUUGUCUCUGCUGUGUAAAUAGUUCUGAGUAGUGCAAUAUUGCUUAUAGGGUUUUGGUGUUUGGAAAGAACAAUGGGCAGG | MI0003820 |
| hsa-miR-486-3p | 176 | CGGGGCAGCUCAGUACAGGAU | MIMAT0004762 | hsa-mir-486 | 248 | GCAUCCUGUACUGAGCUGCCCCGAGGCCCUUCAUGCUGCCCAGCUCGGGGCAGCUCAGUACAGGAUAC | MI0002470 |
| hsa-miR-486-5p | 177 | UCCUGUACUGAGCUGCCCCGAG | MIMAT0002177 | hsa-mir-486 | 249 | GCAUCCUGUACUGAGCUGCCCCGAGGCCCUUCAUGCUGCCCAGCUCGGGGCAGCUCAGUACAGGAUAC | MI0002470 |
| hsa-miR-493-5p | 178 | UUGUACAUGGUAGGCUUUCAUU | MIMAT0002813 | hsa-mir-493 | 250 | CUGGCCUCCAGGGCUUUGUACAUGGUAGGCUUUCAUUCAUUCGUUUGCACAUUCGGUGAAGGUCUACUGUGUGCCAGGCCCUGUGCCAG | MI0003132 |
| hsa-miR-500a-5p | 179 | UAAUCCUUGGGUGUGCUACCAGA | MIMAT0004773 | hsa-mir-500a | 251 | GCUCCCCCUCUCUAAUCCUUGCUACCUGGGUGAGAGUGCUGUCUGAAUGCAAUGCACCUGGGCAAGGAUUCUGAGAGCGAGAGC | MI0003184 |
| hsa-miR-532-3p | 180 | CCUCCCACACCCAAGGCUUGCA | MIMAT0004780 | hsa-mir-532 | 252 | CGACUUGCUUUCUCUCCUCCAUGCCUUGAGUGUAGGACCGUUGGCAUCUUAAUUACCCUCCCACACCCAAGGCUUGCAAAAAAGCGAGCCU | MI0003205 |
| hsa-miR-545-3p | 181 | UCAGCAAACAUUUAUUGUGUGC | MIMAT0003165 | hsa-mir-545 | 253 | CCCAGCCUGGCACAUUAGUAGGCCUCAGUAAAUGUUUAUUAGAUGAAUAAAUGAAUGACUCAUCAGCAAACAUUUAUUGUGUGCCUGCUAAAGUGAGCUCCACAGG | MI0003516 |
| hsa-miR-550a-3p | 182 | UGUCUUACUCCCUCAGGCACAU | MIMAT0003257 | hsa-mir-550a-1 | 254 | UGAUGCUUUGCUGGCUGGUGCAGUGCCUGAGGGAGUAAGAGCCCUGUUGUUGUAAGAUAGUGUCUUACUCCCUCAGGCACAUCUCCAACAAGUCUCU | MI0003600 |
| hsa-miR-550a-5p | 183 | AGUGCCUGAGGGAGUAAGAGCCC | MIMAT0004800 | hsa-mir-550a-1 | 255 | UGAUGCUUUGCUGGCUGGUGCAGUGCCUGAGGGAGUAAGAGCCCUGUUGUUGU | MI0003600 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | | | | | AAGAUAGUGUCUUACUCCCUCAGGCACAUCUCCAACAAGUCUCU | |
| hsa-miR-589-5p | 184 | UGAGAACCACGUCUGCUCUGAG | MIMAT0004799 | hsa-mir-589 | 256 | UCCAGCCUGUGCCCAGCAGCCCCUGAGAACCACGUCUGCUCUGAGCUGGGUACUGCCUGUUCAGAACAAAUGCCGGUUCCCAGACGCUGCCAGCUGGCC | MI0003599 |
| hsa-miR-590-3p | 185 | UAAUUUUAUGUAUAAGCUAGU | MIMAT0004801 | hsa-mir-590 | 257 | UAGCCAGUCAGAAAUGAGCUUAUUCAUAAAAGUGCAGUAUGGUGAAGUCAAUCUGUAAUUUUAUGUAUAAGCUAGUCUCUGAUUGAAACAUGCAGCA | MI0003602 |
| hsa-miR-598-3p | 186 | UACGUCAUCGUUGUCAUCGUCA | MIMAT0003266 | hsa-mir-598 | 258 | GCUUGAUGAUGCUGCUGAUGCUGGCGGUGAUCCCGAUGGUGUGAGCUGGAAAUGGGGUGCUACGUCAUCGUUGUCAUCGUCAUCAUCAUCCGAG | MI0003610 |
| hsa-miR-627-5p | 187 | GUGAGUCUCUAAGAAAAGAGGA | MIMAT0003296 | hsa-mir-627 | 259 | UACUUAUUACUGGUAGUGAGUCUCUAAGAAAAGAGGAGGUGGUUGUUUUCCUCCUCUUUUCUUUGAGACUCACUACCAAUAAUAAGAAAUACUACUA | MI0003641 |
| hsa-miR-629-5p | 188 | UGGGUUUACGUUGGGAGAACU | MIMAT0004810 | hsa-mir-629 | 260 | UCCCUUUCCCAGGGGAGGGGCUGGGUUUACGUUGGGAGAACUUUUUACGGUGAACCAGGAGGUUCUCCCAACGUAAGCCCAGCCCCUCCCCUCUGCCU | MI0003643 |
| hsa-miR-7-5p | 189 | UGGAAGACUAGUGAUUUUGUUGU | MIMAT0000252 | hsa-mir-7-1 | 261 | UGGAUGUUGGCCUAGUUCUGUGUGGAAGACUAGUGAUUUUGUUGUUGUUUUUAGAUAACUAAAUCGACAACAAAUCACAGUCUGCCAUAUGGCACAGGCCAUGCCUCUACAG | MI0000263 |
| hsa-miR-92a-3p | 190 | UAUUGCACUUGUCCCGGCCUGU | MIMAT0000092 | hsa-mir-92a-1 | 262 | CUUUCUACACAGGUUGGGAUCGGUUGCAAUGCUGUGUUUCUGUAUGGUAUUGCACUUGUCCCGGCCUGUUGAGUUUGG | MI0000093 |
| hsa-miR-93-3p | 191 | ACUGCUGAGCUAGCACUUCCCG | MIMAT0004509 | hsa-mir-93 | 263 | CUGGGGGCUCCAAAGUGCUGUUCGUGCAGGUAGUGUGAUUACCCAACCUACUGCUGAGCUAGCACUUCCCGAGCCCCCGG | MI0000095 |
| hsa-miR-93-5p | 192 | CAAAGUGCUGUUCGUGCA | MIMAT0000093 | hsa-mir-93 | 264 | CUGGGGGCUCCAAAGUGCUGUUCGUGCAGGUAGUGUGAUU | MI0000095 |

TABLE 4-continued

Non-recent Diabetic Fracture vs Control

| mature ID | SEQ ID | mature Seq | mature Acc | hairpin | SEQ ID | hairpin Seq | hairpin Acc |
|---|---|---|---|---|---|---|---|
| | | GGUAG | | | | ACCCAACCUACUGC UGAGCUAGCACUUC CCGAGCCCCCGG | |
| hsa-miR-941 | 193 | CACCCGG CUGUGU GCACAUG UGC | MIMAT0004984 | hsa-mir-941-1 | 265 | UGUGGACAUGUGCC CAGGGCCCGGGACA GCGCCACGGAAGAG GACGCACCCGGCUG UGUGCACAUGUGCC CA | MI0005763 |
| hsa-miR-942-5p | 194 | UCUUCUC UGUUUU GGCCAU GUG | MIMAT0004985 | hsa-mir-942 | 266 | AUUAGGAGAGUAU CUUCUCUGUUUUG GCCAUGUGUGUACU CACAGCCCCUCACAC AUGGCCGAAACAGA GAAGUUACUUUCCU AAU | MI0005767 |
| hsa-miR-96-5p | 195 | UUUGGC ACUAGCA CAUUUU UGCU | MIMAT0000095 | hsa-mir-96 | 267 | UGGCCGAUUUUGG CACUAGCACAUUUU UGCUUGUGUCUCU CCGCUCUGAGCAAU CAUGUGCAGUGCCA AUAUGGGAAA | MI0000098 |
| hsa-miR-98-5p | 196 | UGAGGU AGUAAG UUGUAU UGUU | MIMAT0000096 | hsa-mir-98 | 268 | AGGAUUCUGCUCAU GCCAGGGUGAGGUA GUAAGUUGUAUUG UUGUGGGUAGGG AUAUUAGGCCCCAA UUAGAAGAUAACUA UACAACUUACUACU UUCCCUGGUGUGU GGCAUAUUCA | MI0000100 |

LITERATURE

Anastas, J. N., & Moon, R. T. (2013). WNT signalling pathways as therapeutic targets in cancer. *Nature Reviews Cancer*, 13(1), 11-26. doi:10.1038/nrc3419

Bartel, D. P. (2009). MicroRNAs: target recognition and regulatory functions. *Cell*, 136(2), 215-233. doi:10.1016/j.cell.2009.01.002

Canalis, E. (2013). Wnt signalling in osteoporosis: mechanisms and novel therapeutic approaches. *Nature Reviews. Endocrinology*, 9(10), 575-83. doi:10.1038/nrendo.2013.154

Cefalu, C. A. (2004). Is bone mineral density predictive of fracture risk reduction? *Current Medical Research and Opinion*, 20(3), 341-349. doi:10.1185/030079903125003062

Deng, Y., Bi, X., Zhou, H., You, Z., Wang, Y., Gu, P., & Fan, X. (2014). Repair of critical-sized bone defects with anti-miR-31-expressing bone marrow stromal stem cells and poly(glycerol sebacate) scaffolds. *European Cells & Materials*, 27, 13-24; discussion 24-5. Retrieved from http://www.ncbi.nlm.nih.gov/pubmed/24425157

Dong, S., Yang, B., Guo, H., & Kang, F. (2012). MicroRNAs regulate osteogenesis and chondrogenesis. *Biochemical and Biophysical Research Communications*, 418(4), 587-591. doi:10.1016/j.bbrc.2012.01.075

Kanis, J. A., McCloskey, E. V, Johansson, H., Cooper, C., Rizzoli, R., Reginster, J.-Y., & Scientific Advisory Board of the European Society for Clinical and Economic Aspects of Osteoporosis and Osteoarthritis (ESCEO) and the Committee of Scientific Advisors of the International Osteoporosis Foundation (IOF). (2013). European guidance for the diagnosis and management of osteoporosis in postmenopausal women. *Osteoporosis International: A Journal Established as Result of Cooperation between the European Foundation for Osteoporosis and the National Osteoporosis Foundation of the USA*, 24(1), 23-57. doi:10.1007/s00198-012-2074-y Kapinas, K., Kessler, C. B., & Delany, A. M. (2009). miR-29 suppression of osteonectin in osteoblasts: regulation during differentiation and by canonical Wnt signaling. *Journal of Cellular Biochemistry*, 108(1), 216-224. doi:10.1002/jcb.22243

Keller, A., Leidinger, P., Bauer, A., Elsharawy, A., Haas, J., Backes, C., . . . Meese, E. (2011). Toward the blood-borne miRNome of human diseases. *Nature Methods*, 8(10), 841-3. doi:10.1038/nmeth.1682

Li, Z., Hassan, M. Q., Volinia, S., van Wijnen, A. J., Stein, J. L., Croce, C. M., . . . Stein, G. S. (2008). A microRNA signature for a BMP2-induced osteoblast lineage commitment program. *Proceedings of the National Academy of Sciences of the United States of America*, 105(37), 13906-13911. doi:10.1073/pnas.0804438105

Rubin, K. H., Abrahamsen, B., Friis-Holmberg, T., Hjelmborg, J. V. B., Bech, M., Hermann, A. P., . . . Brixen, K. (2013). Comparison of different screening tools (FRAX®, OST, ORAI, OSIRIS, SCORE and age alone) to identify women with increased risk of fracture. A population-based prospective study. *Bone*, 56(1), 16-22. doi:10.1016/j.bone.2013.05.002

Seeliger, C., Karpinski, K., Haug, A., Vester, H., Schmitt, A., Bauer, J., & van Griensven, M. (2014). Five Freely Circulating miRNAs and Bone Tissue miRNAs are Associated with Osteoporotic Fractures. *Journal of Bone and Mineral Research: The Official Journal of the American Society for Bone and Mineral Research*. doi:10.1002/jbmr.2175

Trompeter, H.-I., Dreesen, J., Hermann, E., Iwaniuk, K. M., Hafner, M., Renwick, N., . . . Wernet, P. (2013). MicroRNAs miR-26a, miR-26b, and miR-29b accelerate osteogenic differentiation of unrestricted somatic stem cells from human cord blood. *BMC Genomics*, 14(1), 111. doi:10.1186/1471-2164-14-111

Van Wijnen, A. J., van de Peppel, J., van Leeuwen, J. P., Lian, J. B., Stein, G. S., Westendorf, J. J., . . . Kakar, S. (2013). MicroRNA functions in osteogenesis and dysfunctions in osteoporosis. *Current Osteoporosis Reports*, 11(2), 72-82. doi:10.1007/s11914-013-0143-6

Vasikaran, S., Eastell, R., Bruyere, O., Foldes, A. J., Garnero, P., Griesmacher, A., . . . IOF-IFCC Bone Marker Standards Working Group. (2011). Markers of bone turnover for the prediction of fracture risk and monitoring of osteoporosis treatment: a need for international reference standards. *Osteoporosis International: A Journal Established as Result of Cooperation between the European Foundation for Osteoporosis and the National Osteoporosis Foundation of the USA*, 22(2), 391-420. doi:10.1007/s00198-010-1501-1

Weilner, S., Schraml, E., Redl, H., Grillari-Voglauer, R., & Grillari, J. (2013). Secretion of microvesicular miRNAs in cellular and organismal aging. *Experimental Gerontology*, 48(7), 626-633. doi:10.1016/j.exger.2012.11.017

Zhao, X., Xu, D., Li, Y., Zhang, J., Liu, T., Ji, Y., . . . Xie, X. (2013). MicroRNAs regulate bone metabolism. *Journal of Bone and Mineral Metabolism*. doi:10.1007/s00774-013-0537-7

The invention claimed is:

1. A method of diagnosing and treating osteoporosis in a subject, comprising the steps of:
   a) providing a blood sample from said subject;
   b) measuring a level of hsa-miR-188-3p and at least one additional miRNA selected from the group consisting of:
      i) a group II miRNA selected from the group consisting of hsa-miR-127-3p, hsa-miR-143-3p, hsa-miR-214-3p, hsa-miR-30e-3p, and hsa-miR-942 or isoforms or variants thereof; and
      ii) a group m miRNA selected from the group consisting of hsa-miR-106b-5p, hsa-miR-141-3p, hsa-miR-19b-3p, hsa-miR-21-3p, hsa-miR-375, hsa-miR-486-3p, and hsa-miR-532-3p, or isoforms or variants thereof;
   c) comparing the levels of said miRNAs with the levels of corresponding miRNAs in a reference blood sample from a healthy individual; and
   d) when the levels of said miRNAs are higher or lower than the levels of corresponding miRNAs in a reference blood sample from a healthy individual, then treating the subject for osteoporosis by administering to the subject a composition selected from the group consisting of teriparatide, denosumab, blosozumab, romosozumab, a bisphonate, and a bone growth factor.

2. The method of claim 1, wherein there is a difference of more than one standard deviation in the levels of the miRNAs in the blood sample from the subject compared to the levels of the miRNAs in the reference blood sample.

3. The method of claim 1, wherein the levels of at least 4 miRNAs are measured.

4. The method of claim 1, wherein the levels of all of the miRNAs of group II and/or group III are measured.

5. The method of claim 1, further comprising the step of measuring levels of hsa-miR-106a-5p, hsa-miR-133b, hsa-miR-18a-3p, hsa-miR-196b-5p, hsa-miR-199b-5p, hsa-miR-200b-3p, hsa-miR-203a, hsa-miR-20b-5p, hsa-miR-323a-3p, hsa-miR-330-3p, hsa-miR-369-3p, hsa-miR-376c-3p, hsa-miR-378a-5p, hsa-miR-454-3p, hsa-miR-500a-5p, hsa-miR-550a-5p, hsa-miR-941, and hsa-miR-942.

6. The method of claim 1, wherein one or more further miRNAs are detected, wherein said miRNAs are:
   a) differentially regulated in osteoporotic individuals as compared to healthy individuals, and
   b) involved in osteogenic differentiation and/or in osteoclastogenic activation.

7. The method of claim 6, wherein said further miRNAs are group V miRNAs selected from the group consisting of hsa-miR-140-5p, hsa-miR-146a-5p, hsa-hsa-miR-199a-5p, hsa-miR-20a, hsa-miR-200a, hsa-miR-217, hsa-miR-218, hsa-miR-26a, hsa-miR-27a, hsa-miR-2861, hsa-miR-29a-3p, hsa-miR-29b-3p, hsa-miR-29c-3p, hsa-miR-204-5p, hsa-miR-335-5p, hsa-miR-34c, hsa-miR-370-3p, hsa-miR-3960 and hsa-miR-503-5p, or isoforms and variants thereof.

8. The method of claim 1, further comprising the step of performing a bone imaging procedure on the subject in order to identify whether the subject has a bone fracture.

9. The method of claim 1, wherein the subject is a osteoporosis or osteopenia patient suffering from or at risk of developing bone fractures, or is a patient at risk of or suffering from type 2 diabetes mellitus.

10. The method of claim 1, wherein the difference in miRNA levels is determined by quantitative or digital PCR, sequencing, microarray, Luminex nucleic acid assays, or other hybridization-based techniques.

11. The method of claim 1, wherein the subject is treated if there is a difference of more than 1.5 fold in the levels of said miRNAs in the blood sample from the subject when compared to the levels of the miRNAs in the reference blood sample.

12. The method of claim 1, wherein the bisphonate is alendronate or zolendronate.

13. The method of claim 1, wherein the bone growth factor is BMP-2 or BMP-7.

* * * * *